US011261254B1

(12) United States Patent
Koopman et al.

(10) Patent No.: US 11,261,254 B1
(45) Date of Patent: Mar. 1, 2022

(54) ANTIBODIES

(71) Applicant: GENMAB A/S, Copenhagen V (DK)

(72) Inventors: Louise Koopman, Utrecht (NL);
Patrick Engelberts, Amersfoort (NL);
Dennis Verzijl, Amstelveen (NL);
Edward N. Van Den Brink, Halfweg (NL); Rik Rademaker, Utrecht (NL);
Sieto Bosgra, Amsterdam (NL);
Frederikke L. Egerod, Copenhagen (DK); David Satijn, Nieuwegein (NL);
Esther C. W. Breij, Driebergen (NL)

(73) Assignee: GENMAB A/S, Copenhagen V (DK)

( * ) Notice: Subject to any disclaimer, the term of this patent is extended or adjusted under 35 U.S.C. 154(b) by 0 days.

(21) Appl. No.: 17/494,545

(22) Filed: Oct. 5, 2021

Related U.S. Application Data

(62) Division of application No. 17/204,604, filed on Mar. 17, 2021.

(30) Foreign Application Priority Data

Mar. 18, 2020 (EP) .................................. 20164059

(51) Int. Cl.
| | | |
|---|---|---|
| C07K 16/00 | (2006.01) | |
| C07K 16/28 | (2006.01) | |
| A61P 35/00 | (2006.01) | |
| A61K 39/00 | (2006.01) | |

(52) U.S. Cl.
CPC .......... *C07K 16/2827* (2013.01); *A61P 35/00* (2018.01); *C07K 16/2809* (2013.01); *A61K 2039/505* (2013.01); *C07K 2317/21* (2013.01); *C07K 2317/24* (2013.01); *C07K 2317/31* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,589,466 A | 12/1996 | Felgner et al. |
| 5,731,168 A | 3/1998 | Carter et al. |
| 5,973,972 A | 10/1999 | Kwon et al. |
| 6,077,835 A | 6/2000 | Hanson et al. |
| 7,612,181 B2 | 11/2009 | Wu et al. |
| 7,951,918 B2 | 5/2011 | Glaser et al. |
| 9,150,663 B2 | 10/2015 | Labrijn et al. |
| 9,212,230 B2 | 12/2015 | Schuurman et al. |
| 10,150,813 B2 | 12/2018 | Leong et al. |
| 10,344,050 B2 | 7/2019 | Gramer et al. |
| 10,407,501 B2 | 9/2019 | Van Den Brink et al. |
| 10,465,006 B2 | 11/2019 | Van Den Brink et al. |
| 10,544,220 B2 | 1/2020 | Engelberts et al. |
| 10,590,206 B2 | 3/2020 | Labrijn et al. |
| 10,597,464 B2 | 3/2020 | Labrijn et al. |
| 10,906,991 B2 | 2/2021 | Schuurman et al. |
| 2010/0105874 A1 | 4/2010 | Schuurman et al. |
| 2010/0155133 A1 | 6/2010 | Makwinski et al. |
| 2010/0226923 A1 | 9/2010 | Rao et al. |
| 2013/0039913 A1 | 2/2013 | Labrijn et al. |
| 2014/0303356 A1 | 10/2014 | Gramer et al. |
| 2015/0175707 A1 | 6/2015 | De Jong et al. |
| 2015/0337049 A1 | 11/2015 | Labrijn et al. |
| 2016/0046727 A1 | 2/2016 | Labrijn et al. |
| 2016/0159930 A1 | 6/2016 | Schuurman et al. |
| 2016/0168247 A1 | 6/2016 | Van Den Brink et al. |
| 2016/0333095 A1 | 11/2016 | Van Den Brink et al. |
| 2017/0233497 A1 | 8/2017 | Labrijn et al. |
| 2017/0355767 A1 | 12/2017 | Engelberts et al. |
| 2019/0085080 A1 | 3/2019 | Kaplan et al. |
| 2019/0284278 A1 | 9/2019 | Rademaker et al. |
| 2020/0048304 A1 | 2/2020 | Gramer et al. |
| 2020/0123255 A1 | 4/2020 | Van Den Brink et al. |
| 2020/0199229 A1 | 6/2020 | Van Den Brink et al. |
| 2020/0199231 A1 | 6/2020 | Engelberts et al. |
| 2020/0262932 A1 | 8/2020 | Labrijn et al. |
| 2020/0332022 A1 | 10/2020 | Labrijn et al. |
| 2021/0230301 A1 | 7/2021 | De Jong et al. |
| 2021/0292418 A1 | 9/2021 | Koopman et al. |

FOREIGN PATENT DOCUMENTS

| | | |
|---|---|---|
| CN | 102250246 A | 11/2011 |
| EP | 1870459 A1 | 12/2007 |
| EP | 3492591 A1 | 6/2019 |
| WO | 98/50431 A2 | 11/1998 |
| WO | 2000/46147 A2 | 8/2000 |
| WO | 00/70087 A1 | 11/2000 |
| WO | 2003/074569 A2 | 9/2003 |

(Continued)

OTHER PUBLICATIONS

Clin Cancer Res; 25(9) May 1, 2019, published online Feb. 8, 2019 (Year: 2019).*
Abdiche, Y. et al., "Exploring blocking assays using Octet, ProteOn, and Biacore biosensors," Anal Biochem., vol. 386(2): 172-180 (2009).
Almagro & Fransson, "Frontiers in Bioscience," vol. 13:1619-1633 (2008).
Benvenisty, N. et al., "Direct introduction of genes into rats and expression of the genes," PNAS, vol. 83: 9551-9555 (1986).
Berglund, L. et al., "The epitope space of the human proteome," Protein Science, vol. 17:606-613 (2008).

(Continued)

*Primary Examiner* — Meera Natarajan
(74) *Attorney, Agent, or Firm* — Nelson Mullins Riley & Scarborough LLP; Jane E Remillard, Esq.; Christopher L Frank

(57) ABSTRACT

The present invention relates to antibodies binding to B7H4, including bispecific antibodies binding to B7H4 and CD3. The invention further provides pharmaceutical compositions comprising the antibodies and use of the antibodies for therapeutic and diagnostic procedures, in particular in cancer therapy.

30 Claims, 23 Drawing Sheets
Specification includes a Sequence Listing.

(56) References Cited

FOREIGN PATENT DOCUMENTS

| | | |
|---|---|---|
| WO | 2005/004809 A2 | 1/2005 |
| WO | 2005/061547 A2 | 7/2005 |
| WO | 2007/059782 A1 | 5/2007 |
| WO | 2007/110205 A2 | 10/2007 |
| WO | 2008/003116 A2 | 1/2008 |
| WO | 2008/119353 A1 | 10/2008 |
| WO | 2008/157379 A2 | 12/2008 |
| WO | 2009/040562 A1 | 4/2009 |
| WO | 2009/058383 A2 | 5/2009 |
| WO | 2009/073533 A2 | 6/2009 |
| WO | 2009/080254 A1 | 7/2009 |
| WO | 2009/089004 A1 | 7/2009 |
| WO | 2010/059315 A1 | 5/2010 |
| WO | 2010/080538 A1 | 7/2010 |
| WO | 2010/111625 A1 | 9/2010 |
| WO | 2010/129304 A2 | 11/2010 |
| WO | 2010/134666 A1 | 11/2010 |
| WO | 2011/028952 A1 | 3/2011 |
| WO | 2011/069104 A2 | 6/2011 |
| WO | 2011/117329 A1 | 9/2011 |
| WO | 2011/131746 A2 | 10/2011 |
| WO | 11/143545 A1 | 11/2011 |
| WO | 2011/147986 A1 | 12/2011 |
| WO | 2012/023053 A2 | 2/2012 |
| WO | 2012/025525 A1 | 3/2012 |
| WO | 2012/025530 A1 | 3/2012 |
| WO | 2012/058768 A1 | 5/2012 |
| WO | 2013/060867 A2 | 5/2013 |
| WO | 2014/081202 A1 | 5/2014 |
| WO | 2014108483 A1 | 7/2014 |
| WO | 2014/159835 A1 | 10/2014 |
| WO | 2015/001085 A1 | 1/2015 |
| WO | 2016/110576 A1 | 7/2016 |
| WO | 2017/009442 A1 | 1/2017 |

OTHER PUBLICATIONS

Bird, R. et al., "Single-Chain Antigen-Binding Proteins," Science, vol. 242:423-426 (1988).
Blankenship JW, et al. "Abstract #5465: CD79BxDR SCORPIONTM molecule: a single chain, bispecific immunotherapeutic with potent in vitro activity against B cell lymphoma," AACR 100 th Annual meeting 2009 (Abstract # 5465) 4 pages (2009).
Bostrom, J. et al., "Variants of the Antibody Herceptin That Interact with HER2 and VEGF at the Antigen Binding Site," Science, vol. 323: 1610-1614 (2009).
Brochet X, et al., "IMGT/V-QUEST: the highly customized and integrated system for IG and TR standardized V-J and V-D-J sequence analysis," Nucl. Acids Res., vol. 36, Web server Issue, W503-W508 (2008).
Chiu, M. et al., "Antibody Structure and Function: The Basis for Engineering Therapeutics," Antibodies, vol. 8(55): 80 pages (2019).
Corada, M. et al., "Monoclonal antibodies directed to different regions of vascular endothelial cadherin extracellular domain affect adhesion and clustering of the protein and modulate endothelial permeability," Blood, vol. 97:1679-1684 (2001).
Coraro, CM, et al., "Enhancing the efficiency of DNA-mediated gene transfer in mammalian cells," Somatic Cell Genetics, vol. 7(5): 603-611(1981).
Deo, Y. et al., "Bispecific molecules directed to the Fc receptor for IgA (Fc alpha RI, CD89) and tumor antigens efficiently promote cell-mediated cytotoxicity of tumor targets in whole blood," J Immunol., vol. 160(4):1677-1686 (1998).
Dimasi, N. et al., "The Design and Characterization of Oligospecific Antibodies for Simultaneous Targeting of Multiple Disease Mediators," J Mol Biol., vol. 393(3):672-692 (2009).
Dondelinger, M, et al., "Understanding the Significance and Implications of Antibody Numbering and Antigen-Binding Surface/Residue Definition," Frontiers in Immulology, vol. 9: 1-15 (2019).
Doppalapudi, V.R., et al., "Chemically programmed antibodies: Endothelin receptor targeting CovX-Bodies," Bioorg. Med. Chem. Lett., vol. 17: 501-506 (2007).
Engelberts, P. et al.,"DuoBody-CD3xCD20 induces potent T-cell-mediated killing of malignant B cells in preclinical models and provides opportunities for subcutaneous dosing," EBioMedicine, vol. 52: 102625 (2020).
Gramer, M. et al., "Production of stable bispecific IgG1 by controlled Fab-arm exchange: scalability from bench to large-scale manufacturing by application of standard approaches," MAbs, vol. 5: 962-973 (2013).
Grant, G.A., et al., "Expression and secretion vectors for yeast," Methods in Enzymol., vol. 153: 516-544 (1987).
Hmila, A. et al., "A bispecfic nanobody to provide full protection againstlethal scorpion envenoming," FASEB J., vol. 24: 3479-3489 (2010).
Holt, L. et al., "Domain antibodies: proteins for therapy," Trends Biotechnol., vol. 21(11):484-490 (2003).
Iizuka, A. et al., "A T-cell-engaging B7-H4/CD3-bispeci?c Fab-scFv Antibody Targets Human Breast Cancer," Clin Cancer Res., vol. 25: 2925-2934 (2019).
Kaur and Janakiram, "B7x-from bench to bedside," ESMO Open, vol. 4:e000554: 5 pages (2019).
Kontermann, R. et al., "Bispecific Antibodies," Drug Discov Today, vol. 20(7):838-847 (2015).
Kontermann, R. et al., "Dual targeting strategies with bispecific antibodies," MAbs, vol. 4(2):182-197 (2012).
Kulkarni-Kale, U. et al., "CEP: a conformational epitope prediction server," Nucleic Acid Research, vol. 33:W168-W171 (2005).
Labrijn, A. et al., "Efficient generation of stable bispecific IgG1 by controlled Fab-arm exchange," PNAS, vol. 110:5145-50(2013).
Lafleur, D. et al., "Monoclonal antibody therapeutics with up to five specificities Functional enhancement through fusion of target-specific peptides," MAbs, vol. 5(2):208-218 (2013).
Lawrence, L. et al., "Orientation of antigen binding sites in dimeric and trimeric single chain Fv antibody fragments," FEBS Lett., vol. 425(3):479-484 (1998).
Le Gall, F. et al., "Effect of linker sequences between the antibody variable domains on the formation, stability and biological activity of a bispecific tandem diabody," Protein Eng Des Sel., vol. 17(4):357-366 (2004).
Lefranc MP. et al., "IMGT, the international ImMunoGeneTics database," Nucleic Acids Research, vol. 27: 209-212 (1999).
Lindhofer, H, et al., "Preferential species-restricted heavy/light chain pairing in rat/mouse quadromas. Implications for a single-step purification of bispecific antibodies," J Immunol, vol. 155: 219-225 (1995).
Liu et al., Antibodies, Nov. 17, 2020;9(4):64; 29(10):457-66.
Iizuka, A. et al., "A T-cell-engaging B7-H4/CD3-bispecific Fab-scFv Antibody Targets Human Breast Cancer," Clin Cancer Res., vol. 25(9): 2925-2934 (2019).
Marvin, J, et al., "Recombinant approaches to IgG-like bispecific antibodies," Acta Pharmacol Sinica, vol. 26: 649-658 (2005).
Padlan, E.A. et al., "X-ray crystallography of antibodies," (Advances in Protein Chemistry, vol. 49:57-133 (1996).
Pearce, L. et al., "Linear gene fusions of antibody fragments with streptavidin can be linked to biotin labelled secondary molecules to form bispecific reagents," Biochem Mol Biol Int., vol. 42(6):1179-1188 (1997).
Podojil, J. et al., "Potential targeting of B7-H4 for the treatment of cancer," Immunological Reviews, vol. 276: 40-51 (2017).
Prasad, D. et al., "B7S1, a Novel B7 Family Member that Negatively Regulates T Cell Activation," Immunity, vol. 18: 863-873 (2003).
Revets, H. et al., "Nanobodies as novel agents for cancer therapy," Expert Opion on Biol Ther., vol. 5(1):111-124 (2005).
Schakowski, F. et al., "A novel minimal-size vector (MIDGE) improves transgene expression in colon carcinoma cells and avoids transfection of undesired DNA," Mol Therapy, vol. 3(5): 793-800 (2001).
Schoonjans, R. et al., "Fab chains as an efficient heterodimerization scaffold for the production of recombinant bispecific and trispecific antibody derivatives," J Immunol., vol. 165(12):7050-7057 (2000).
Shields, R. et al., "High resolution mapping of the binding site on human IgG1 for Fc gamma RI, Fc gamma RII, Fc gamma RIII, and

(56) References Cited

OTHER PUBLICATIONS

FcRn and design of IgG1 variants with improved binding to the Fc gamma R," J Biol Chem,. vol. 276(9):6591-604 (2001).

Sica, G. et al., "B7-H4, a Molecule of the B7 Family, Negatively Regulates T Cell Immunity," Immunity, vol. 18:849-861 (2003).

Smith, J. et al., "Tumor Regression and Delayed Onset Toxicity Following B7-H4 CAR T Cell Therapy," Molecular Therapy, vol. 24 (Iss. 11) 1987-1999 (2016).

Sykes, K, et al., "Linear expression elements: a rapid, in vivo, method to screen for gene functions," Nature Biotech, vol. 17:355-359 (1999).

Trabolsi, A et al., "T Cell-Activating Bispecific Antibodies in Cancer Therapy," Journ of Immunology, vol. 203(1):585-592 (2019).

Van Heeke, G, et al., "Expression of human asparagine synthetase in *Escherichia coli*," J Biol Chem, vol. 264 (10):5503-5509 (1989).

Wainberg, Z.A. et al., "PA150 (B7-H4 antibody) phase I update in advanced solid tumours:Monotherapy and in combination with pembrolizumab" Annals of Oncology, vol. 30 (Suppl. 5) v489 (1198P) 1 page (2019).

Ward, E.S. et al., "Binding activities of a repertoire of single immunoglobulin variable domains secreted from *Escherichia coli*," Nature, vol. 341:544-546 (1989).

Wigler, M. et al., "Biochemical transfer of single-copy eucaryotic genes using total cellular DNA as donor," Cell, vol. 14(3): 725-731 (1978).

U.S. Appl. No. 14/760,157, filed Mar. 17, 2015, Rob N. De Jong.
U.S. Appl. No. 16/783,720, filed Feb. 6, 2020, Rob N. De Jong.
U.S. Appl. No. 14/902,757, filed Jan. 4, 2016, Edward Van Den Brink.
U.S. Appl. No. 16/582,428, filed Sep. 25, 2019, Edward Van Den Brink.
U.S. Appl. No. 15/110,414, filed Jul. 8, 2016, Edward Van Den Brink.
U.S. Appl. No. 16/544,376, filed Aug. 19, 2019, Edward Van Den Brink.
U.S. Appl. No. 15/744,317, filed Jan. 12, 2018, Rik Rademaker.
U.S. Appl. No. 14/934,956, filed Nov. 6, 2015, Janine Schuurman.
U.S. Appl. No. 12/593,759, filed Jan. 6, 2010, Janine Schuurman.
U.S. Appl. No. 13/642,253, filed Oct. 24, 2012, Aran Frank Labrijn.
U.S. Appl. No. 14/830,336, filed Aug. 19, 2015, Aran Frank Labrijn.
U.S. Appl. No. 15/414,122, filed Jan. 24, 2017, Aran Frank Labrijn.
U.S. Appl. No. 16/777,053, filed Jan. 30, 2020, Aran Frank Labrijn.
U.S. Appl. No. 14/353,962, filed Apr. 24, 2014, Michael Gramer.
U.S. Appl. No. 16/426,647, filed May 30, 2019, Michael Gramer.
U.S. Appl. No. 14/760,157, Nov. 6, 2019, M. Natarajan.
U.S. Appl. No. 14/760,157, Feb. 7, 2019, M. Natarajan.
U.S. Appl. No. 14/760,157, Aug. 27, 2018, M. Natarajan.
U.S. Appl. No. 14/760,157, Apr. 9, 2018, M. Natarajan.
U.S. Appl. No. 14/760,157, Sep. 20, 2017, M. Natarajan.
U.S. Appl. No. 14/760,157, Feb. 17, 2017, M. Natarajan.
U.S. Appl. No. 15/110,414, May 1, 2019, Z. Skelding.
U.S. Appl. No. 15/110,414, Nov. 27, 2018, Z. Skelding.
U.S. Appl. No. 15/110,414, May 24, 2018, Z. Skelding.
U.S. Appl. No. 14/934,956, Oct. 1, 2020, B. Duffy.
U.S. Appl. No. 14/934,956, Dec. 26, 2019, B. Duffy.
U.S. Appl. No. 14/934,956, May 30, 2019, B. Duffy.
U.S. Appl. No. 14/934,956, Nov. 1, 2018, B. Duffy.
U.S. Appl. No. 14/936,956, Feb. 7, 2018, B. Duffy.
U.S. Appl. No. 14/934,956, Aug. 1, 2017, B. Duffy.
U.S. Appl. No. 13/642,253, May 22, 2015, J. Roarke.
U.S. Appl. No. 13/642,253, Jan. 22, 2015, J. Roarke.
U.S. Appl. No. 13/642,253, Sep. 11, 2014, J. Roarke.
U.S. Appl. No. 13/642,253, Apr. 23, 2014, J. Wu.
U.S. Appl. No. 14/830,336, Oct. 27, 2016, J. Roarke.
U.S. Appl. No. 14/830,336, Jun. 23, 2016, J. Roarke.
U.S. Appl. No. 15/414,122, Jan. 27, 2020, J. Roarke.
U.S. Appl. No. 15/414,122, Dec. 13, 2019, J. Roarke.
U.S. Appl. No. 15/414,122, Apr. 9, 2019, J. Roarke.
U.S. Appl. No. 15/414,122, Sep. 13, 2018, J. Roarke.
U.S. Appl. No. 15/414,122, Apr. 20, 2018, J. Roarke.
U.S. Appl. No. 14/353,962, Mar. 1, 2019, P. Huynh.
U.S. Appl. No. 14/353,962, Jul. 20, 2018, P. Huynh.
U.S. Appl. No. 14/353,962, Nov. 6, 2017, P. Huynh.
U.S. Appl. No. 14/353,962, May 30, 2017, P. Huynh.
U.S. Appl. No. 14/353,962, Sep. 13, 2016, P. Huynh.
U.S. Appl. No. 14/353,962, Mar. 23, 2016, P. Huynh.
U.S. Appl. No. 14/353,962, Sep. 23, 2015, P. Huynh.
U.S. Appl. No. 14/426,647, Apr. 29, 2021, P. Huynh.
U.S. Appl. No. 14/426,647, Nov. 13, 2020, P. Huynh.
U.S. Appl. No. 14/902,757, Jun. 26, 2019, Z. Skelding.
U.S. Appl. No. 14/902,757, Mar. 14, 2019, Z. Skelding.
U.S. Appl. No. 14/902,757, Jul. 30, 2018, Z. Skelding.
U.S. Appl. No. 14/902,757, Dec. 18, 2017, Z. Skelding.
U.S. Appl. No. 15/744,317, Aug. 20, 2021, L. Yoa.
U.S. Appl. No. 15/744,317, Apr. 2, 2021, L. Yoa.
U.S. Appl. No. 12/593,759, Aug. 4, 2015, B. Duffy.
U.S. Appl. No. 12/593,759, Oct. 14, 2014, B. Duffy.
U.S. Appl. No. 12/593,759, Apr. 23, 2014, B. Duffy.
U.S. Appl. No. 12/593,759, Aug. 3, 2012, B. Duffy.

Wranik, B. et al., "LUZ-Y, a Novel Platform for the Mammalian Cell Production of Full-length IgG-bispecific Antibodies," J. Biol. Chem., vol. 287(52): 43331-43339 (2012).

Wu, C. et al., "Generation and Characterization of a Dual Variable Domain Immunoglobulin (DVD-Ig) Molecule," In: Antibody Engineering, Springer Berlin Heidelberg, Chapter 19: 12 pages (2010).

Zhu, X. et al., "COMBODY: one-domain antibody multimer with improved avidity," Immunol Cell Biol., vol. 88(6):667-675 (2010).

* cited by examiner

MDA-MB-468

HCC1954

ANTIBODIES

RELATED APPLICATIONS

This application is a division of U.S. application Ser. No. 17/204,604, filed Mar. 17, 2021, which claims priority to European Patent Application No. 20164059.6, filed Mar. 18, 2020. The content of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Oct. 5, 2021, is named GMI_204DV_Sequence_Listing.txt and is 78,207 bytes in size.

FIELD OF INVENTION

The present invention relates to antibodies binding to B7H4, in particular to bispecific antibodies binding to B7H4 and CD3. The invention further provides pharmaceutical compositions comprising the antibodies and use of the antibodies for therapeutic and diagnostic procedures, in particular in cancer therapy.

INTRODUCTION

B7H4 (B7-H4, V-set domain containing T cell activation inhibitor 1 or VTCN1) is a member of the B7 family of proteins, which family comprises cell-surface protein ligands that bind to receptors on lymphocytes. The B7 family plays an important role in the regulation of immune responses. B7H4 negatively regulates T cell-mediated immune responses by inhibiting T cell activation, proliferation, cytokine production and cytotoxic activity (Prasad et al., 2003, Immunity 18: 863-873). B7H4 is a type I transmembrane protein that includes a short intracellular domain, a hydrophobic transmembrane domain, and an extracellular domain with an IgV- and an IgC-like domain with four conserved cysteine residues and seven sites for N-linked glycosylation. (Sica et al., 2003, Immunity 18: 849-861). To date, no receptor for B7H4 has been identified.

In normal adult tissue, B7H4 expression is very limited, whereas B7H4 expression is found on tumor cells in numerous cancer tissues (Kaur and Janakiram, 2019, ESMO Open 4:e000554). In cancer, B7H4 expression is correlated with advanced stages of cancer, poor prognosis, and decreased overall patient survival.

Hence, targeting of B7H4 has been proposed for the treatment of cancer (Podojil and Miller, Immunological Reviews, 2017: 276; 40-51). Currently, B7H4 binding antibodies are in development for cancer therapy. For example, FPA150 is an afucosylated human antibody that relieves the B7H4-mediated suppression of T cell activation and exhibits antibody dependent cellular cytotoxicity (ADCC) activity (Wainberg et al., 2019, Annals of Oncology 30, Suppl. 5, v489 (1198P). It is currently in early clinical trials as a monotherapy or in combination with pembrolizumab in advanced solid tumors.

Efforts to target T cells to B7H4 have also been made. A B7H4/CD3-bispecific single chain antibody, Fab scFv, was made based on the Fab and single-chain variable fragments (scFv) structure of a mouse anti-human B7H4 antibody and a mouse anti-human CD3 antibody (Iizuka et al., 2019, Clin Cancer Res 25: 2925-2934). Smith et al. have described engineered T cells with B7H4-specific chimeric antigen receptors (CARs) that displayed anti-tumor activity against B7H4-positive human ovarian tumor xenografts, but which also showed multi-organ lymphocytic infiltration and lethal toxicity (Smith et al. 2016, Molecular Therapy, Vol. 24 Iss. 11 pp 1987-99) in mice.

While there has been some progress made, there is a need for the development of antibody-based cancer therapy targeting B7H4 that is efficacious and/or safe for human use.

SUMMARY OF INVENTION

It is an object of the present invention to provide for antibodies comprising an antigen-binding region capable of binding to human B7H4 and an antigen-binding region that binds to CD3, such as human CD3ε (epsilon). The antigen-binding regions of such antibodies comprise at least human framework regions, such as e.g FR1, FR2, FR3 and FR4. Most preferred is that all framework regions are human. Such antigen-binding regions are humanized and/or human antigen-binding regions. These antibodies are useful in the treatment of conditions wherein specific targeting and T cell mediated killing of B7H4 expressing cells is desired, e.g. in conditions such as cancer. Preferably, such an antibody is suitable for human use, e.g. in a medical treatment. Cancers that may be suitable for treatment are solid tumors. Said B7H4 expression, and T cell mediated killing, e.g. in cancer cells, may range in accordance with the invention from relatively low expression of B7H4, such as in MCF-7 cells, to relatively high expression of B7H4, such as in SK-BR3 cells, as shown e.g. in example 12. More preferably such bispecific antibodies have substitutions within the constant region that renders the Fc region, if present, inert.

In one embodiment, a bispecific antibody is provided comprising an antigen-binding region capable of binding to human B7H4 and an antigen-binding region that is capable of binding to CD3, such as human CD3ε (epsilon), wherein the antigen-binding region capable of binding to human B7H4 comprises a variable heavy chain (VH) region comprising the CDR1, CDR2 and CDR3 regions of SEQ ID NO. 25, 29 or 31, and a variable light chain region comprising the CDR1, CDR2 and CDR3 of SEQ ID NO. 33 and wherein the antigen-binding region that is capable of binding to CD3 comprises a heavy chain variable region (VH) comprising the CDR1, CDR2, and CDR3 sequences of 18, 19 and 21 respectively; and, a light chain variable region (VL) comprising the CDR1, CDR2, and CDR3 sequences of SEQ ID NO: 23, GTN and 24, respectively.

In another aspect, nucleic acids, such as DNA or RNA, are provided encoding antibodies as defined herein, as well as methods of producing the antibodies, or components thereof, as defined herein.

In a further aspect, said antibodies, or nucleic acids, in accordance with the invention are for use in a medical treatment.

C4-FEAR; II=bsIgG1-huCD3-FEALxB7H4-C3-FEAR; III=bsIgG1-huCD3-FEALxB7H4-C2-FEAR; IV=bsIgG1-huCD3-FEALxB7H4-C1-FEAR; V=IgG1-B7H3-BRCA84D.

Figure 1A:
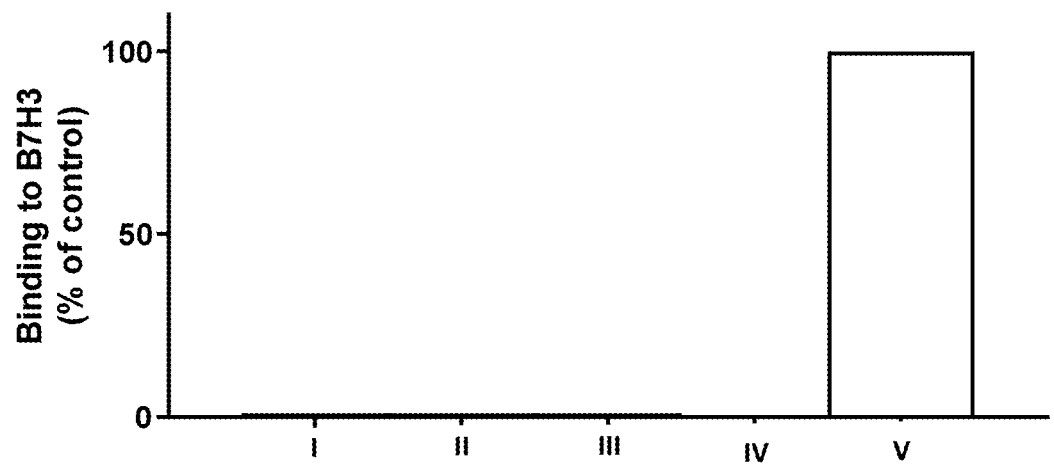
FIGS. 1A-1D. Determination of B7H4 domain involved in binding using B7H4-B7H3 chimeric molecules. The B7H4 domain specificity of the B7H4 antibodies was determined using a panel of cells transfected to express human B7H4 (FIG. 1A), human B7H4-B7H3 chimeric molecules B7H3-IgV/B7H4-IgC (FIG. 1B) or B7H4-IgV/B7H3-IgC (FIG. 1C), or human B7H3 (FIG. 1D). Binding was determined by flow cytometry. I=bsIgG1-huCD3-FEALxB7H4-
Figure 1B:
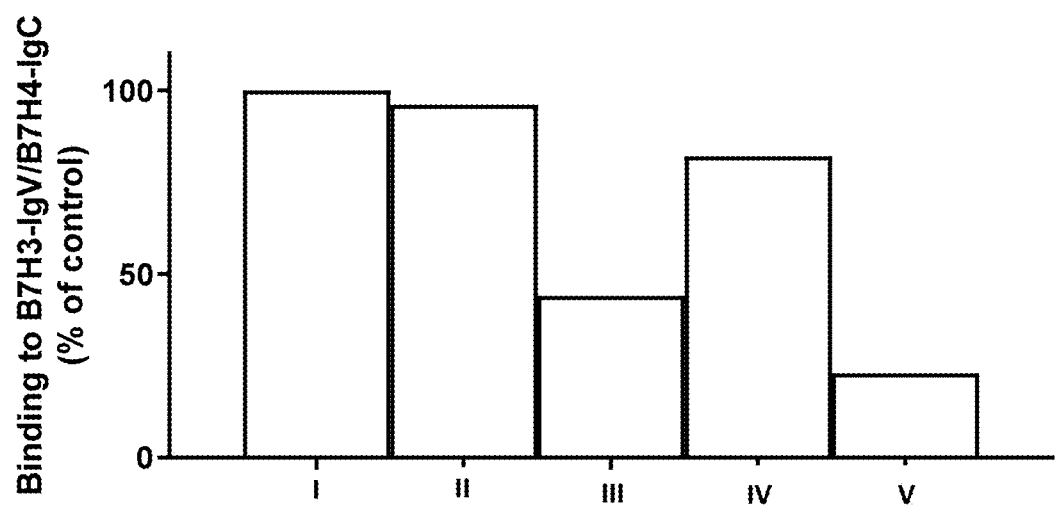
Figure 1C:
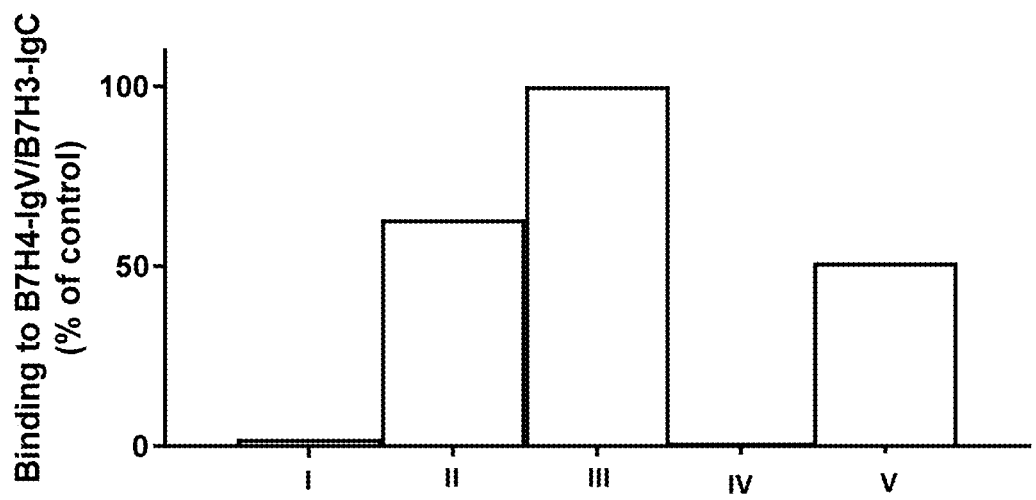
Figure 1D:
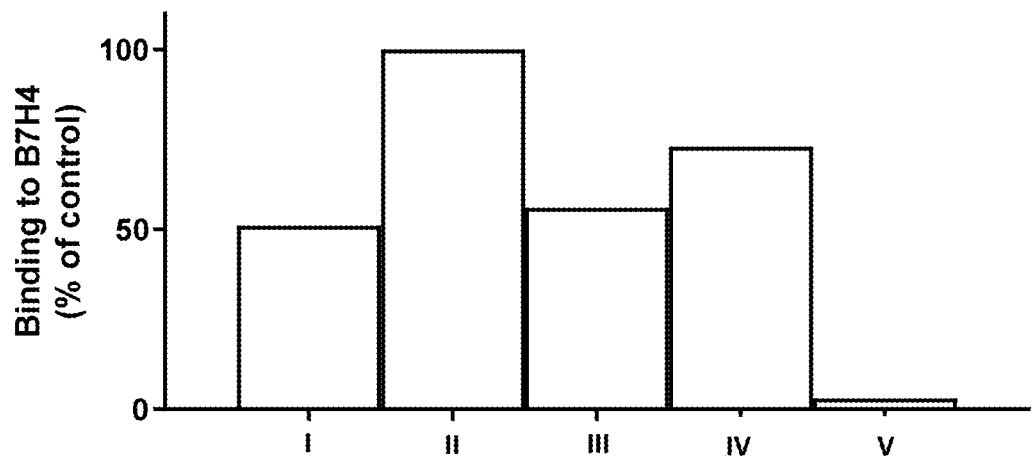
Figure 2:
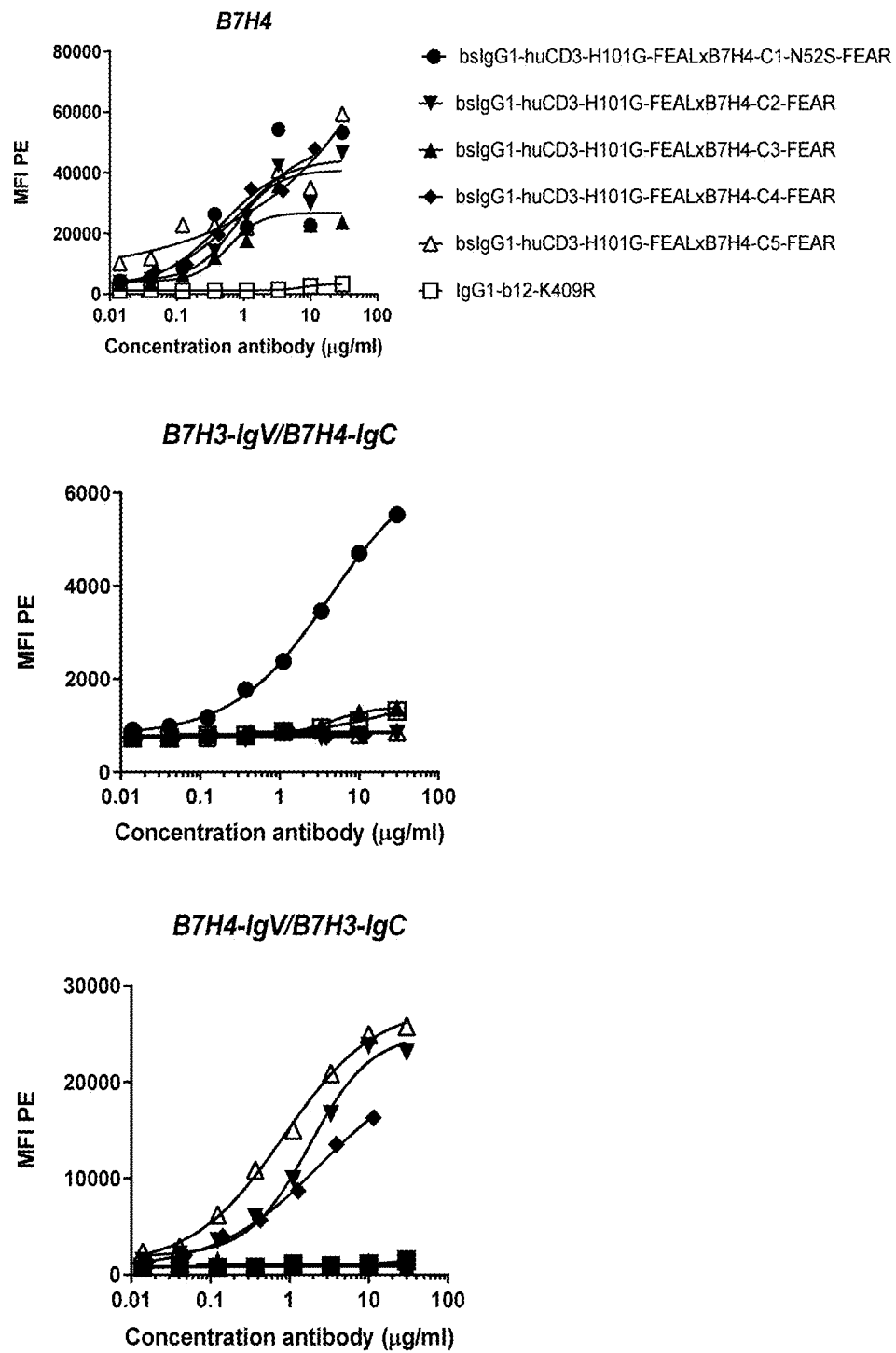

FIG. 2. Binding of B7H4 antibodies to B7H4, B7H3 or B7H4-B7H3 chimeric molecules. Binding of bsIgG1-huCD3-H101G-FEALxB7H4-C1-N52S-FEAR, bsIgG1-huCD3-H101G-FEALxB7H4-C2-FEAR, bsIgG1-huCD3-H101G-FEALxB7H4-C3-FEAR, bsIgG1-huCD3-H101G-FEALxB7H4-C4-FEAR and bsIgG1-huCD3-H101G-FEALxB7H4-C5-FEAR to HEK cells transiently transfected to express human B7H4 or the B7H4-B7H3 chimeric molecules B7H3-IgV/B7H4-IgC or B7H4-IgV/B7H3-IgC was assessed using flow cytometry.

Figure 3A:
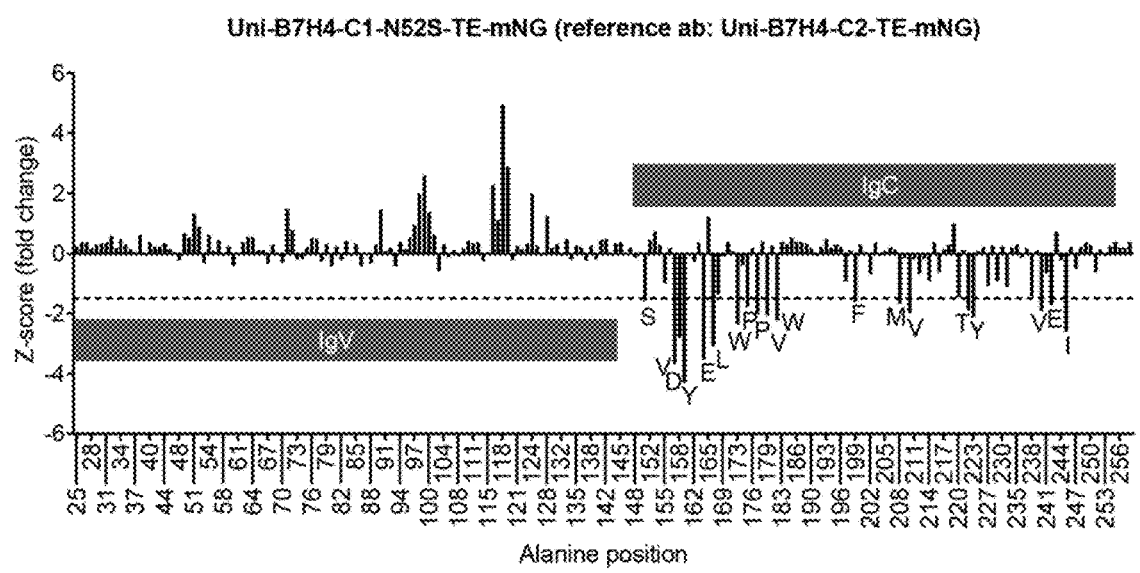
Figure 3B:
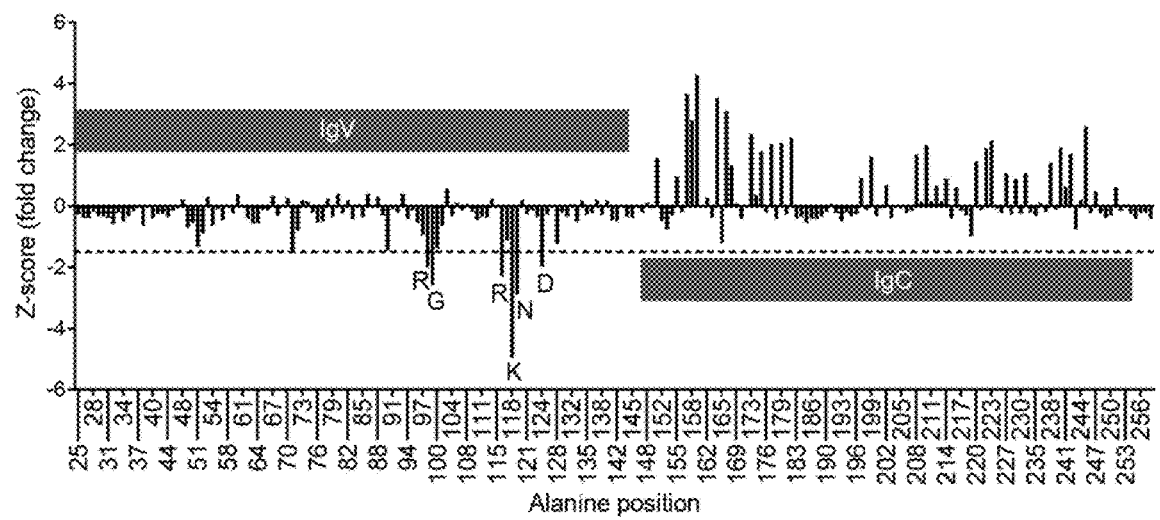
Figure 3C:
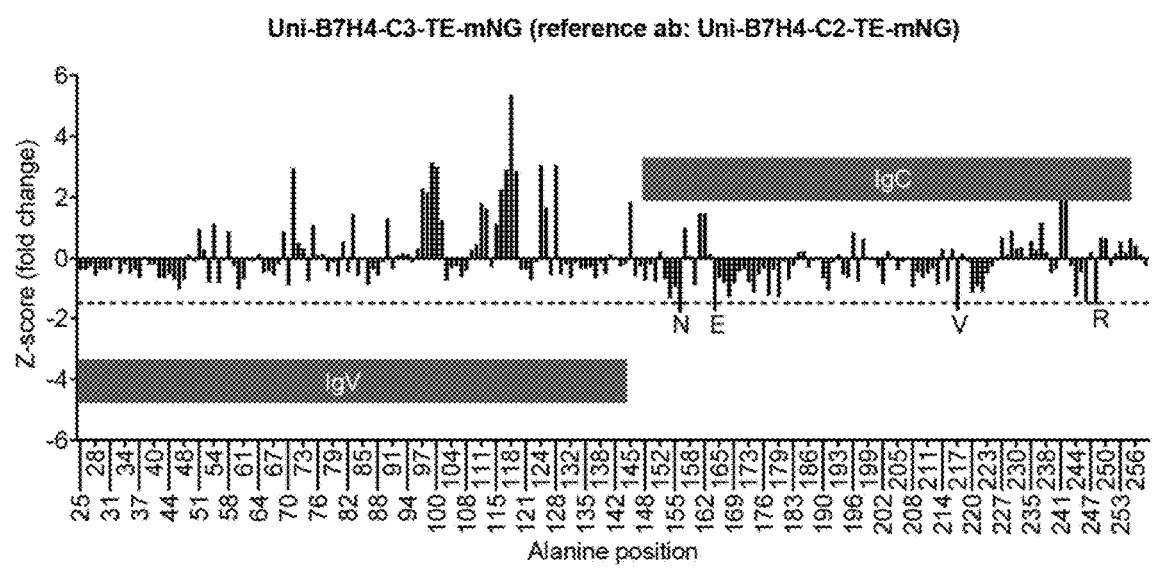

FIGS. 3A-3C. Binding of B7H4 antibodies to B7H4 variants with alanine mutations in the ECD. Binding was expressed as fold change compared to a reference antibody. Fold change was defined as Log 10(Normalized gMFI[ala mutant]/Normalized gMFI[wt]). Residues where the Fold Change in binding was lower than mean Fold Change—1.5×SD were considered 'loss of binding mutants'. Residues with a positive Fold Change in binding are loss of binding residues for the reference antibody. Numbers below the x-axis refer to amino acid positions. (FIG. 3A) Results for C1-N52S, with C2 as reference antibody. (FIG. 3B) Results for C2, with C1-N52S as reference antibody. (FIG. 3C) Results for C3, with C2 as reference antibody.

Figure 4:
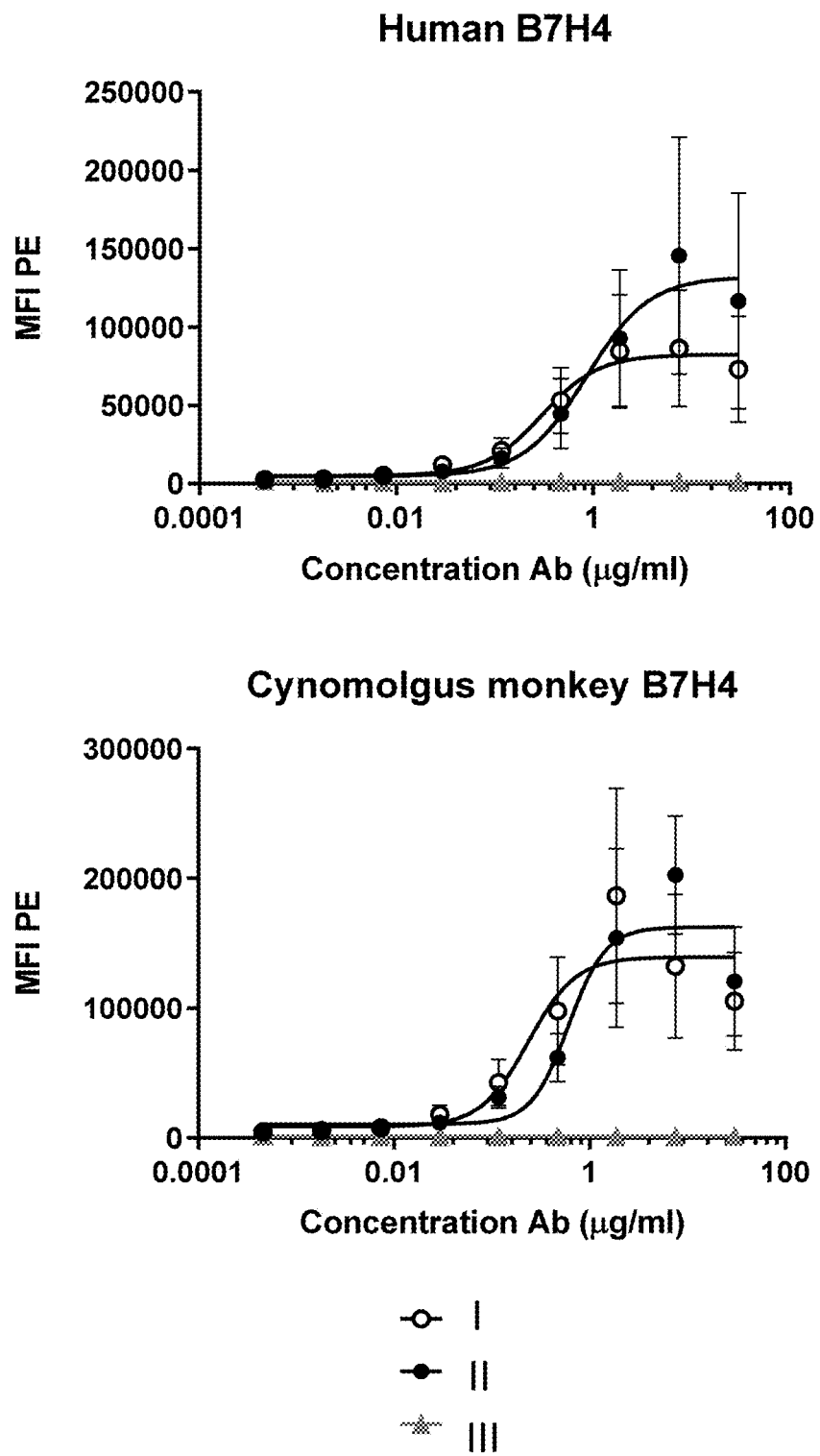

FIG. 4. Binding of B7H4 antibody and CD3xB7H4 bispecific antibody to human and cynomolgus monkey B7H4. Binding of IgG1-B7H4-C1-N52S-FEAR (I) and bsIgG1-huCD3-H101G-FEALxB7H4-C1-N52S-FEAR (II) to HEK-293F cells transiently transfected with human B7H4 or cynomolgus monkey B7H4 was determined by flow cytometry. Non-transfected HEK-293F cells (III) were used as negative control; for these binding of bsIgG1-huCD3-H101G-FEALxB7H4-C1-N52S-FEAR is shown.

Figure 5:
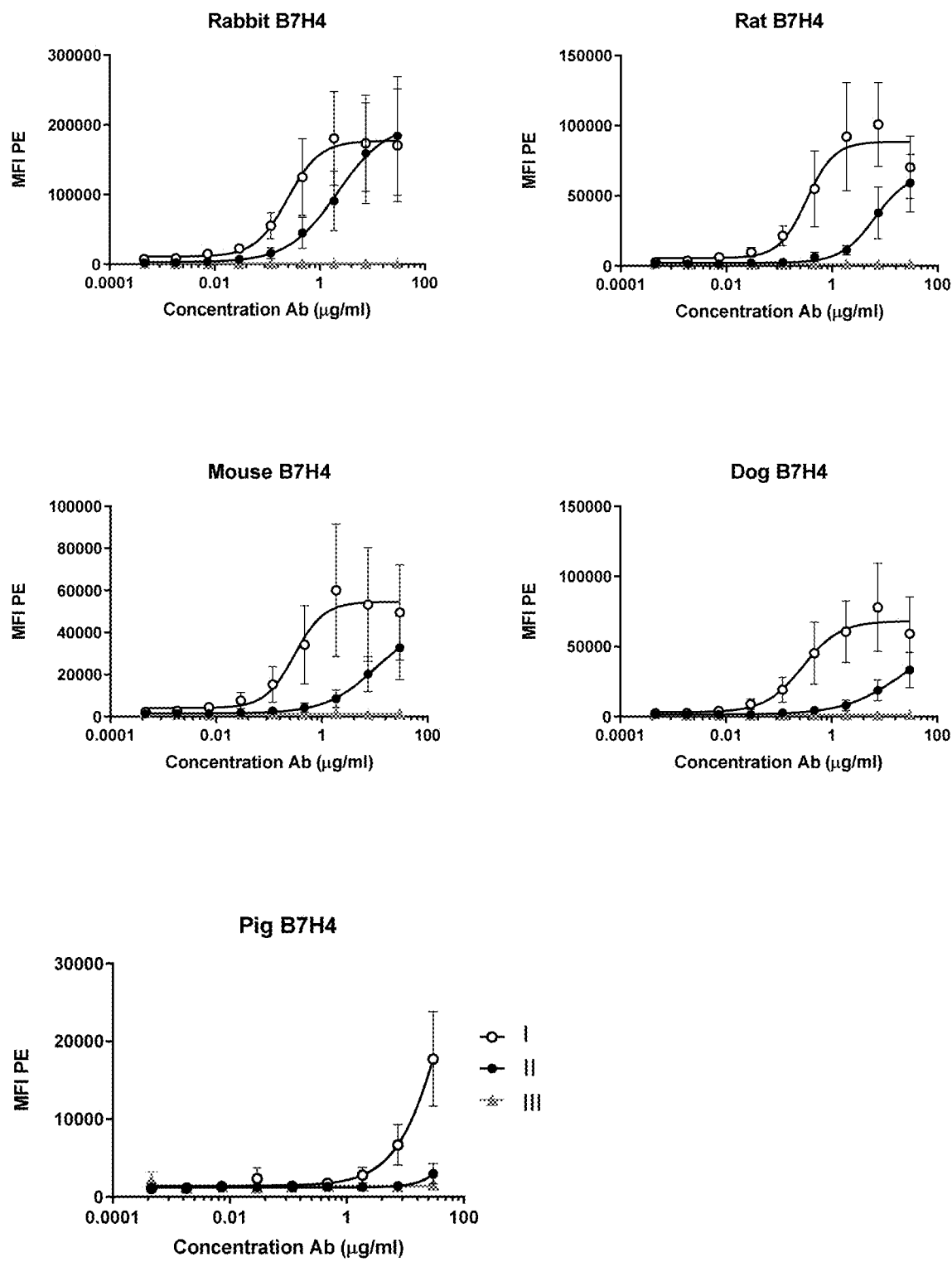

FIG. 5. Binding of B7H4 antibody and CD3xB7H4 bispecific antibody to B7H4 from rabbit, rat, mouse, dog and pig. Binding of IgG1-B7H4-C1-N52S-FEAR (I) and bsIgG1-huCD3-H101G-FEALxB7H4-C1-N52S-FEAR (II) to HEK-293F cells transiently transfected with B7H4 from rabbit, rat, mouse, dog or pig was determined by flow cytometry. Non-transfected HEK-293F cells (III) were used as negative control; for these binding of bsIgG1-huCD3-H101G-FEALxB7H4-C1-N52S-FEAR is shown.

Figure 6:
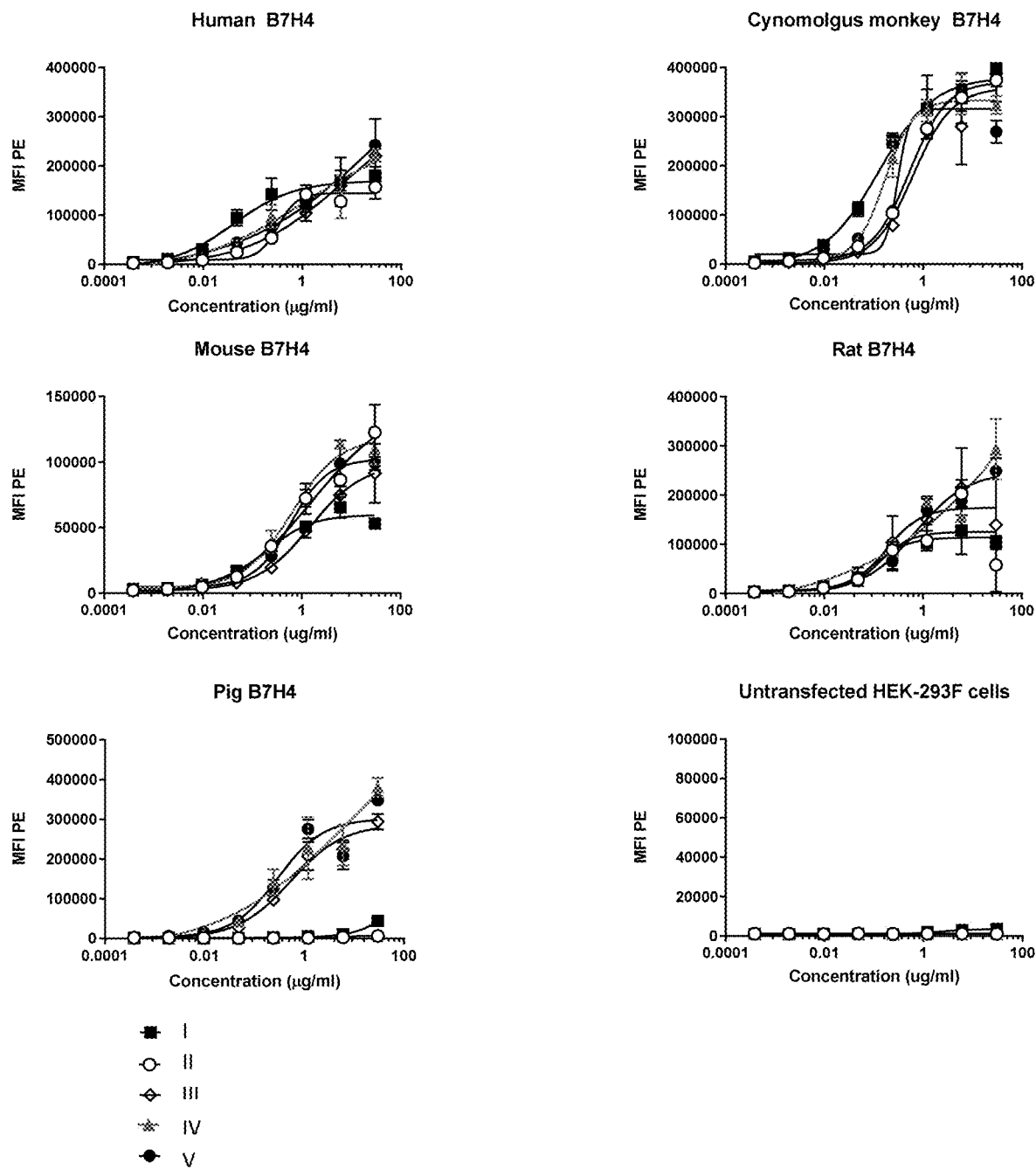

FIG. 6. Binding of B7H4 antibodies to HEK-293F cells transiently transfected with B7H4 from different species. Binding of IgG1-B7H4-C1-N52S-FEAR (I), IgG1-B7H4-C3-FEAR (II), IgG1-B7H4-C2-FEAR (III), IgG1-B7H4-C4-FEAR (IV), and IgG1-B7H4-C5-FEAR (V) to HEK-293F cells transfected with B7H4 from human, cynomolgus monkey, mouse, rat or pig, or to untransfected HEK-293F cells, was determined by flow cytometry. IgG1-b12 was used as non-binding control antibody (not shown).

Figure 7:
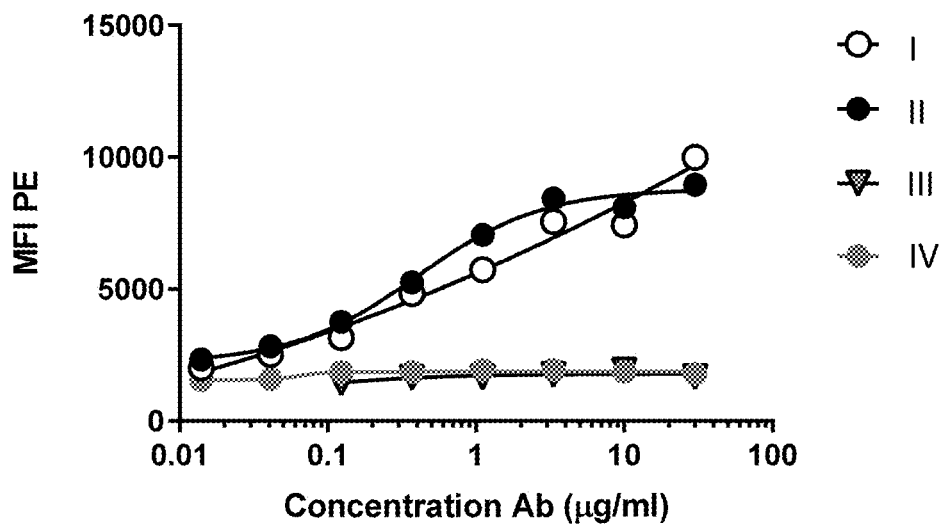
Figure 7:
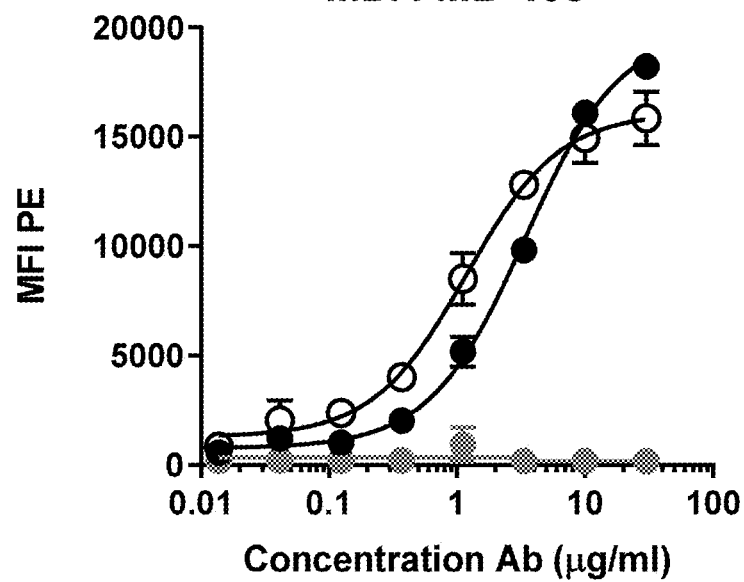

FIG. 7. Binding of IgG1-B7H4-C1-N52S-FEAR and bsIgG1-huCD3-H101G-FEALxB7H4-C1-N52S-FEAR to MCF-7 and MDA-MB-468 cells. Binding was determined by flow cytometry. I: IgG1-B7H4-C1-N52S-FEAR. II: bsIgG1-huCD3-H101G-FEALxB7H4-C1-N52S-FEAR. IgG1-b12 (III) and bsIgG1-huCD3-H101G-FEALxb12-FEAR (IV) were used as non-binding control antibodies.

Figure 8:
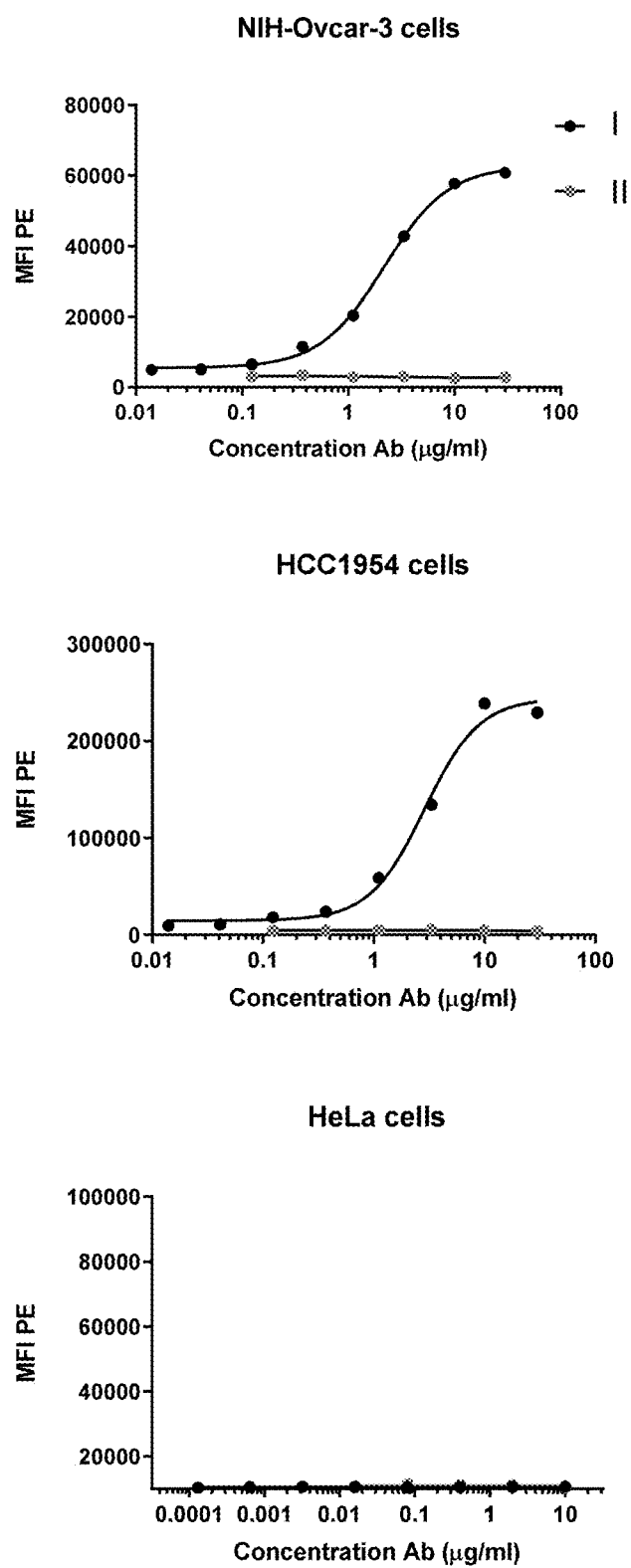

FIG. 8. Binding of bsIgG1-huCD3-H101G-FEALxB7H4-C1-N52S-FEAR to NIH-OVCAR-3, HCC1954 and HeLa cells. Binding was determined by flow cytometry. I: bsIgG1-huCD3-H101G-FEALxB7H4-C1-N52S-FEAR. BsIgG1-huCD3-H101G-FEALxb12-FEAR (II) was used as non-binding control antibody.

Figure 9:
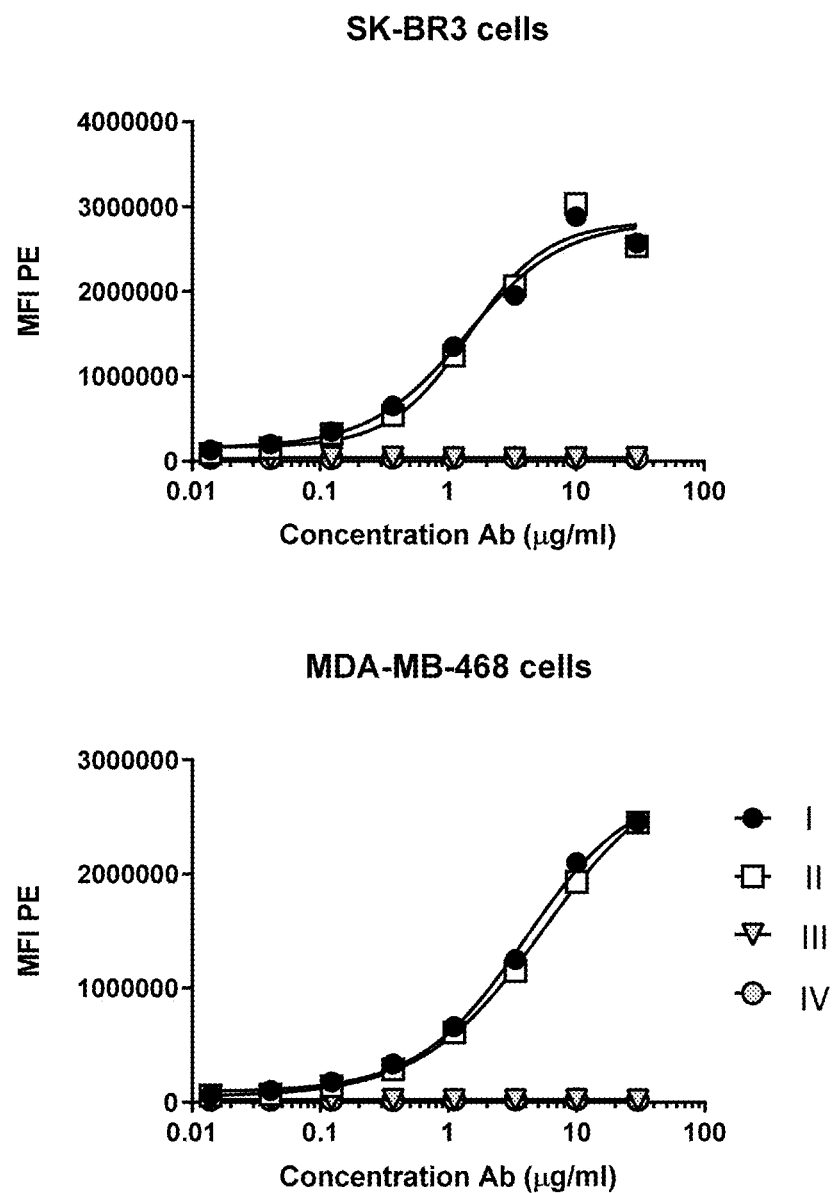

FIG. 9. Binding of bsIgG1-huCD3-H101G-FEALxB7H4-C1-N52S-FEAR and bsIgG1-huCD3-FEALxB7H4-C1-N52S-FEAR to SK-BR3 and MDA-MB-486 cells. Binding was determined by flow cytometry. I: bsIgG1-huCD3-H101G-FEALxB7H4-C1-N52S-FEAR. II: bsIgG1-huCD3-FEALxB7H4-C1-N52S-FEAR. bsIgG1-huCD3-FEALxb12-FEAR (III) and bsIgG1-huCD3-H101G-FEALxb12-FEAR (IV) were used as non-binding control antibodies.

Figure 10:
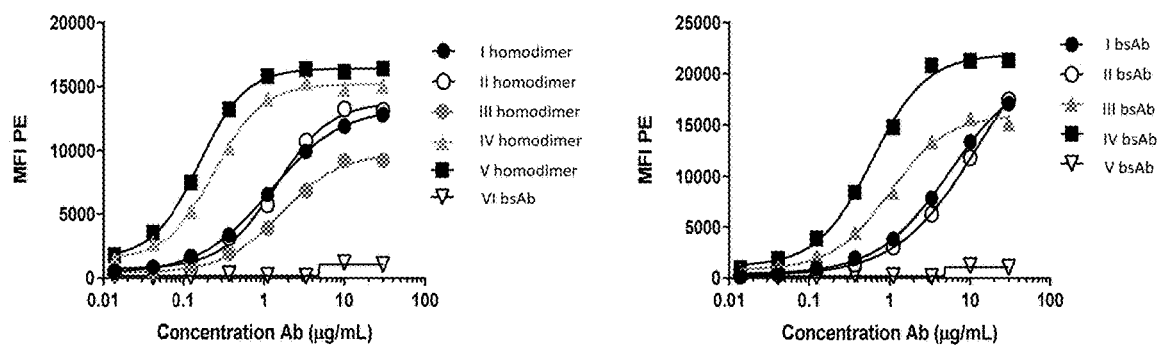
Figure 10:
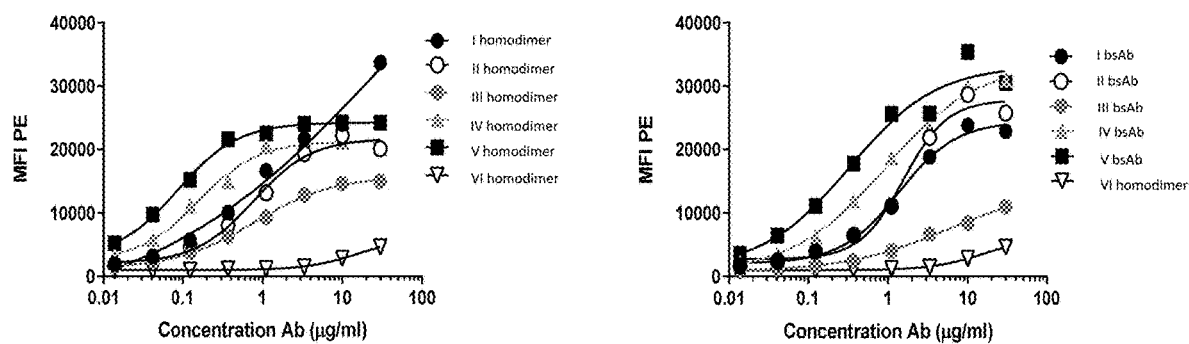

FIG. 10 Binding of various B7H4 antibodies in homodimer and bsAb format to MDA-MB-486 and HCC1954 cells. Binding of IgG1-B7H4-C1-N52S-FEAR (I homodimer), IgG1-B7H4-C2-FEAR (II homodimer), IgG1-B7H4-C3-FEAR (III homodimer), IgG1-B7H4-C4-FEAR (IV homodimer), IgG1-B7H4-C5-FEAR (V homodimer), bsIgG1-huCD3-H101G-FEALxB7H4-C1-N52S-FEAR (I bsAb), bsIgG1-huCD3-FEALxB7H4-C2-FEAR [MDA-MB-468] or bsIgG1-huCD3-H101G-FEALxB7H4-C2-FEAR [HCC1954] (II bsAb), bsIgG1-huCD3-H101G-FEALxB7H4-C3-FEAR (III bsAb), bsIgG1-huCD3-H101G-FEALxB7H4-C4-FEAR (IV bsAb), and bsIgG1-huCD3-H101G-FEALxB7H4-C5-FEAR (V bsAb) was determined by flow cytometry. bsIgG1-huCD3-H101G-FEALxb12-FEAR (VI bsAb) or IgG1-b12-K409R (VI homodimer) was used as a non-binding control antibody.

Figure 11:
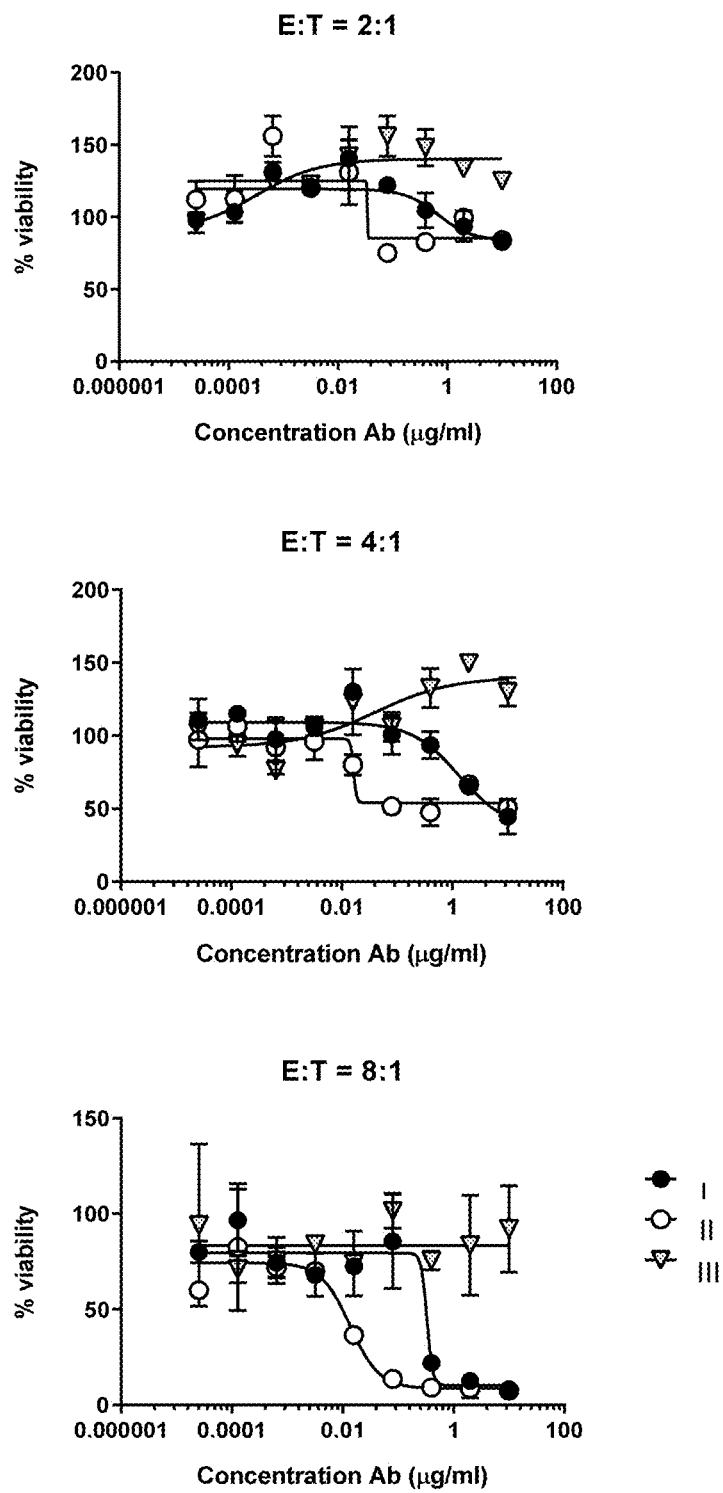

FIG. 11. Induction of T cell mediated cytotoxicity of SK-BR3 cells in vitro by CD3xB7H4 bispecific antibodies using purified T cells as effector cells at varying effector to target ratios (E:T). bsIgG1-huCD3-FEALxb12-FEAR was used as non-binding control antibody. I=bsIgG1-huCD3-H101G-FEALxB7H4-C1-N52S-FEAR; II=bsIgG1-huCD3-FEALxB7H4-C1-N52S-FEAR; III=bsIgG1-huCD3-FEALxb12-FEAR.

Figure 12:
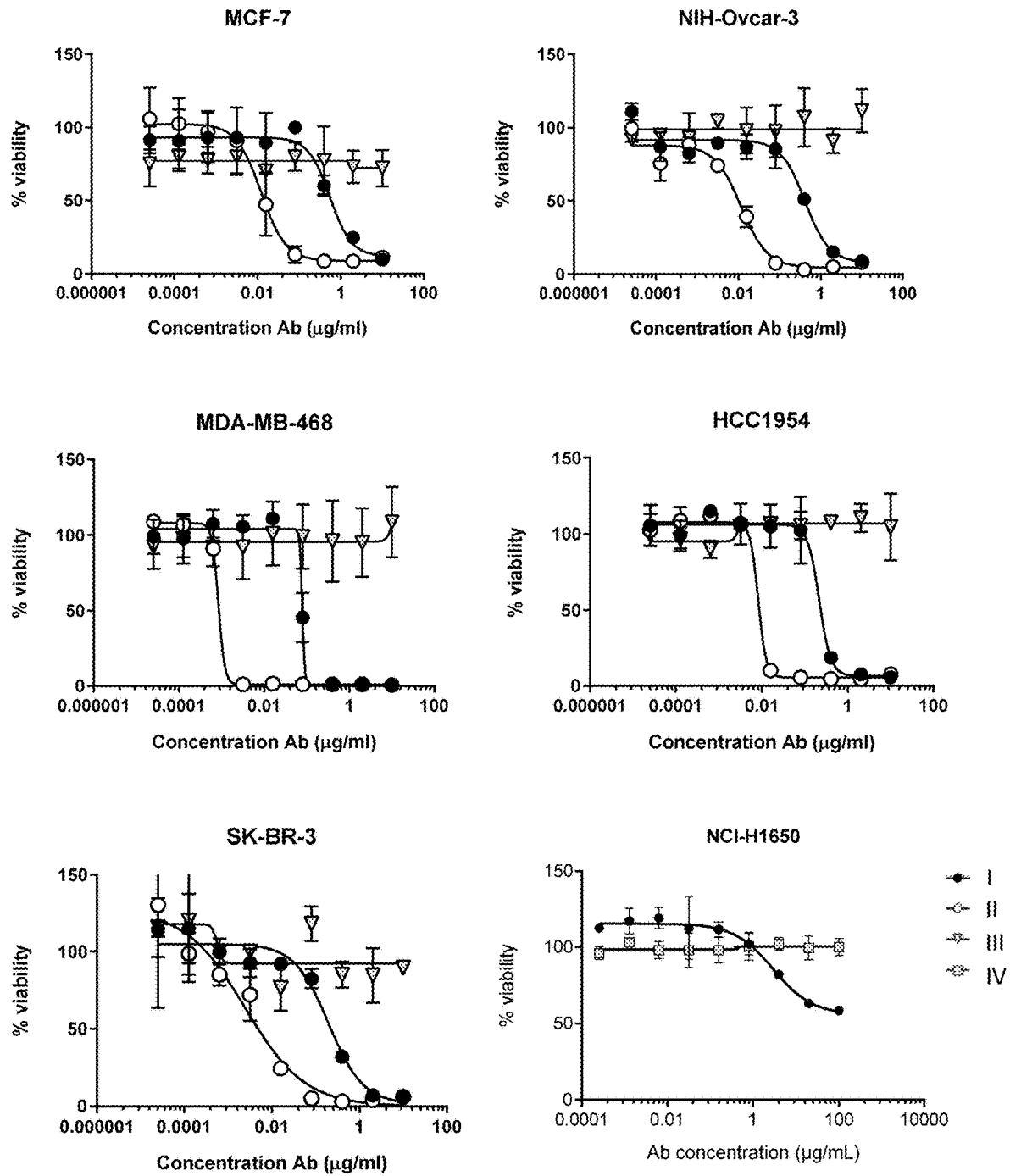

FIG. 12. Induction of T cell mediated cytotoxicity in various tumor cell lines in vitro in the presence of CD3xB7H4 bispecific antibodies with different CD3 arms. bsIgG1-huCD3-FEALxb12-FEAR was used as non-binding control antibody. I=bsIgG1-huCD3-H101G-FEALxB7H4-C1-N52S-FEAR; II=bsIgG1-huCD3-FEALxB7H4-C1-N52S-FEAR; III=bsIgG1-huCD3-FEALxb12-FEAR, IV=bsIgG1-huCD3-H101G-FEALxb12-FEAR.

Figure 13A:
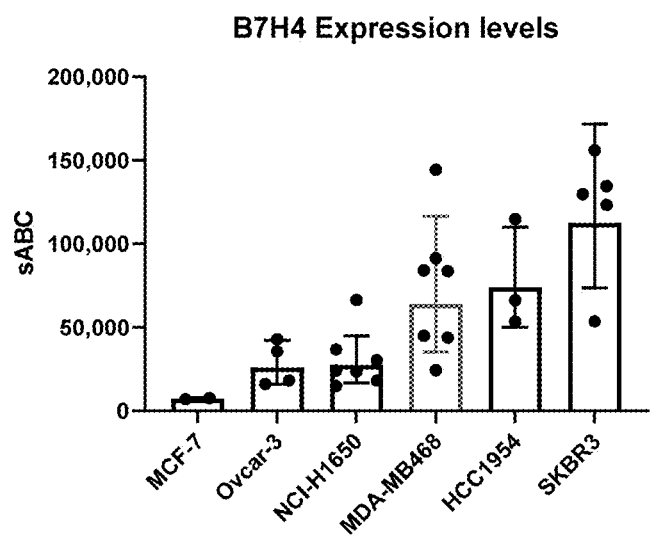
Figure 13B:
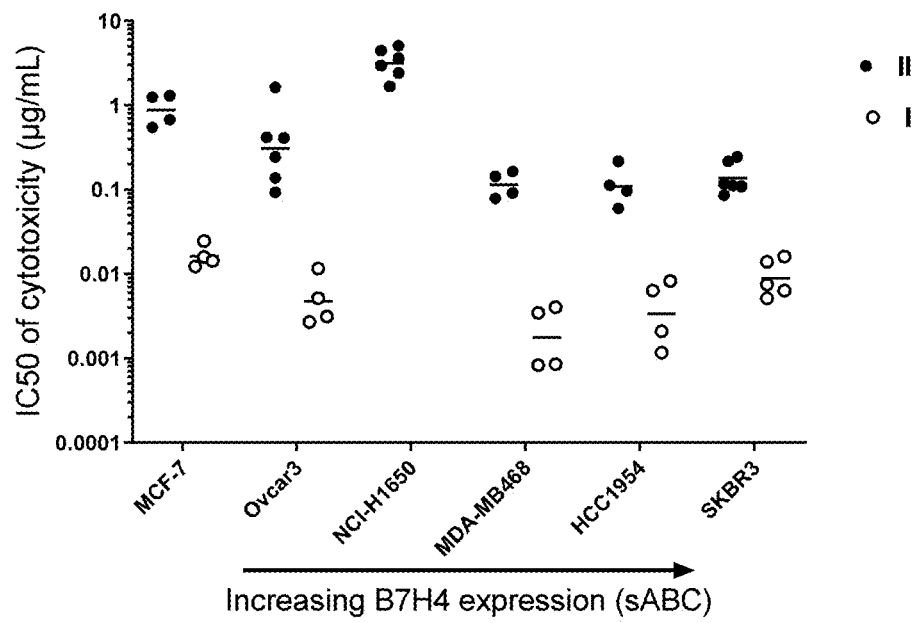

FIGS. 13A and 13B. B7H4 expression levels and IC50 of T cell-mediated tumor cell killing. (FIG. 13A) Quantitative flow cytometric analysis of B7H4 expression levels on tumor cell lines. Shown are individual measurements (dots), geometric means (bars) and standard deviation (error bars). sABC=specific antibody binding capacity. (FIG. 13B) IC50 of T cell-mediated tumor cell killing in the presence of bsIgG1-huCD3-FEALxB7H4-C1-N52S-FEAR (I) or bsIgG1-huCD3-H101G-FEALxB7H4-C1-N52S-FEAR (II) for the different tumor cell lines. Each dot represents an experiment performed with an individual T cell donor (4-6 donors per cell line), horizontal lines indicate median. Cell lines are ranked according to B7H4 expression level.

Figure 14A:
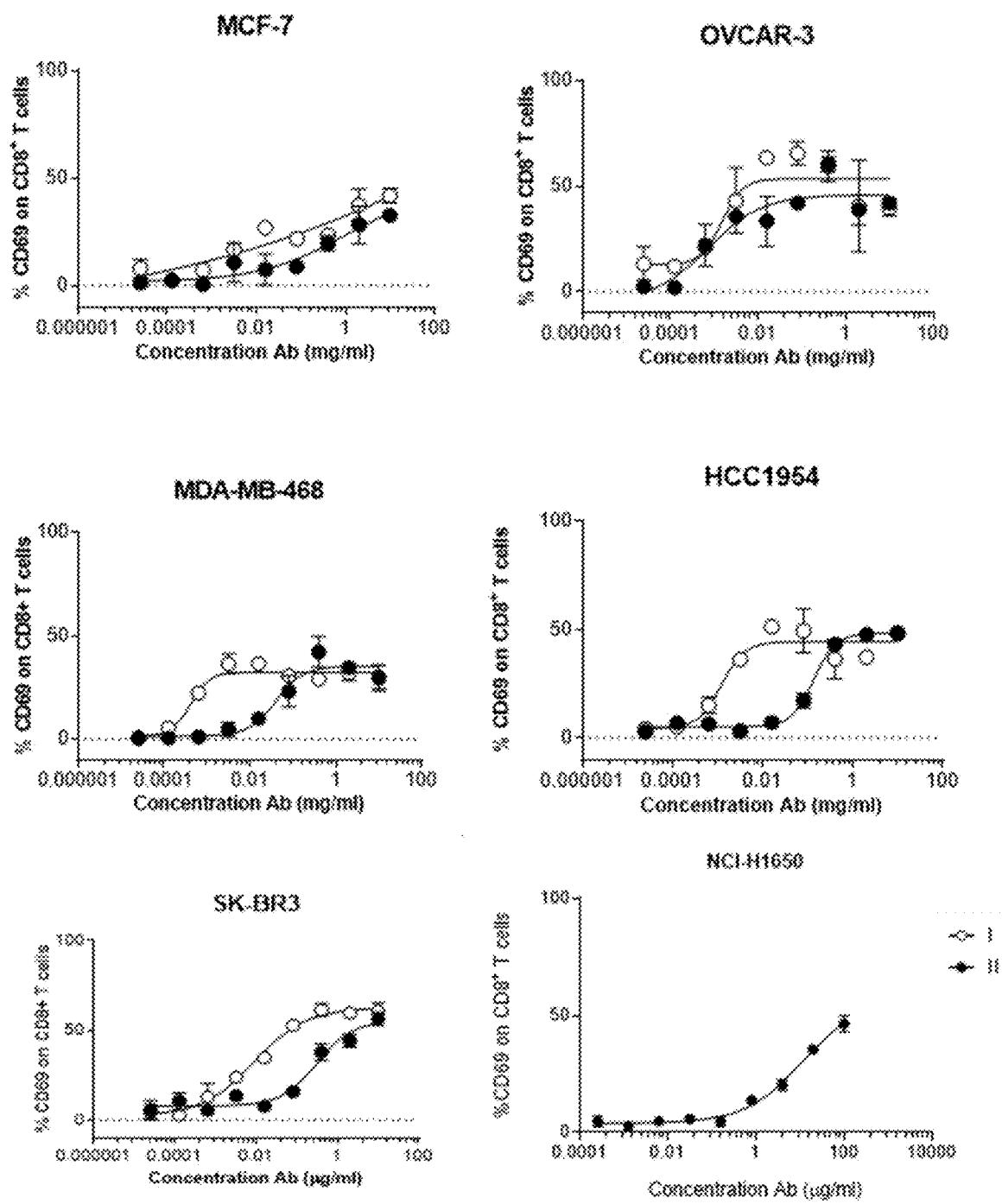
Figure 14B:
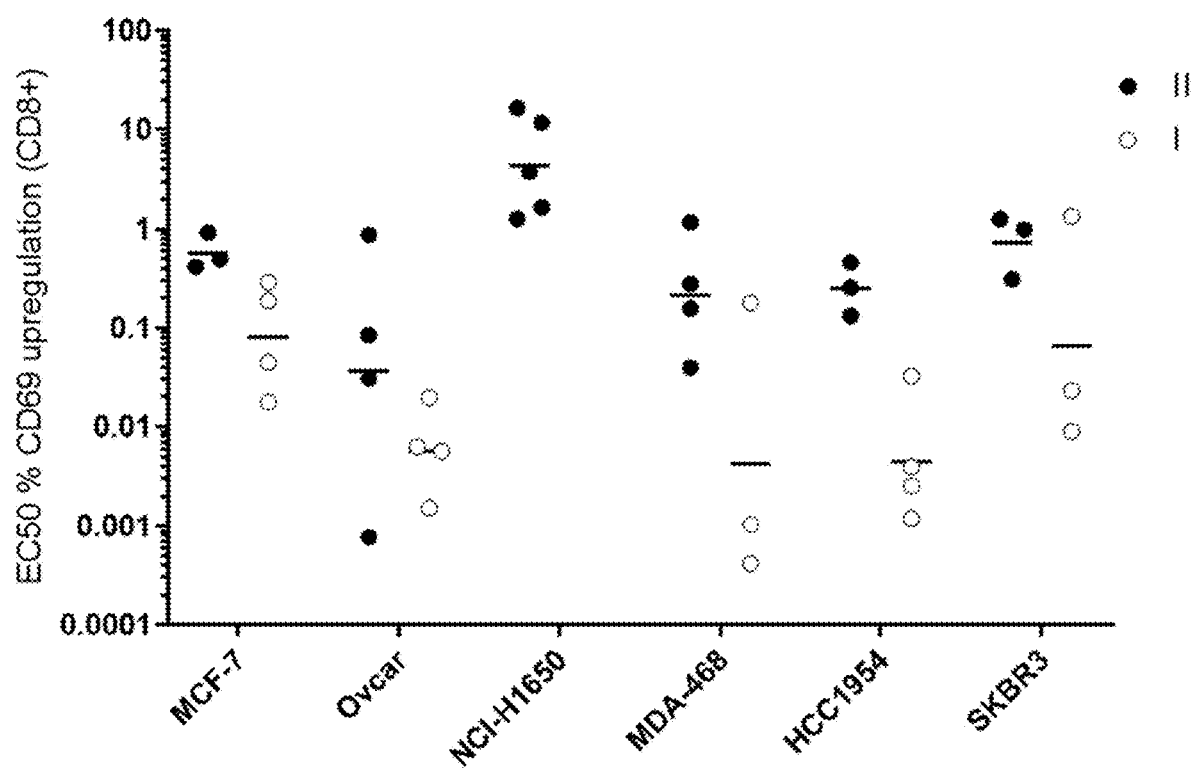

FIGS. 14A and 14B. T cell activation by B7H4 bispecific antibodies in T cell-tumor cell co-cultures. (FIG. 14A) T cell activation (% of CD69 on CD8+ cells) in the presence of bsIgG1-huCD3-FEALxB7H4-C1-N52S-FEAR (I) or bsIgG1-huCD3-H101G-FEALxB7H4-C1-N52S-FEAR (II) for various B7H4-positive tumor cell lines, determined by flow cytometry. (FIG. 14B) EC50 of T cell activation, using T cells derived from 3-5 donors, for each of the target cell lines. Each dot represents an experiment performed with an individual T cell donor; horizontal lines indicate geometric mean.

Figure 15:
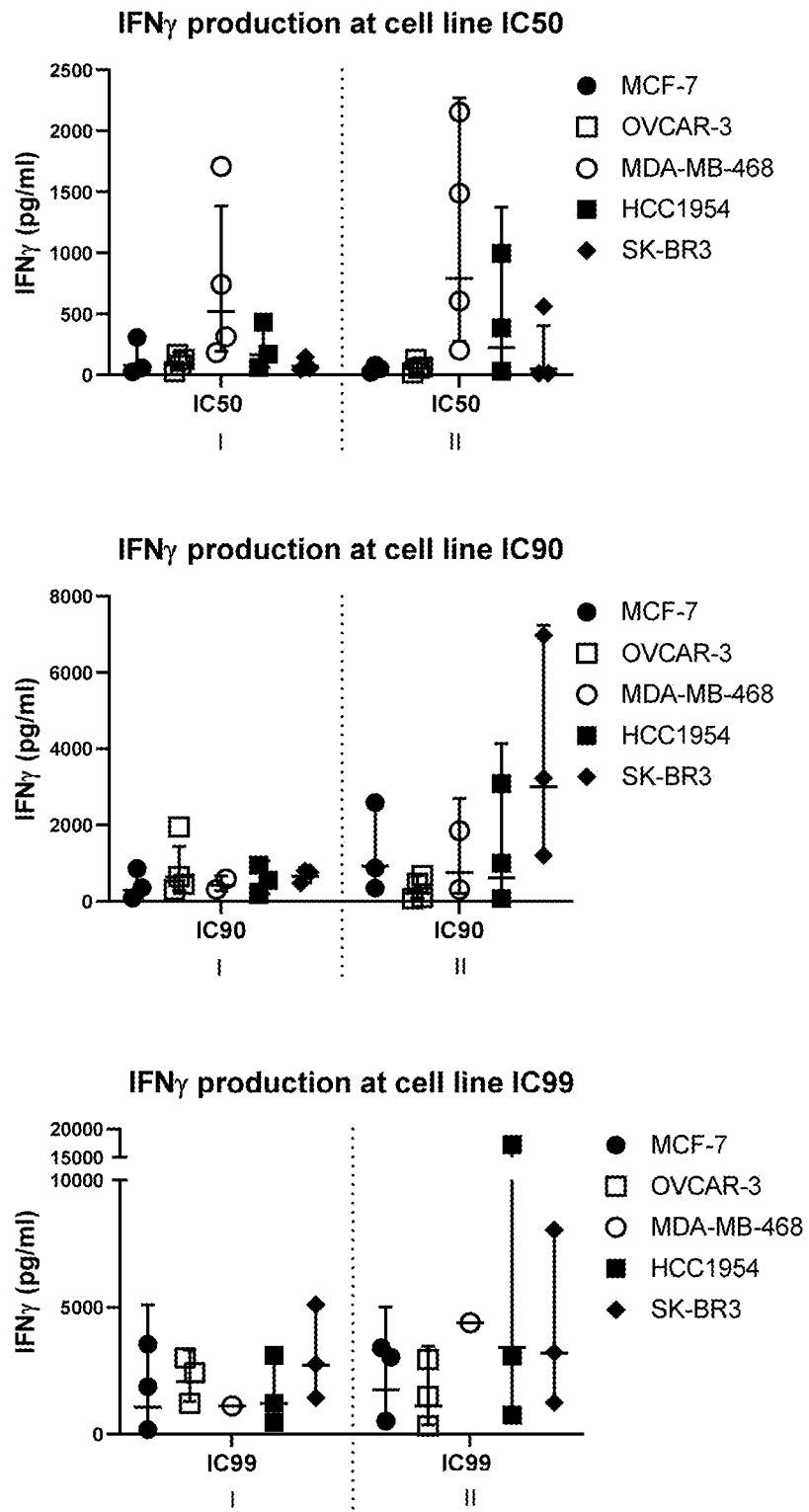

FIG. 15. IFNγ in the supernatant of T cell-tumor cell co-cultures at EC50, EC90 and EC99 for bsIgG1-huCD3-

H101G-FEALxB7H4-C1-N52S-FEAR and bsIgG1-huCD3-FEALxB7H4-C1-N52S-FEAR using T cells from 3-4 donors, determined by a multiplex U-plex assay. Shown are individual measurements (dots), geometric means (horizontal lines) and standard deviation (error bars). I: bsIgG1-huCD3-H101G-FEALxB7H4-C1-N52S-FEAR. II: bsIgG1-huCD3-FEALxB7H4-C1-N52S-FEAR.

Figure 16A:
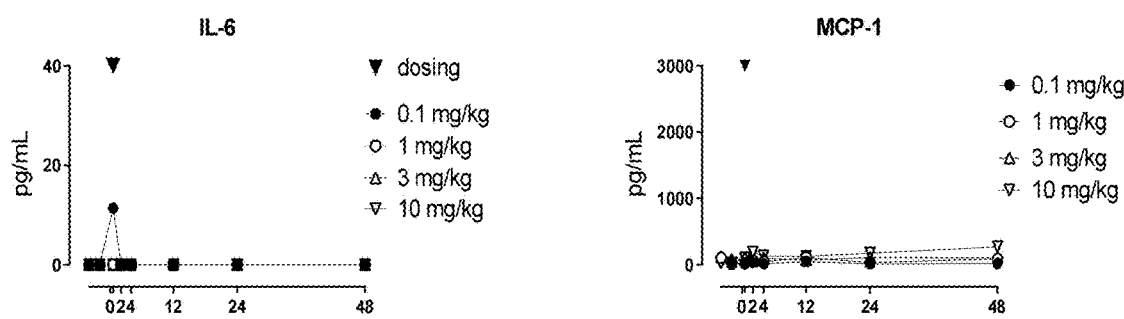
Figure 16B:
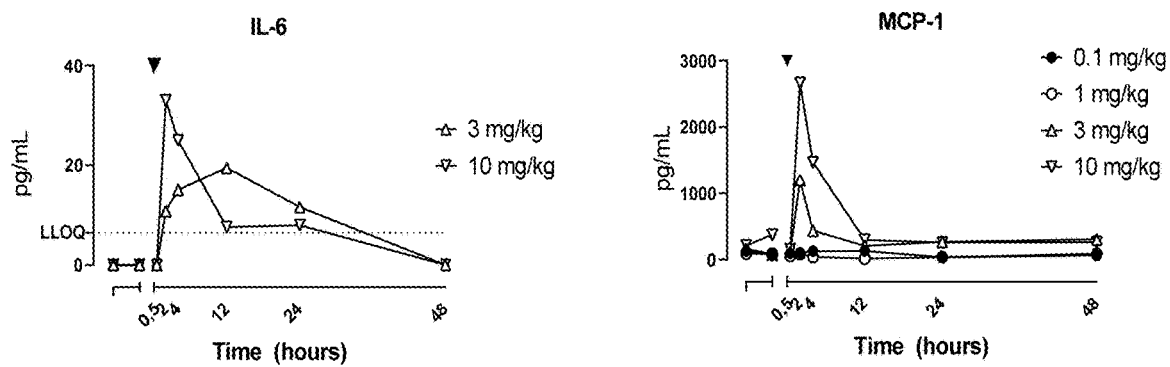

FIGS. 16A and 16B. IL-6 and MCP-1 levels in the plasma of cynomolgus monkeys treated with single dose IV infusion of bsIgG1-huCD3-H101G-FEALxB7H4-C1-N52S-FEAR (FIG. 16A) or bsIgG1-huCD3-FEALxB7H4-C1-N52S-FEAR (FIG. 16B).

Figure 17:
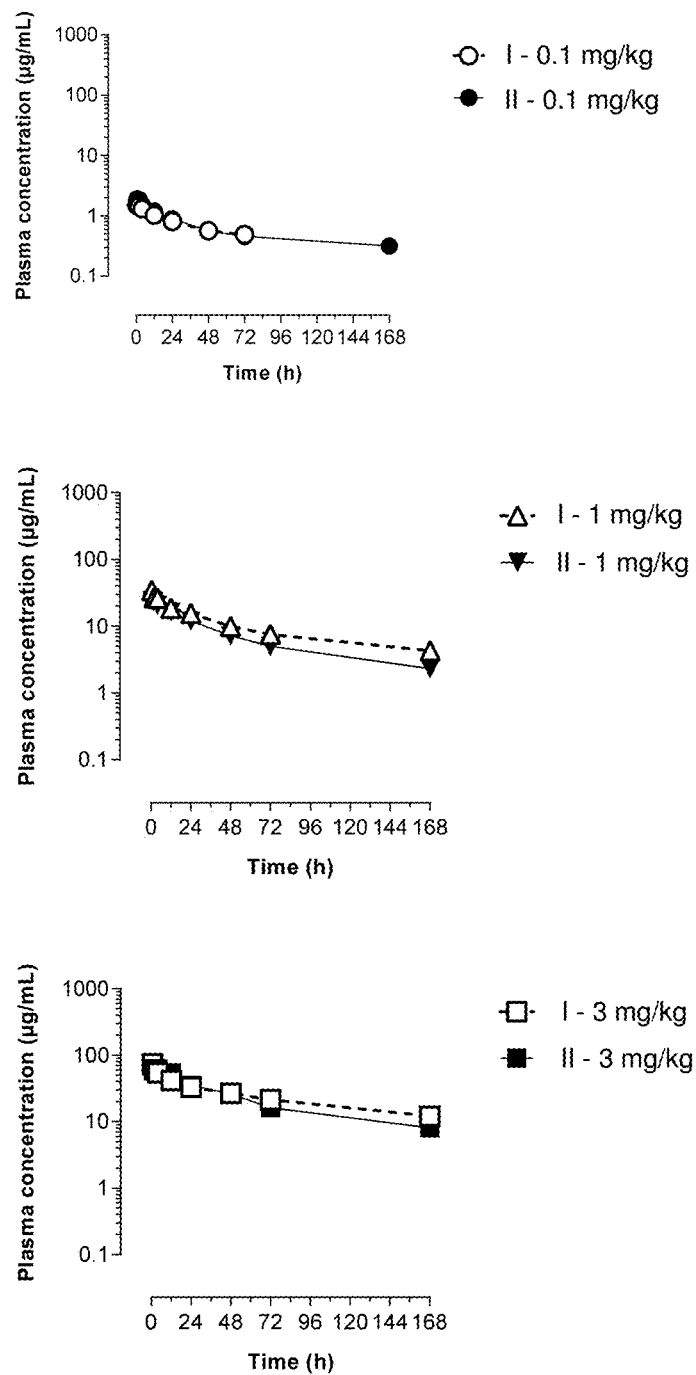
Figure 17:
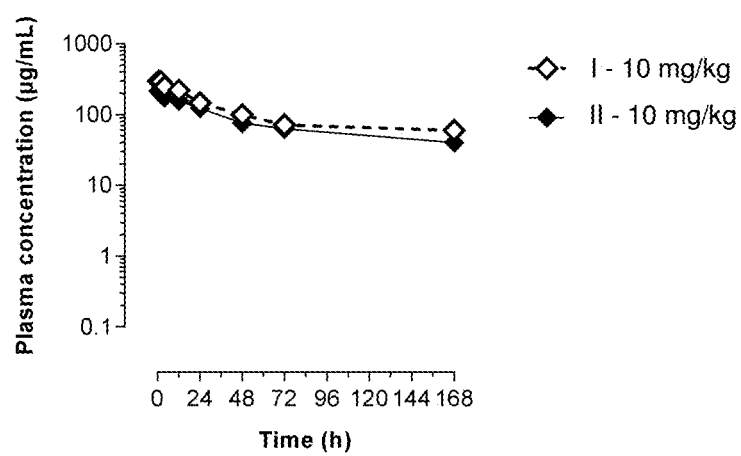

FIG. 17. Mean plasma concentration-time profiles following a single IV infusion of bsIgG1-huCD3-H101G-FEALxB7H4-C1-N52S-FEAR or bsIgG1-huCD3-FEALxB7H4-C1-N52S-FEAR. I: bsIgG1-huCD3-H101G-FEALxB7H4-C1-N52S-FEAR. II: bsIgG1-huCD3-FEALxB7H4-C1-N52S-FEAR.

Figure 18:
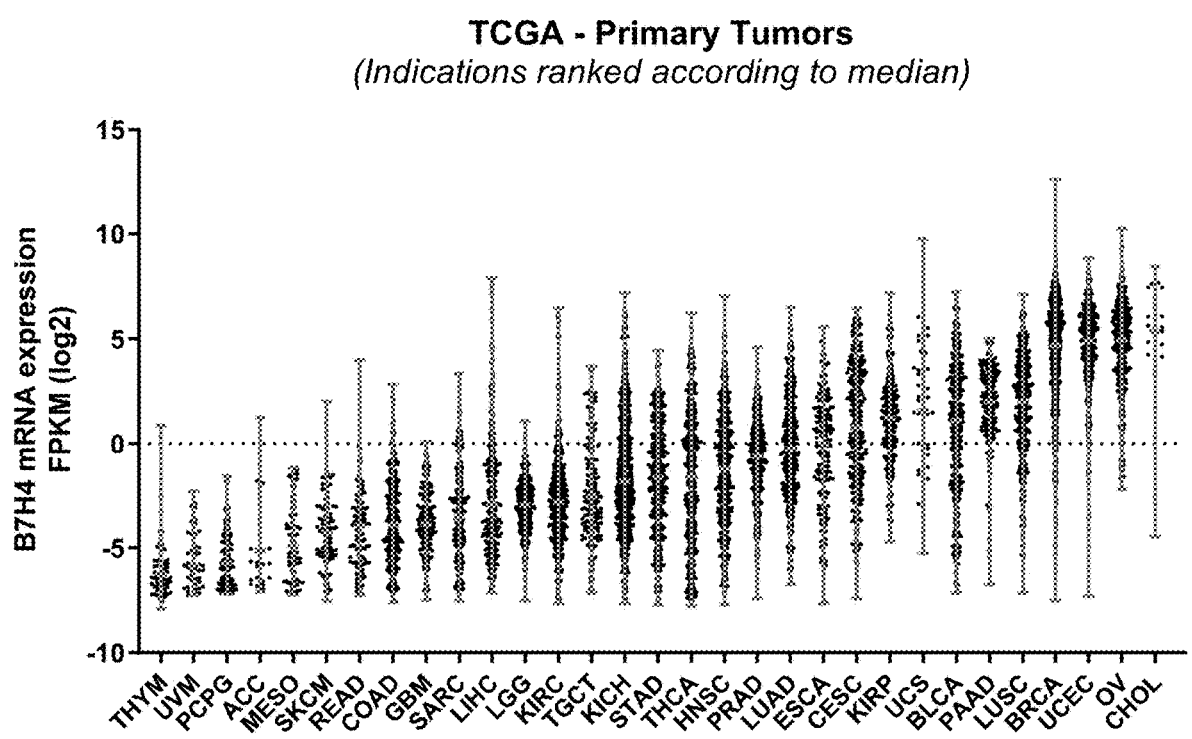

FIG. 18. B7H4 mRNA expression levels in a range of primary solid tumors. B7H4 mRNA levels were extracted from the Omicsoft TCGA database and visualized using Oncoland software. Indications are ranked according to median of the B7H4 mRNA expression. THYM=thymoma, UVM=uveal melanoma, PCPG=pheochromocytoma and paraganglioma, ACC=adrenocortical carcinoma, MESO=mesothelioma, SKCM=skin cutaneous melanoma, READ=rectum adenocarcinoma, COAD=colon adenocarcinoma, GMB=glioblastoma multiforme, SARC=sarcoma, LIHC=liver hepatocellular carcinoma, LGG=brain lower grade glioma, KIRC=kidney renal clear cell carcinoma, TGCT=testicular germ cell tumors, KICH=kidney chromophobe, STAD=stomach adenocarcinoma, THCA=thyroid carcinoma, HNSC=head and neck squamous cell carcinoma, PRAD=prostate adenocarcinoma, LUAD=lung adenocarcinoma, ESCA=esophageal carcinoma, CESC=cervical squamous cell carcinoma and endocervical adenocarcinoma, KIRP=kidney renal papillary cell carcinoma, UCS=uterine carcinosarcoma, BLCA=bladder urothelial carcinoma, PAAD=pancreatic adenocarcinoma, LUSC=lung squamous cell carcinoma, BRCA=breast invasive carcinoma, UCEC=uterine corpus endometrial carcinoma, OV=ovarian serous cystadenocarcinoma and CHOL=cholangiocarcinoma.

TABLE 1

Amino acid and nucleic acid sequence

| SEQ ID NO: | Reference | Domain | Sequence |
| --- | --- | --- | --- |
| 1 | Human B7H4 | ORF | MASLGQILFWSIISIIILAGAIALIIGFGISGRHSITVTTVAS AGNIGEDGILSCTFEPDIKLSDIVIQWLKEGVLGLVHEFK EGKDELSEQDEMFRGRTAVFADQVIVGNASLRLKNVQ LTDAGTYKCYIITSKGKGNANLEYKTGAFSMPEVNVDY NASSETLRCEAPRWFPQPTVVWASQVDQGANFSEVS NTSFELNSENVTMKVVSVLYNVTINNTYSCMIENDIAK ATGDIKVTESEIKRRSHLQLLNSKASLCVSSFFAISWALLP LSPYLMLK |
| 2 | Macaca fascicularis B7H4 transcript 1 | ORF | MASLGQILFWSIISIIFILAGAIALIIGFGISGRHSITVTTVA SAGNIGEDGILSCTFEPDIKLSDIVIQWLKEGVIGLVHEF KEGKDELSEQDEMFRGRTAVFADQVIVGNASLRLKNV QLTDAGTYKCYIITSKGKGNANLEYKTGAFSMPEVNVD YNASSETLRCEAPRWFPQPTVVWASQVDQGANFSEV SNTSFELNSENVTMKVVSVLYNVTINNTYSCMIENDIAK ATGDIKVTESEIKRRSHLQLLNSKASLCVSSFLAISWALLP LAPYLMLK |
| 3 | Canis familiaris B7H4 | ORF | MASPGQNIFWSIISVIILAGAIALIIGFGISGRHSITVTTLT SAGNIGEDGILSCTFEPDIKLSDIVIQWLKEGVMGLVHE FKEGKDDLSDQDEMFRGRTAVFADQVIGGNASLRLKN VQLTDAGTYKCYIITSKGKGNANLEYKTGAFSIPEVNVD YNASSENLRCEAPRWFPQPTVVWASQADQGANFSEV FNTSFELNSENVTMKVVSVLYNVTINNTYSCMIENDIAK ATGDIKVTDSEIKRRSHLQLLNSKASLGVSSFFAISWVLL PLSSYLMLK |
| 4 | Oryctolagus cuniculus B7H4 | ORF | MASLGQIIFWSIISIIILAGAIALIIGFGISGRHSITVTTLTS AGNIGEDGILSCTFEPDIRLSDIVIQWLKEGVVGLVHEFK EGKDDLSDQDEMFRGRTAVFTDQVIVGNASLRLKNVQ LTDAGTYKCYIITSKGKGNANLEYKTGAFSMPEVNLDY NASSESLRCEAPRWFPQPTVVWASQVDQGANFSEVS NTSFELNSENVTMKVVSVLYNVTVNNTYSCMIENDIAK ATGDIKVTDSEIKRRSSLQLLNSRAAPSVSPRSAVGWLL LPLSSYVMLK |
| 5 | Rattus norvegicus B7H4 | ORF | MASLGQIIFWSIINVIIILAGAIVLIIGFGISGKHFITVTTFT SAGNIGEDGTLSCTFEPDIKLNGIVIQWLKEGIKGLVHEF KEGKDDLSQQHEMFRGRTAVFADQVVVGNASLRLKN VQLTDAGTYTCYIHTSKGKGNANLEYKTGAFSMPEINV DYNASSESLRCEAPRWFPQPTVAWASQVDQGANFSE VSNTSFELNSENVTMKVVSVLYNVTINNTYSCMIENDIA KATGDIKVTDSEVKRRSQLELLNSGPSPCVSSVSAAGW ALLSLSCCLMLR |

TABLE 1-continued

Amino acid and nucleic acid sequence

| SEQ ID NO: | Reference | Domain | Sequence |
|---|---|---|---|
| 6 | *Mus musculus* B7H4 | ORF | MASLGQIIFWSIINIIIILAGAIALIIGFGISGKHFITVTTFTS AGNIGEDGTLSCTFEPDIKLNGIVIQWLKEGIKGLVHEFK EGKDDLSQQHEMFRGRTAVFADQVVVGNASLRLKNV QLTDAGTYTCYIRTSKGKGNANLEYKTGAFSMPEINVD YNASSESLRCEAPRWFPQPTVAWASQVDQGANFSEV SNTSFELNSENVTMKVVSVLYNVTINNTYSCMIENDIAK ATGDIKVTDSEVKRRSQLQLLNSGPSPCVFSSAFVAGW ALLSLSCCLMLR |
| 7 | *Sus scrofa* B7H4 | ORF | MASLGQVVFWSIISIIIILAGAIAFIIGFGISGRHSITVTTLT SAGNIGEDGILSCTFEPDIKLSDIVIQWLKEGVTGLVHEF KKGKDDLSDQDEMFRGRTAVFADQVIVGNASLRLKNV QLTDAGTYKCYIITSKGKGNAKLEYKTGAFSIPEVNVDS NASSESLRCEAPRWFPQPTVVWASQVDQGANFSEVS NTSFELNPENVTMKVVSVLYNVTINTTYSCMIENDIAKA TGDIRVTDSEIKRQSHLQLLNSKASLCLSSFVAISWVLLP LCPYLMLK |
| 8 | Kozak |  | GCCGCCACC |
| 9 | B7H3 | ORF | MLRRRGSPGMGVHVGAALGALWFCLTGALEVQVPED PVVALVGTDATLCCSFSPEPGFSLAQLNLIWQLTDTKQL VHSFAEGQDQGSAYANRTALFPDLLAQGNASLRLQRV RVADEGSFTCFVSIRDFGSAAVSLQVAAPYSKPSMTLEP NKDLRPGDIVTITCSSYQGYPEAEVFWQDGQGVPLTG NVTTSQMANEQGLFDVHSILRVVLGANGTYSCLVRNP VLQQDAHSSVTITPQRSPTGAVEVQVPEDPVVALVGT DATLRCSFSPEPGFSLAQLNLIWQLTDTKQLVHSFTEGR DQGSAYANRTALFPDLLAQGNASLRLQRVRVADEGSF TCFVSIRDFGSAAVSLQVAAPYSKPSMTLEPNKDLRPG DTVTITCSSYRGYPEAEVFWQDGQGVPLTGNVTTSQM ANEQGLFDVHSVLRVVLGANGTYSCLVRNPVLQQDAH GSVTITGQPMTFPPEALWVTVGLSVCLIALLVALAFVC WRKIKQSCEEENAGAEDQDGEGEGSKTALQPLKHSDS KEDDGQEIA |
| 10 | B7H4-IgV/B7H3-IgC | ORF | MASLGQILFWSIISIIIILAGAIALIIGFGISGRHSITVTTVAS AGNIGEDGILSCTFEPDIKLSDIVIQWLKEGVLGLVHEFK EGKDELSEQDEMFRGRTAVFADQVIVGNASLRLKNVQ LTDAGTYKCYIITSKGKGNANLEYKTGAPYSKPSMTLEP NKDLRPGDIVTITCSSYRGYPEAEVFWQDGQGVPLTG NVTTSQMANEQGLFDVHSVLRVVLGANGTYSCLVRNP VLQQDAHGSVTITGQPMTFPPEALWVTVGLSVCLIALL VALAFVCWRKIKQSCEEENAGAEDQDGEGEGSKTALQ PLKHSDSKEDDGQEIA |
| 11 | B7H3-IgV/B7H4-IgC | ORF | MLRRRGSPGMGVHVGAALGALWFCLTGALEVQVPED PVVALVGTDATLCCSFSPEPGFSLAQLNLIWQLTDTKQL VHSFAEGQDQGSAYANRTALFPDLLAQGNASLRLQRV RVADEGSFTCFVSIRDFGSAAVSLQVAAFSMPEVNVDY NASSETLRCEAPRWFPQPTVVWASQVDQGANFSEVS NTSFELNSENVTMKVVSVLYNVTINNTYSCMIENDIAK ATGDIKVTESEIKRRSHLQLLNSKASLCVSSFFAISWALLP LSPYLMLK |
| 12 | B7H4ECD-FcHisC | Mature protein | LIIGFGISGRHSITVTTVASAGNIGEDGILSCTFEPDIKLSD IVIQWLKEGVLGLVHEFKEGKDELSEQDEMFRGRTAVF ADQVIVGNASLRLKNVQLTDAGTYKCYIITSKGKGNAN LEYKTGAFSMPEVNVDYNASSETLRCEAPRWFPQPTV VWASQVDQGANFSEVSNTSFELNSENVTMKVVSVLY NVTINNTYSCMIENDIAKATGDIKVTESEIKRRSHLQLLN SKASIEGRMDPKSCDKTHTCPPCPAPEAEGAPSVFLFPP KPKDTLMISRTPEVTCVVVDVSHEDPEVKFNWYVDGV EVHNAKTKPREEQYNSTYRVVSVLTVLHQDWLNGKEY KCKVSNKALPAPIEKTISKAKGQPREPQVYTLPPSREEM TKNQVSLTCLVKGFYPSDIAVEWESNGQPENNYKTAPP VLDSDGSFFLYSKLTVDKSRWQQGNVFSCSVMHEALH NHYTQKSLSLSPGKHHHHHHHEPEA |
| 13 | Mature Human CD3ε (epsilon) | Mature protein | QDGNEEMGGITQTPYKVSISGTTVILTCPQYPGSEILW QHNDKNIGGDEDDKNIGSDEDHLSLKEFSELEQSGYYV CYPRGSKPEDANFYLYLRARVCENCMEMDVMSVATIV IVDICITGGLLLLVYYWSKNRKAKAKPVTRGAGAGGRQ RGQNKERPPPVPNPDYEPIRKGQRDLYSGLNQRRI |

TABLE 1-continued

Amino acid and nucleic acid sequence

| SEQ ID NO: | Reference | Domain | Sequence |
|---|---|---|---|
| 14 | b12_VH | VH | QVQLVQSGAEVKKPGASVKVSCQAS<u>GYRFSNFV</u>IHWV RQAPGQRFEWMGW<u>INPYNGNK</u>EFSAKFQDRVTFTA DTSANTAYMELRSLRSADTAVYYC<u>ARVGPYSWDDSPQ DNYYMDV</u>WGKGTTVIVSS |
| 15 | b12_VL | VL | EIVLTQSPGTLSLSPGERATFSCRSS<u>HSIRSRR</u>VAWYQH KPGQAPRLVIH<u>GVS</u>NRASGISDRFSGSGSGTDFTLTITR VEPEDFALYYC<u>QVYGASSYT</u>FGQGTKLERK |
| 16 | VH_huCD3-H1L1 | VH | EVKLVESGGGLVQPGGSLRLSCAAS<u>GFTFNTYA</u>MNWV RQAPGKGLEWVAR<u>IRSKYNNYAT</u>YYADSVKDRFTISRD DSKSSLYLQMNNLKTEDTAMYYC<u>VRHGNFGNSYVSW FAY</u>WGQGTLVTVSS |
| 17 | VH_huCD3-H1L1-H101G | VH | EVKLVESGGGLVQPGGSLRLSCAAS<u>GFTFNTYA</u>MNWV RQAPGKGLEWVAR<u>IRSKYNNYAT</u>YYADSVKDRFTISRD DSKSSLYLQMNNLKTEDTAMYYC<u>VRGGNFGNSYVSW FAY</u>WGQGTLVTVSS |
| 18 | VH_huCD3-H1L1_CDR1 | VH_CDR1 | GFTFNTYA |
| 19 | VH_huCD3-H1L1_CDR2 | VH_CDR2 | IRSKYNNYAT |
| 20 | VH_huCD3-H1L1_CDR3 | VH_CDR3 | VRHGNFGNSYVSWFAY |
| 21 | VH_huCD3-H1L1-H101G_CDR3 | VH_CDR3 | VRGGNFGNSYVSWFAY |
| 22 | VL_huCD3-H1L1 | VL | QAVVTQEPSFSVSPGGTVTLTCRSS<u>TGAVTTSNY</u>ANW VQQTPGQAFRGLIG<u>GTN</u>KRAPGVPARFSGSLIGDKAAL TITGAQADDESIYFC<u>ALWYSNLWV</u>FGGGTKLTVL |
| 23 | VL_huCD3-H1L1_CDR1 | VL_CDR1 | TGAVTTSNY |
|  | VL_huCD3-H1L1_CDR2 | VL_CDR2 | GTN |
| 24 | VL_huCD3-H1L1_CDR3 | VL_CDR3 | ALWYSNLWV |
| 25 | VH_B7H4-C1 | VH | QVQLQQWGAGLLKPSETLSLTCAVY<u>GGSFSGYY</u>WSWI RQPPGKGLEWIGE<u>INHSGST</u>NYNPSLKSRVTISIDTSKN QFSLKLTSVTAADTAVFYC<u>ARGLFNWNFDS</u>WGQGTLV TVSS |
| 26 | VH_B7H4-C1_CDR1 | VH_CDR1 | GGSFSGYY |
| 27 | VH_B7H4-C1_CDR2 | VH_CDR2 | INHSGST |
| 28 | VH_B7H4-C1_CDR3 | VH_CDR3 | ARGLFNWNFDS |
| 29 | VH_B7H4-C1-N52S | VH | QVQLQQWGAGLLKPSETLSLTCAVY<u>GGSFSGYY</u>WSWI RQPPGKGLEWIGE<u>ISHSGST</u>NYNPSLKSRVTISIDTSKN QFSLKLTSVTAADTAVFYC<u>ARGLFNWNFDS</u>WGQGTLV TVSS |
| 30 | VH_B7H4-C1-N52S_CDR2 | VH_CDR2 | ISHSGST |
| 31 | VH_B7H4-C1-N52Q | VH | QVQLQQWGAGLLKPSETLSLTCAVY<u>GGSFSGYY</u>WSWI RQPPGKGLEWIGE<u>IQHSGST</u>NYNPSLKSRVTISIDTSKN QFSLKLTSVTAADTAVFYC<u>ARGLFNWNFDS</u>WGQGTLV TVSS |

TABLE 1-continued

Amino acid and nucleic acid sequence

| SEQ ID NO: | Reference | Domain | Sequence |
|---|---|---|---|
| 32 | VH_B7H4-C1-N52Q_CDR2 | VH_CDR2 | IQHSGST |
| 33 | VL_B7H4-C1 | VL | DIQMTQSPSSLSASVGDRVTITCRAS<u>QGIRND</u>LGWYQQKPGKAPKRLIY<u>GAS</u>SLQSGVPSRFSGSGSGTEFTLTISSLQPEDFATYYC<u>LQHNSYPRT</u>FGQGTTVEIK |
| 34 | VL_B7H4-C1_CDR1 | VL_CDR1 | QGIRND |
|  | VL_B7H4-C1_CDR2 | VL_CDR2 | GAS |
| 35 | VL_B7H4-C1_CDR3 | VL_CDR3 | LQHNSYPRT |
| 36 | VH_B7H4-C3 | VH | EVQLVQSGAEVKKPGASVKVSCKAS<u>GYTFTNFW</u>IHWVRQAPGQGLEWIGE<u>IDPSDSYT</u>NYNQKFKGRVTITRDTSTSTAYLELSSLRSEDTAVYYC<u>AREITTVDY</u>WGQGTLVTVSS |
| 37 | VH_B7H4-C3_CDR1 | VH_CDR1 | GYTFTNFW |
| 38 | VH_B7H4-C3_CDR2 | VH_CDR2 | IDPSDSYT |
| 39 | VH_B7H4-C3_CDR3 | VH_CDR3 | AREITTVDY |
| 40 | VL_B7H4-C3 | VL | DIQMTQSPSSLSASVGDRVTITCSAT<u>SSISY</u>MHWYQQKPGKAPKGWIY<u>DTS</u>KLAHGVPSRFSGSGSGTDFTLTISSLQPEDFATYYC<u>HQRRSYPFT</u>FGQGTKVEIK |
| 41 | VL_B7H4-C3_CDR1 | VL_CDR1 | SSISY |
|  | VL_B7H4-C3_CDR2 | VL_CDR2 | DTS |
| 42 | VL_B7H4-C3_CDR3 | VL_CDR3 | HQRRSYPFT |
| 43 | VH_B7H4-C2 | VH | EVQLVQSGAEVKKPGASVKVSCKAS<u>GYTFTSYW</u>IGWVRQAPGQGLEWIGD<u>IYPGGGYT</u>NYNEKFKGRVTITRDTSTSTAYLELSSLRSEDTAVYYC<u>ARLDGSSYRGAMDS</u>WGQGTLVTVSS |
| 44 | VH_B7H4-C2_CDR1 | VH_CDR1 | GYTFTSYW |
| 45 | VH_B7H4-C2_CDR2 | VH_CDR2 | IYPGGGYT |
| 46 | VH_B7H4-C2_CDR3 | VH_CDR3 | ARLDGSSYRGAMDS |
| 47 | VL_B7H4-C2 | VL | DIQMTQSPSSLSASVGDRVTITCKAS<u>QGFNKY</u>VAWYQQKPGKAPKLLIY<u>YTS</u>TLQPGVPSRFSGSGSGRDYTLTISSLQPEDFATYYC<u>LQYGNLLYA</u>FGQGTKVEIK |
| 48 | VL_B7H4-C2_CDR1 | VL_CDR1 | QGFNKY |
|  | VL_B7H4-C2_CDR2 | VL_CDR2 | YTS |
| 49 | VL_B7H4-C2_CDR3 | VL_CDR3 | LQYGNLLYA |
| 50 | VH_B7H4-C4 | VH | EVQLVESGGGLIQPGGSLRLSCAAS<u>GFTVSSNYMN</u>WVRQAPGKGLEWVS<u>VIYGSGRT</u>YYADSVKGRVTISRDNSKNTLYLQMNSLRAEDTAVYYC<u>ARDTYAMDV</u>WGQGTTVTVSS |

TABLE 1-continued

Amino acid and nucleic acid sequence

| SEQ ID NO: | Reference | Domain | Sequence |
|---|---|---|---|
| 51 | VH_B7H4-C4_CDR1 | VH_CDR1 | GFTVSSNY |
| 52 | VH_B7H4-C4_CDR2 | VH_CDR2 | IYGSGRT |
| 53 | VH_B7H4-C4_CDR3 | VH_CDR3 | ARDTYAMDV |
| 54 | VL_B7H4-C4 | VL | EIVLTQSPGTLSLSPGERATLSCRAS<u>QSVSSSY</u>LAWYQQKPGQAPRLLIY<u>GASS</u>RATGIPDRFSGSGSGTDFTLTISRLEPEDFAVYYC<u>QQYGSSPMYT</u>FGQGTKLEIK |
| 55 | VL_B7H4-C4_CDR1 | VL_CDR1 | QSVSSSY |
|  | VL_B7H4-C4_CDR2 | VL_CDR2 | GAS |
| 56 | VL_B7H4-C4_CDR3 | VL_CDR3 | QQYGSSPMYT |
| 57 | IgG1-Fc | Constant | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 58 | IgG1-Fc_F405L | Constant | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFLLYSKLTVDKSRWQQGNVFSCSVMHEALHNHYTQKSLSLSPGK |
| 59 | IgG1-Fc_FEA | Constant | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 60 | IgG1-Fc_FEAL | Constant | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFLLYSKLTVDKSRWQQGNVFSCSVMHEALHNHYTQKSLSLSPGK |
| 61 | IgG1-Fc_FEAR | Constant | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPGK |

TABLE 1-continued

Amino acid and nucleic acid sequence

| SEQ ID NO: | Reference | Domain | Sequence |
|---|---|---|---|
| 62 | IgG1-Fc_K409R | Constant | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFFLYSRLTVDKSRWQQGNV FSCSVMHEALHNHYTQKSLSLSPGK |
| 63 | Kappa | Constant | RIVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC |
| 64 | Lambda | Constant | GQPKAAPSVTLFPPSSEELQANKATLVCLISDFYPGAVT VAWKADSSPVKAGVETTTPSKQSNNKYAASSYLSLTPE QWKSHRSYSCQVTHEGSTVEKTVAPTECS |
| 65 | VH_B7H4-05 | VH | QLQLQESGPGLVKPSETLSLTCTVSGGSIKSGSYYWGWI RQPPGKGLEWIGNIYYSGSTYYNPSLRSRVTISVDTSKN QFSLKLSSVTAADTAVYYCAREGSYPNQFDPWGQGTL VTVSS |
| 66 | VH_B7H4-C5_CDR1 | VH_CDR1 | GGSIKSGSYY |
| 67 | VH_B7H4-C5_CDR2 | VH_CDR2 | IYYSGST |
| 68 | VH_B7H4-C5_CDR3 | VH_CDR3 | AREGSYPNQFDP |
| 69 | VL_B7H4-05 | VL | EIVMTQSPATLSVSPGERATLSCRASQSVSSNLAWYQQ KPGQAPRLLIYGASTRATGIPARFSGSGSGTEFTLTISSL QSEDFAVYYCQQYHSFPPTFGGGTKVEIK |
| 70 | VL_B7H4-C5_CDR1 | VL_CDR1 | QSVSSN |
|  | VL_B7H4-C5_CDR2 | VL_CDR2 | GAS |
| 71 | VL_B7H4-C5_CDR3 | VL_CDR3 | QQYHSFPPT |

The CDR regions in the table listed above (CDR1, CDR2 and CDR3, and underlined sequences in VH and VL sequences) have been annotated according to IMGT (see Lefranc M P. et al., Nucleic Acids Research, 27, 209-212, 1999] and Brochet X. Nucl. Acids Res. 36, W503-508 (2008)). The references to K405L and K409R as used in the table above is in accordance with the Eu-index of numbering (described in Kabat, E. A. et al., Sequences of proteins of immunological interest. 5th Edition—US Department of Health and Human Services, NIH publication No. 91-3242, pp 662,680,689 (1991).

DETAILED DESCRIPTION

Definitions

The term "antibody" as used herein is intended to refer to an immunoglobulin molecule, a fragment of an immunoglobulin molecule, or a derivative of either thereof, which has the ability to specifically bind to an antigen under typical physiological and/or tumor-specific conditions with a half-life of significant periods of time, such as at least about 30 minutes, at least about 45 minutes, at least about one hour, at least about two hours, at least about four hours, at least about 8 hours, at least about 12 hours, at least about 24 hours or more, at least about 48 hours or more, at least about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to be internalized). An antibody comprises a binding region (or binding domain which may be used herein, both having the same meaning) which can interact with an antigen, a binding region comprising variable regions of both heavy and light chains of an immunoglobulin molecule, or the like. Antibodies can comprise constant regions of the antibodies (Abs) which may mediate the binding of the immunoglobulin to host tissues or factors, including various cells of the immune system (such as effector cells) and components of the complement system such as C1q, the first component in the classical pathway of complement activation.

In the context of the present invention, the term "antibody" includes a monoclonal antibody (mAb), an antibody-like polypeptide, a chimeric antibody, a humanized antibody, as well as an 'antibody fragment' or a 'fragment thereof' retaining the ability to specifically bind to the antigen (antigen-binding fragment) provided by any known technique, such as enzymatic cleavage, peptide synthesis, and recombinant DNA technology. The term "antibody" includes bispecific antibodies and/or antibodies having further modifications, e.g. antibody-drug conjugates thereof.

An antibody as defined according to the invention can possess any isotype unless the disclosure herein is otherwise limited.

It has been shown that the antigen-binding function of an antibody may be performed by fragments of a full-length antibody. Examples of binding fragments encompassed within the term "antibody" include (i) a Fab' or Fab fragment, a monovalent fragment consisting of the light chain variable domain (VL), heavy chain variable domain (VH), light chain constant region (CL) and heavy chain constant region domain 1 (CH1) domains, or a monovalent antibody as described in WO 2007/059782; (ii) F(ab')$_2$ fragments, bivalent fragments comprising two Fab fragments linked by a disulfide bridge at the hinge region; (iii) an Fd fragment consisting essentially of the VH and CH1 domains; (iv) an Fv fragment consisting essentially of the VL and VH domains of a single arm of an antibody, (v) a dAb fragment Ward et al., Nature 341, 544-546 (1989), which consists essentially of a VH domain and is also called domain antibody Holt et al; Trends Biotechnol. 2003 November; 21(11):484-90; (vi) camelid or nanobodies Revets et al; Expert Opin Biol Ther. 2005 January; 5(1):111-24 and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Revets et al; Expert Opin Biol Ther. 2005 January; 5(1):111-24 and Bird et al., Science 242, 423-426 (1988). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein.

An antibody can be produced in and collected from different in vitro or ex vivo expression or production systems, for example from recombinantly modified host cells, from hybridomas or systems that use cellular extracts supporting in vitro transcription and/or translation of nucleic acid sequences encoding the antibody. It is to be understood that a multitude of different antibodies, the antibodies being as defined in the context of the present invention, can be provided by producing each antibody separately in a production system as mentioned above and thereafter mixing the antibodies, or by producing several antibodies in the same production system.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 (Paul, W., ed., 2nd ed. Raven Press, N.Y. (1989)). Within the structure of the immunoglobulin, the two heavy chains are inter-connected via disulfide bonds in the so-called "hinge region". Equally to the heavy chains, each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4.

When used herein, the terms "half molecule", "Fab-arm" and "arm" refer to one heavy chain-light chain pair. When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein below, including for example recombining by half-molecule exchange, as well as recombining at nucleic acid level and/or through co-expression of two half-molecules in the same cells.

The term "antigen-binding region" or "binding region" as used herein, refers to a region of an antibody which is capable of binding to the antigen. The antigen can be any molecule, such as a polypeptide. Antigens may e.g. be presented on a cell, bacterium, or virion. The terms "antigen" and "target" may, unless contradicted by the context, be used interchangeably in the context of the present invention. The terms "antigen-binding region" and "antigen-binding site" may, unless contradicted by the context, be used interchangeably in the context of the present invention.

The term "blocks binding" or "blocking the binding of an antibody" or "cross-blocking binding" or "cross-blocks binding" refers to the situation where one antibody bound to a specific antigen prevents binding of the second antibody to the same antigen and vice versa. In the absence of the other antibody, each antibody has the ability to bind to the antigen as determined by a significant binding response, whereas one of the antibodies lacks a binding response when the other antibody is present. The ability of one antibody to block the binding of another antibody may be determined by biolayer interferometry in a classical sandwich epitope binning assay format, for instance as described in Example 5 in the present application and by Abdiche et al. (Abdiche Y N, Malashock D S, Pinkerton A, Pons J. Exploring blocking assays using Octet, ProteOn, and Biacore biosensors. Anal Biochem. 2009; 386(2): 172-180). Briefly, in a sandwich epitope binning assay, an antibody in solution is tested for binding to its specific antigen that is first captured via an immobilized antibody. In the context of the present invention, one antibody does not block the binding of a second antibody if it is capable of binding to the antigen in the presence the second antibody and vice versa. The terms "blocks binding" and "blocking the binding of an antibody" and "cross-blocking binding" and "cross-blocks binding" may, unless contradicted by the context, be used interchangeably in the context of the present invention. An antibody that is said to blocks binding of another antibody, may also be said to compete with the other antibody for binding to the target.

The term "$K_D$" (M), as used herein, refers to the equilibrium dissociation constant of a particular antibody-antigen interaction, and is obtained by dividing $k_d$ by $k_a$. $K_D$ can also be referred to as "binding affinity".

The term "$k_d$" (sec$^{-1}$), as used herein, refers to the dissociation rate constant of a particular antibody-antigen interaction. Said value is also referred to as the $k_{off}$ value or off-rate.

The term "$k_a$" (M$^{-1}$×sec$^{-1}$), as used herein, refers to the association rate constant of a particular antibody-antigen interaction. Said value is also referred to as the $k_{on}$ value or on-rate.

The term "binding" as used herein refers to the binding of an antibody to a predetermined antigen or target, typically with a binding affinity corresponding to a $K_D$ of 1E$^{-6}$ M or less, e.g. 5E$^{-7}$ M or less, 1E$^{-7}$ M or less, such as 5E$^{-8}$ M or less, such as 1E$^{-8}$ M or less, such as 5E$^{-9}$ M or less, or such as 1E$^{-9}$ M or less, when determined by biolayer interferometry using the antibody as the ligand and the antigen as the analyte and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely-related antigen.

The term "B7H4" as used herein, refers to a protein entitled B7H4, which is also referred to as: B7-H4; V-set domain containing T cell activation inhibitor 1; or VTCN1. B7H4 is a member of the B7 family of proteins, which family comprises cell-surface protein ligands that bind to receptors on lymphocytes. B7H4 is a type I transmembrane protein that includes a short intracellular domain, a hydrophobic transmembrane domain, and an extracellular domain with an IgV- and an IgC-like domain with four conserved cysteine residues and seven sites for N-linked glycosylation. (Sica et al., 2003, Immunity 18: 849-861). B7H4 proteins are known from various species, such as human (*Homo sapiens*) B7H4 (Uniprot accession no. Q7Z7D3), cynomolgus monkey (*Macaca fascicularis*) B7H4 transcript 1 (Uniprot accession no. A0A2K5U6P5), dog (*Canis familiaris*) B7H4 (Uniprot accession no. F1P8R9), rabbit (*Oryctolagus cuniculus*) B7H4 (Uniprot accession no. G1TQE8), rat (*Rattus norvegicus*) B7H4 (Uniprot accession no. Q501W4), mouse (*Mus musculus*) B7H4 (Uniprot accession no. Q7TSP5), and pig (*Sus scrofa*) B7H4 (Uniprot accession no. F1SAY4). Natural variants of the listed B7H4 sequences may exist.

The term "CD3" as used herein, refers to the human Cluster of Differentiation 3 protein which is part of the T-cell co-receptor protein complex and is composed of four distinct chains. CD3 is found in various species, and thus the term "CD3" may not be limited to human CD3, unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ (delta) chain (human CD3δ UniProtKB/Swiss-Prot No P04234, or cynomolgus monkey CD3δ UniProtKB/Swiss-Prot No Q95LI8), two CD3ε (epsilon) chains (human CD3ε: UniProtKB/Swiss-Prot No P07766, of which a sequence herein is incorporated as SEQ ID NO: 13, in which amino acid residues 1-22 represent a signal peptide and amino acid residues 23-207 represent the mature CD3ε polypeptide; cynomolgus monkey CD3ε UniProtKB/Swiss-Prot No Q95L15; or rhesus monkey CD3ε UniProtKB/Swiss-Prot No G7NCB9), and a CD3ζ-chain (zeta) chain (human CD3ζ UniProtKB/Swiss-Prot No P20963, cynomolgus monkey CD3ζ UniProtKB/Swiss-Prot No Q09TK0). These chains associate with a molecule known as the T cell receptor (TCR) and generate an activation signal in T lymphocytes. The TCR and CD3 molecules together comprise the TCR complex.

The term "antibody binding region" refers to a region of the antigen, which comprises the epitope to which the antibody binds. An antibody binding region may be determined by epitope binning using biolayer interferometry, by alanine scan, or by domain shuffle assays (using antigen constructs in which regions of the antigen are exchanged with that of another species and determining whether the antibody still binds to the antigen or not). The amino acids within the antibody binding region that are involved in the interaction with the antibody may be determined by hydrogen/deuterium exchange mass spectrometry and/or by crystallography of the antibody bound to its antigen.

The term "epitope" means an antigenic determinant which is specifically bound by an antibody. Epitopes usually consist of surface groupings of molecules such as amino acids, sugar side chains or a combination thereof and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the antibody when it is bound to the antigen (in other words, the amino acid residue is within or closely adjacent to the footprint of the specific antibody).

The terms "monoclonal antibody", "monoclonal Ab", "monoclonal antibody composition", "mAb", or the like, as used herein refer to a preparation of antibody molecules of single molecular composition and typically displays a single binding specificity and affinity for a particular epitope. A monoclonal antibody can be typically made by identical cells that are all clones of a unique parent cell, such as for example hybridomas, stable cell lines or the like. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal nonhuman animal, such as a transgenic mouse, having a genome comprising a human heavy chain transgene and a light chain transgene, fused to an immortalized cell. Human monoclonal antibodies may be derived from human B cells or plasma cells. Monoclonal antibodies may also be produced from recombinantly modified host cells, or systems that use cellular extracts supporting in vitro transcription and/or translation of nucleic acid sequences encoding the antibody.

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m(f)) that is encoded by heavy chain constant region genes. Further, each heavy chain isotype can be combined with either a kappa (κ) or lambda (λ) light chain.

The term "full-length antibody" when used herein, refers to an antibody (e.g., a parent or variant antibody) comprising one pair of a heavy and light chain or two different pairs of heavy and light chains, each pair containing heavy and light chain constant and variable domains such as normally found in a heavy chain-light chain pair of a wild-type antibody of that isotype. In a full length variant antibody, the heavy and light chain constant and variable domains may in particular contain amino acid substitutions that modify and/or improve functional properties of the antibody when compared to the full length parent or wild-type antibody. A full-length antibody according to the present invention may be produced by a method comprising the steps of (i) cloning the CDR sequences into one or more suitable vectors comprising complete heavy and light chain sequences, and (ii) expressing the obtained suitable vectors with the heavy and light chain sequences in suitable expression systems. It is within the knowledge of the skilled person to produce a full-length antibody when starting out from either CDR sequences or full variable region sequences. Thus, the skilled person knows how to generate a full-length antibody in accordance with the present invention.

The term "humanized antibody" as used herein, refers to a genetically engineered non-human antibody, which contains human antibody constant domains and non-human variable domains modified to contain a high level of sequence homology to human variable domains. This can be achieved by grafting of non-human antibody complementarity-determining regions (CDRs), which together form the antigen binding site, onto a homologous human acceptor framework region (FR) (see i.a. WO92/22653 and EP0629240). In order to fully reconstitute the binding affinity and specificity of the parental antibody, substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as particular useful affinity and biochemical properties, e.g. to include modifications to avoid deamidation, provide an "inert Fc region", and/or improve manufacturing.

The term "human antibody", as used herein, is intended to include antibodies having variable and framework regions derived from human germline immunoglobulin sequences and a constant domain derived from a human immunoglobulin constant domain. The human antibodies of the invention may include amino acid residues not encoded by human germline immunoglobulin sequences (e.g., mutations, insertions or deletions introduced by random or site-specific mutagenesis in vitro or by somatic mutation in vivo). A "human antibody" can incorporate VH and VL sequences that have been generated from human germline immunoglobulin sequences in a human, in a transgenic animal such as described in the examples herein, a HIS mouse, or the like. Such VH and VL sequences are considered human VH and VL sequences, which have been e.g. fused to constant domains derived from a human immunoglobulin constant domain.

Hence, "human antibodies" can be engineered antibodies. A "human antibody" may have been subjected to further engineering, e.g. include modifications to avoid deamidation, provide an "inert Fc region", enable bispecific antibody generation and/or improve manufacturing. A human antibody may also be produced in non-human cells, e.g. in CHO cells or the like. However, the term "human antibody", as used herein, is not intended to include antibodies in which CDR sequences derived from the germline of another non-human species, such as a mouse, have been grafted onto human framework sequences.

The term "Fc region" as used herein, refers to a region comprising, in the direction from the N- to C-terminal ends of the two heavy chains of the antibody, at least a hinge region, a CH2 region and a CH3 region. An Fc region of the antibody may mediate the binding of the immunoglobulin to host tissues or factors, including various cells of the immune system (such as effector cells) and components of the complement system.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat Kabat, E. A. et al., Sequences of proteins of immunological interest. 5th Edition—US Department of Health and Human Services, NIH publication No. 91-3242, pp 662,680,689 (1991). However, the hinge region may also be any of the other subtypes as described herein.

The term "CH1 region" or "CH1 domain" as used herein refers to the CH1 region of an immunoglobulin heavy chain. Thus, for example the CH1 region of a human IgG1 antibody corresponds to amino acids 118-215 according to the Eu numbering as set forth in Kabat (ibid). However, the CH1 region may also be any of the other subtypes as described herein.

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering as set forth in Kabat (ibid). However, the CH2 region may also be any of the other subtypes as described herein.

The term "CH3 region" or "CH3 domain" as used herein refers to the CH3 region of an immunoglobulin heavy chain. Thus, for example the CH3 region of a human IgG1 antibody corresponds to amino acids 341-447 according to the Eu numbering as set forth in Kabat (ibid). However, the CH3 region may also be any of the other subtypes as described herein.

The term "Fc-mediated effector functions," as used herein, is intended to refer to functions that are a consequence of binding a polypeptide or antibody to its target or antigen on a cell membrane wherein the Fc-mediated effector function is attributable to the Fc region of the polypeptide or antibody. Examples of Fc-mediated effector functions include (i) C1q binding, (ii) complement activation, (iii) complement-dependent cytotoxicity (CDC), (iv) antibody-dependent cell-mediated cytotoxicity (ADCC), (v) Fc-gamma receptor (FcgR)-binding, (vi) antibody-dependent, FcγR-mediated antigen crosslinking, (vii) antibody-dependent cellular phagocytosis (ADCP), (viii) complement-dependent cellular cytotoxicity (CDCC), (ix) complement-enhanced cytotoxicity, (x) binding to complement receptor of an opsonized antibody mediated by the antibody, (xi) opsonisation, and (xii) a combination of any of (i) to (xi).

The term "inertness", "inert" or "non-activating" as used herein, refers to an Fc region which is at least not able to bind any FcγR, induce Fc-mediated cross-linking of FcγRs, or induce FcγR-mediated cross-linking of target antigens via two Fc regions of individual antibodies, or is not able to bind C1q. An example thereof is FEA substitutions within the constant domain as described herein. The inertness of an Fc region of an antibody, may be tested using the antibody in a monospecific or bispecific format.

The term "full-length" when used in the context of an antibody indicates that the antibody is not a fragment, but contains all of the domains corresponding with the particular isotype such as normally found for that isotype in nature, e.g. the VH, CH1, CH2, CH3, hinge, VL and CL domains for an IgG1 antibody.

The term "monovalent antibody", in the context of the present invention, refers to an antibody molecule that can interact with an antigen, with only one antigen-binding domain (e.g. one Fab arm). In the context of a bispecific antibody, "monovalent antibody binding" refers to the binding of the bispecific antibody to one antigen with only one antigen-binding domain (e.g. one Fab arm).

The term "monospecific antibody" in the context of the present invention, refers to an antibody that has binding specificity to one antigen, one epitope only. The antibody may be a monospecific, monovalent antibody (i.e. carrying only one antigen-binding region) or a monospecific, bivalent antibody (e.g. an antibody with two identical antigen-binding regions).

The term "bispecific antibody" refers to an antibody having two antigen-binding domains that bind different epitopes, e.g. two non-identical pairs of VH and VL regions, two non-identical Fab-arms or two Fab-arms with non-identical CDR regions. In the context of this invention, bispecific antibodies have specificity for at least two different epitopes. Such epitopes may be on the same or different antigens or targets. If the epitopes are on different antigens, such antigens may be on the same cell or different cells, cell types or structures, such as extracellular matrix or vesicles and soluble protein. A bispecific antibody may thus be capable of crosslinking multiple antigens, e.g. two different cells.

The term "bivalent antibody" refers to an antibody that has two antigen-binding regions, which bind to two of the same epitopes on two of the same antigens or binds to two different epitopes on the same or different antigen(s). Hence, a bivalent antibody may be a monospecific antibody or a bispecific antibody.

The term "amino acid" and "amino acid residue" may herein be used interchangeably, and are not to be understood limiting. Amino acids are organic compounds containing amine ($-NH_2$) and carboxyl ($-COOH$) functional groups, along with a side chain (R group) specific to each amino acid. In the context of the present invention, amino acids may be classified based on structure and chemical characteristics. Thus, classes of amino acids may be reflected in one or both of the following tables:

Main classification based on structure and general chemical characterization of R group

TABLE 2

| Class | Amino acid |
| --- | --- |
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Alternative Physical and Functional Classifications of Amino Acid Residues

| Class | Amino acid |
| --- | --- |
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

Substitution of one amino acid for another may be classified as a conservative or non-conservative substitution. In the context of the invention, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues.

In the context of the present invention, a substitution in an antibody is indicated as:

Original amino acid-position-substituted amino acid;

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine.

Accordingly, the notation "K409R" or "Lys409Arg" means, that the antibody comprises a substitution of Lysine with Arginine in amino acid position 409. Substitution of an amino acid at a given position to any other amino acid is referred to as: Original amino acid—position; or e.g. "K409". For a modification where the original amino acid(s) and/or substituted amino acid(s) may comprise more than one, but not all amino acid(s), the more than one amino acid may be separated by "," or "/". E.g. the substitution of Lysine with Arginine, Alanine, or Phenylalanine in position 409 is: "Lys409Arg,Ala,Phe" or "Lys409Arg/Ala/Phe" or "K409R,A,F" or "K409R/A/F" or "K409 to R, A, or F". Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409O, 409R, 409S, 409T, 409V, 409W, 409P, and 409Y. This is, by the way, equivalent to the designation 409X, wherein the X designates any amino acid other than the original amino acid. These substitutions may also be designated K409A, K409C, etc. or K409A,C, etc. or K409A/C/etc. The same applies by analogy to each and every position mentioned herein, to specifically include herein any one of such substitutions.

The antibody according to the invention may also comprise a deletion of an amino acid residue. Such deletion may be denoted "del", and includes, e.g., writing as K409del. Thus, in case of such embodiments, the Lysine in position 409 has been deleted from the amino acid sequence.

The term "host cell", as used herein, is intended to refer to a cell into which a nucleic acid such as an expression vector has been introduced. It should be understood that such terms are intended to refer not only to the particular subject cell, but may also include the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, Expi293F cells, PER.C6 cells, NS0 cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6 cells, NS0 cells, HEK-293 cells, Expi293F cells, plant cells, or fungi, including yeast cells.

For purposes of the present invention, sequence identity between two amino acid sequences is determined over the length of the referenced sequence using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment).

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent or referenced sequence.

The term "internalized" or "internalization" as used herein, refers to a biological process in which molecules such as the antibody according to the present invention, are engulfed by the cell membrane and drawn into the interior of the cell. Internalization may also be referred to as "endocytosis".

Bispecific Antibodies Targeting CD3xB7H4

In a first aspect of the invention, an antibody is provided comprising an antigen-binding region capable of binding to human B7H4 and an antigen-binding region capable of binding to human CD3, wherein said antigen-binding regions comprise heavy and light chain variable regions, wherein said antigen-binding regions are human variable regions and/or humanized variable regions. For example, one antigen-binding region may comprise human heavy and light chain variable regions, and the other antigen-binding region may comprise humanized heavy and light chain variable regions. Or, both antigen-binding region may comprise human heavy and light chain variable regions, or both antigen-binding regions may comprise humanized heavy and light chain variable regions. Hence, accordingly, an antibody is provided comprising an antigen-binding region capable of binding to human B7H4 and an antigen-binding region capable of binding to human CD3, wherein said antigen-binding regions comprise heavy and light chain variable regions, wherein said heavy and light chain variable regions comprise human framework regions. An antibody in accordance with the invention as described herein comprising an antigen-binding region capable of binding to human B7H4 and an antigen-binding region capable of binding to human CD3, may also be referred to herein e.g. as a B7H4xCD3 antibody.

Such antibodies are preferably bispecific antibodies. Such an antibody as described above are in a further embodiment capable of binding cancer cells and T-cells, such as e.g. described in the examples. Cancer cells that may be selected are cancer cells that express human B7H4 and/or are cancer cells that are of a solid tumor. Such an antibody preferably is capable of inducing T-cell mediated cell killing of the cancer cells.

Capable of binding is understood to comprise, as shown in the examples, that in a binding assay, an antibody binds to its target, as shown by e.g. typical binding curves such as shown in FIGS. 3 and 4 herein, or by determining binding affinity, using e.g. biolayer interferometry, as shown in examples 3 and 4. An antigen-binding region not capable of binding to a specified target has e.g. an undetable binding affinity to its target, e.g. having a response of <0.05 nm at the highest concentration used in a typical biolayer interferometry assay such as shown in example 3. In any case, the skilled person is well aware how to determine whether or not an antigen-bindig region is capable of binding to its target.

Bispecific Formats

The present invention provides bispecific CD3xB7H4 antibodies which efficiently promote T cell-mediated killing of B7H4-expressing tumor cells. Depending on the desired functional properties for a particular use, particular antigen-binding regions can be selected from the set of antibodies or antigen-binding regions provided by the present invention. Many different formats and uses of bispecific antibodies are known in the art, and were reviewed by Kontermann; Drug Discov Today, 2015 July; 20(7):838-47 and; MAbs, 2012

March-April; 4(2):182-97. A bispecific antibody according to the present invention may not be limited to any particular bispecific format or method of producing it.

Examples of bispecific antibody molecules which may be used in the present invention comprise (i) a single antibody that has two arms comprising different antigen-binding regions; (ii) a single chain antibody that has specificity to two different epitopes, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')2 fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, or a bispecific antibody obtained via a controlled Fab-arm exchange (such as described in WO2011131746 (Genmab)).

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc-regions or parts thereof.

Examples of IgG-like molecules with complementary CH3 domain molecules include but are not limited to the Triomab/Quadroma molecules (Trion Pharma/Fresenius Biotech; Roche, WO2011069104), the so-called Knobs-into-Holes molecules (Genentech, WO9850431), CrossMAbs (Roche, WO2011117329) and the electrostatically-matched molecules (Amgen, EP1870459 and WO2009089004; Chugai, US201000155133; Oncomed, WO2010129304), the LUZ-Y molecules (Genentech, Wranik et al. J. Biol. Chem. 2012, 287(52): 43331-9, doi: 10.1074/jbc.M112.397869. Epub 2012 Nov. 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcAAdp molecules (Regeneron, WO201015792), bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab A/S, WO2011131746).

Examples of recombinant IgG-like dual targeting molecules include but are not limited to Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2):208-18), approaches with common light chain (Crucell/Merus, U.S. Pat. No. 7,262,028), κλBodies (NovImmune, WO2012023053) and CovX-body (CovX/Pfizer; Doppalapudi, V. R., et al 2007. Bioorg. Med. Chem. Lett. 17, 501-506.).

Examples of IgG fusion molecules include but are not limited to Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2):191-8), Ts2Ab (MedImmune/AZ; Dimasi et al. J Mol Biol. 2009 Oct. 30; 393(3):672-92) and BsAb molecules (Zymogenetics, WO2010111625), HERCULES molecules (Biogen Idec, U.S. Ser. No. 00/795,1918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include but are not limited to ScFv/Fc Fusions (Pearce et al., Biochem Mol Biol Int. 1997 September; 42(6):1179-88), SCORPION molecules (Emergent BioSolutions/Trubion, Blankenship J W, et al. AACR 100 th Annual meeting 2009 (Abstract #5465); Zymogenetics/BMS, WO2010111625), Dual Affinity Retargeting Technology (Fc-DART) molecules (MacroGenics, WO2008157379, WO2010080538) and Dual(ScFv)2-Fab molecules (National Research Center for Antibody Medicine—China).

Examples of Fab fusion bispecific antibodies include but are not limited to F(ab)2 molecules (Medarex/AMGEN; Deo et al J Immunol. 1998 Feb. 15; 160(4):1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, J Immunol. 2000 Dec. 15; 165(12):7050-7.) and Fab-Fv molecules (UCB-Celltech, WO 2009040562 A1).

Examples of ScFv-, diabody-based and domain antibodies include but are not limited to Bispecific T Cell Engager (BiTE) molecules (Micromet, WO2005061547), Tandem Diabody molecules (TandAb) (Affimed) Le Gall et al., Protein Eng Des Sel. 2004 April; 17(4):357-66.), Dual Affinity Retargeting Technology (DART) molecules (MacroGenics, WO2008157379, WO2010080538), Single-chain Diabody molecules (Lawrence, FEBS Lett. 1998 Apr. 3; 425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August; 88(6): 667-75.), dual targeting nanobodies (Ablynx, Hmila et al., FASEB J. 2010) and dual targeting heavy chain only domain antibodies.

The bispecific antibody of the invention can be of any isotype. Exemplary isotypes include but are not limited to either of the human IgG1, IgG2, IgG3, and IgG4 isotypes. Preferably, bispecific antibodies may be selected to be of the human IgG1 isotype, as shown in the examples. Either of the human light chain constant regions, kappa or lambda, may be used. In one embodiment, both heavy chains of an antibody of the present invention are of the IgG1 isotype, for instance an IgG1,κ. In one embodiment, the two heavy chains of a bispecific antibody are of the IgG1 and IgG4 isotypes, respectively. Preferably, bispecific antibodies may be selected to be of the human IgG1 isotype, as shown in the examples. Optionally, and preferably, the heavy chain and Fc sequences thereof of the selected isotype, may be modified in the hinge and/or CH3 region as described herein to enable the generation of bispecific antibodies and introduce inertness.

In one aspect, the bispecific antibody of the invention comprises an Fc-region comprising a first heavy chain with a first Fc sequence comprising a first CH3 region, and a second heavy chain with a second Fc sequence comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference.

As described further herein, a stable bispecific CD3×B7H4 antibody can be obtained at high yield on the basis of one B7H4 antibody and one CD3 antibody, each composed of two identical heavy chains and two identical light chains, each antibody containing only a few, fairly conservative, (asymmetrical) mutations in the CH3 regions. Asymmetrical mutations mean that the sequences of said first and second CH3 regions contain one or more amino acid substitutions at non-identical positions.

Antigen-Binding Region Capable of Binding CD3

As said, the invention provides an antibody according to the invention comprising an antigen-binding region capable of binding to human B7H4 and an antigen-binding region capable of binding to human CD3. Furthermore, the invention provides an antibody according to the invention comprising an antigen-binding region capable of binding to human B7H4 and an antigen-binding region capable of binding to human CD3, wherein the antigen-binding region capable of binding CD3, is capable of binding human CD3ε (epsilon), such as human CD3ε (epsilon) as specified in SEQ ID NO: 13. Such antigen-binding region is capable of binding human CD3ε (epsilon), as presented on a T cell, such as a primary human T cell.

Said antibody according to the invention may be an antibody comprising an antigen-binding region capable of binding to human B7H4 and an antigen-binding region capable of binding to human CD3, wherein the antigen-binding region that binds to CD3 comprises a heavy chain variable region (VH) comprising The CDR1, CDR2, and CDR3 regions of SEQ ID NO: 16 or of SEQ ID NO. 17, and, optionally, a light chain variable region (VL) comprising the CDR1, CDR2, and CDR3 regions of SEQ ID NO: 22.

CDR1, CDR2 and CDR3 regions can be identified from variable heavy and light chain regions using methods known in the art. The CDR regions from said variable heavy and light chain regions can be annotated according to IMGT (see Lefranc M P. et al., Nucleic Acids Research, 27, 209-212, 1999] and Brochet X. Nucl. Acids Res. 36, W503-508 (2008)). Hence, also disclosed are antibodies comprising an antigen-binding region capable of binding to human B7H4 and an antigen-binding region capable of binding to human CD3, wherein the antigen-binding region that binds to CD3 comprises a heavy chain variable region (VH) comprising the CDR1, CDR2, and CDR3 sequences of SEQ ID NOs.: 18, 19 and 20 or 18, 19 and 21 respectively; and, optionally a light chain variable region (VL) comprising the CDR1, CDR2, and CDR3 sequences of SEQ ID NO: 23, GTN and 24, respectively.

Further disclosed are antibodies comprising an antigen-binding region capable of binding to human B7H4 and an antigen-binding region capable of binding to human CD3, wherein the antigen-binding region that binds to CD3 comprises a heavy chain variable region (VH) comprising the sequence of SEQ ID NO: 16, or a sequence having at least 90%, at least 95%, at least 97%, or at least 99% amino acid sequence identity to the sequence of SEQ ID NO: 16; and; optionally a light chain variable region (VL) comprising the sequence of SEQ ID NO: 22 or a sequence having at least 90%, at least 95%, at least 97%, or at least 99% amino acid sequence identity to the sequence of SEQ ID NO: 22.

Such antigen-binding regions that are capable of binding human CD3 have been described i.a. in WO2015001085, and WO2017009442. Further antigen-binding regions that are capable of binding human CD3 are disclosed and described in WO2015001085 and WO2017009442, which can be further contemplated and serve as the basis for generating antibodies in accordance with the current invention, which are incorporated by reference herein.

The said antibody in accordance with the invention, may bind with an equilibrium dissociation constant $K_D$ between the antigen-binding region that binds to human CD3, and human CD3 is within the range of 1-1000 nM.

The said antibody in accordance with the invention, may bind with a equilibrium dissociation constant $K_D$ between the antigen-binding region that binds to human CD3, and human CD3 is within the range of 1-100 nM, such as within the range of 5-100 nM, within the range of 10-100 nM, within the range of 1-80 nM, within the range of 1-60 nM within the range of 1-40 nM, within the range of 1-20 nM, within the range of 5-80 nM, within the range of 5-60 nM, within the range of 5-40 nM, within the range of 5-20 nM, within the range of 10-80 nM, within the range of 10-60 nM, within the range of 10-40 nM, or such as within the range of 10-20 nM. An exemplary and suitable antigen-binding region comprises a heavy chain variable region (VH) of SEQ ID NO: 16 and a light chain variable region (VL) regions of SEQ ID NO: 22. Such variable regions have been described i.a. in WO2015001085.

In another aspect of the invention, said antibody has a lower binding affinity for human CD3ε than an antibody having an antigen-binding region comprising a VH sequence as set forth in SEQ ID NO: 16, and a VL sequence as set forth in SEQ ID NO: 22, preferably wherein said affinity is at least 5-fold lower, such as at least 10-fold lower, e.g. at least 20-fold lower, at least 30 fold lower, at least 40 fold lower, at least 45 fold lower or such as at least 50-fold lower.

In another aspect of the invention, said antibody may bind with an equilibrium dissociation constant $K_D$ between the antigen-binding region that binds to human CD3, and human CD3 antigen-binding which is within the range of 200-1000 nM, such as within the range of 300-1000 nM, within the range of 400-1000 nM, within the range of 500-1000 nM, within the range of 300-900 nM within the range of 400-900 nM, within the range of 400-700 nM, within the range of 500-900 nM, within the range of 500-800 nM, within the range of 500-700 nM, within the range of 600-1000 nM, within the range of 600-900 nM, within the range of 600-800 nM, or such as within the range of 600-700 nM. An exemplary and suitable antigen-binding region comprises a heavy chain variable region (VH) of SEQ ID NO: 16 or of SEQ ID NO. 17, and, a light chain variable region (VL) regions of SEQ ID NO: 22. Such variable regions have been described i.a. in WO2017009442.

Said binding affinity can be determined by biolayer interferometry, optionally as set forth in Example 4 herein. Hence, the antibody according to the invention having a binding affinity to human CD3 as defined herein, may have the binding affinity determined using biolayer interferometry comprising the steps of:
I) immobilizing the antibody at an amount of 1 μg/mL for 600 seconds on an anti-human IgG Fc Capture biosensor;
II) determining association over a time period of 1000 seconds and dissociation over a time period of 2000 seconds of human recombinant soluble CD3ε (CD3E27-GSKa) (mature protein of SEQ ID NO: 13) using a 3-fold dilution series ranging from 1.40 nM to 1000 nM; and
III) referencing the data to a buffer control (0 nM).

Furthermore, said binding affinity may be determined using an antibody such as a monospecific, bivalent antibody, such as an antibody which is a full length IgG1.

Hence, in a further embodiment, the antibody according to the invention is an antibody, wherein
the antigen-binding region that binds to CD3 comprises a heavy chain variable (VH) region, as defined herein, comprising a CDR1 sequence, a CDR2 sequence and a CDR3 sequence, when compared to a heavy chain variable (VH) region comprising the sequence set forth in SEQ ID NO: 16 has an amino acid substitution being at a position selected from the group consisting of: T31, N57, H101, G105, S110 and Y114, the positions being numbered according to the sequence of SEQ ID NO: 16; and
the wild type light chain variable (VL) region comprises the CDR1, CDR2 and CDR3 sequences set forth in SEQ ID NO: 23, GTN and SEQ ID NO: 24, respectively.

In particular, the antibody according to the invention is an antibody, wherein the antigen-binding region that binds to CD3 comprises in the heavy chain variable (VH) region as defined herein comprises a substitution selected from the group consisting of: T31M, T31P, N57E, H101G, H101N, G105P, S110A, S110G, Y114M, Y114R, Y114V.

Furthermore, the antibody according to the invention is an antibody wherein the antigen-binding region that binds to CD3 comprises a heavy chain variable region as defined herein having at the amino acid position 31 an M or P, or at the amino acid position 57 an E, or at the amino acid position 101 a G or N, or at the amino acid 105 a P, or at the amino acid position 110 and A or G, or at the amino acid position 114 an M, R or V, said positions corresponding with the amino acid position numbering of the heavy chain variable (VH) region having the sequence set forth in SEQ ID NO: 16.

Still further, the antibody according to the invention is an antibody wherein the CDR1, CDR2 and CDR3 of the heavy chain variable (VH) region of the antigen-binding region that binds to CD3 as defined herein comprises, in total, at the most 1, 2, 3, 4 or 5 amino acid substitutions, when compared with the CDR1, CDR2 and CDR3 of the sequences of SEQ ID NO: 16, said amino acid substitutions comprising preferably amino acid substitutions as defined above.

Antigen-Binding Region Capable of Binding B7H4

In particular, the invention provides an antibody according to the invention comprising an antigen-binding region capable of binding to human B7H4 and an antigen-binding region capable of binding to human CD3, wherein said human B7H4 is human B7H4 of SEQ ID NO: 1. Preferably, said antibody in accordance with the invention comprises an antigen-binding region capable of binding to human CD3ε (epsilon) as specified in SEQ ID NO: 13, and an antigen-binding region capable of binding human B7H4 of SEQ ID NO: 1.

In particular, the antibody according to the invention is an antibody wherein said antigen-binding region capable of binding to human B7H4 is capable of binding to the extracellular domain of human B7H4. Preferably, said B7H4 is expressed on a cell, more preferably a human cell.

In a further embodiment, the antibody according to the invention is an antibody wherein said antigen-binding region capable of binding to human B7H4 is capable of binding to the IgC-like constant region of human B7H4. In another further embodiment, the antibody according to the invention is an antibody wherein said antigen-binding region capable of binding to human B7H4 is capable of binding to B7H3-IgV/B7H4-IgC. B7H3-IgV/B7H4-IgC represents a fusion between human B7H3 and B7H4, wherein the B7H3 IgV-like domain is fused with the B7H4 IgC-like domain, corresponding with SEQ ID NO. 11. Said B7H3-IgV/B7H4-IgC being expressed by a cell such as described in the example 7 herein. In still another further embodiment, the antibody according to the invention is an antibody wherein said antigen-binding region capable of binding to human B7H4 is not capable of binding to B7H4-IgV/B7H3-IgC. B7H4-IgV/B7H3-IgC represents a fusion between human B7H3 and B7H4, wherein the B7H4 IgV-like domain is fused with the B7H3 IgC-like domain, corresponding with SEQ ID NO. 10. Said B7H4-IgV/B7H3-IgC being expressed by a cell such as described in the example 7 herein.

Suitable antigen-binding regions capable of binding to human B7H4, that are contemplated according to the invention as described herein comprise:
a) a variable heavy chain (VH) region comprising the CDR1, CDR2 and CDR3 regions of SEQ ID NO: 25: and a variable light chain region comprising the CDR1, CDR2 and CDR3 regions respectively of SEQ ID NO. 33;
b) a variable heavy chain (VH) region comprising the CDR1, CDR2 and CDR3 regions of SEQ ID NO: 29: and a variable light chain region comprising the CDR1, CDR2 and CDR3 regions respectively of SEQ ID NO. 33;
c) a variable heavy chain (VH) region comprising the CDR1, CDR2 and CDR3 regions of SEQ ID NO: 36: and a variable light chain region comprising the CDR1, CDR2 and CDR3 regions respectively of SEQ ID NO. 40;

d) a variable heavy chain (VH) region comprising the CDR1, CDR2 and CDR3 regions of SEQ ID NO. 43: and a variable light chain region comprising the CDR1, CDR2 and CDR3 regions respectively of SEQ ID NO. 47;

e) a variable heavy chain (VH) region comprising the CDR1, CDR2 and CDR3 regions of SEQ ID NO. 50: and a variable light chain region comprising the CDR1, CDR2 and CDR3 regions respectively of SEQ ID NO.54;

f) a variable heavy chain (VH) region comprising the CDR1, CDR2 and CDR3 regions of SEQ ID NO. 31: and a variable light chain region comprising the CDR1, CDR2 and CDR3 regions respectively of SEQ ID NO. 33; or g) a variable heavy chain (VH) region comprising the CDR1, CDR2 and CDR3 regions of SEQ ID NO. 65: and a variable light chain region comprising the CDR1, CDR2 and CDR3 regions respectively of SEQ ID NO. 69.

CDR1, CDR2 and CDR3 regions can be identified from variable heavy and light chain regions using methods known in the art. The CDR regions from said variable heavy and light chain regions can be annotated according to IMGT (see Lefranc M P. et al., Nucleic Acids Research, 27, 209-212, 1999] and Brochet X. Nucl. Acids Res. 36, W503-508 (2008)). Hence, suitable antigen-binding regions capable of binding to human B7H4, that are contemplated according to the invention as described herein comprise:

a) a variable heavy chain (VH) region comprising the CDR1, CDR2 and CDR3 regions respectively of SEQ ID NOs.: 26, 27 and 28, and a variable light chain region comprising the CDR1, CDR2 and CDR3 respectively of SEQ ID NO. 34, GAS and SEQ ID NO. 35;

b) a variable heavy chain (VH) region comprising the CDR1, CDR2 and CDR3 regions respectively of SEQ ID NOs.: 26, 30 and 28, and a variable light chain region comprising the CDR1, CDR2 and CDR3 respectively of SEQ ID NO. 34, GAS and SEQ ID NO. 35;

c) a variable heavy chain (VH) region comprising the CDR1, CDR2 and CDR3 regions respectively of SEQ ID NOs.: 37, 38 and 39, and a variable light chain region comprising the CDR1, CDR2 and CDR3 respectively of SEQ ID NO. 41, DTS and SEQ ID NO. 42;

d) a variable heavy chain (VH) region comprising the CDR1, CDR2 and CDR3 regions respectively of SEQ ID NOs.: 44, 45 and 46, and a variable light chain region comprising the CDR1, CDR2 and CDR3 respectively of SEQ ID NO. 48, YTS and SEQ ID NO. 49;

e) a variable heavy chain (VH) region comprising the CDR1, CDR2 and CDR3 regions respectively of SEQ ID NOs.: 51, 52 and 53, and a variable light chain region comprising the CDR1, CDR2 and CDR3 respectively of SEQ ID NO. 55, GAS and SEQ ID NO. 56;

f) a variable heavy chain (VH) region comprising the CDR1, CDR2 and CDR3 regions respectively of SEQ ID NOs.: 26, 32 and 28, and a variable light chain region comprising the CDR1, CDR2 and CDR3 respectively of SEQ ID NO. 34, GAS and SEQ ID NO. 35; or g) a variable heavy chain (VH) region comprising the CDR1, CDR2 and CDR3 regions respectively of SEQ ID NOs.: 66, 67 and 68, and a variable light chain region comprising the CDR1, CDR2 and CDR3 respectively of SEQ ID NO. 70, GAS and SEQ ID NO. 71.

Still further suitable antigen-binding regions capable of binding to human B7H4, that are contemplated according to the invention as described herein comprise:

a) a variable heavy chain (VH) region of SEQ ID NO. 25: and a variable light chain region of SEQ ID NO. 33;

b) a variable heavy chain (VH) region of SEQ ID NO. 29: and a variable light chain region of SEQ ID NO. 33;

c) a variable heavy chain (VH) region of SEQ ID NO. 36: and a variable light chain region of SEQ ID NO. 40;

d) a variable heavy chain (VH) region of SEQ ID NO.43: and a variable light chain region of SEQ ID NO. 47;

e) a variable heavy chain (VH) region of SEQ ID NO. 50: and a variable light chain region of SEQ ID NO.54;

f) a variable heavy chain (VH) region of SEQ ID NO. 31: and a variable light chain region of SEQ ID NO. 33; or g) a variable heavy chain (VH) region of SEQ ID NO. 65: and a variable light chain region of SEQ ID NO. 69.

Optionally, said antigen-binding regions that binds to B7H4 comprise heavy and light chain variable regions (VH) having at least 90%, at least 95%, at least 97%, or at least 99% amino acid sequence identity with:

a) a variable heavy chain (VH) region of SEQ ID NO. 25: and a variable light chain region of SEQ ID NO. 33;

b) a variable heavy chain (VH) region of SEQ ID NO. 29: and a variable light chain region of SEQ ID NO. 33;

c) a variable heavy chain (VH) region of SEQ ID NO. 36: and a variable light chain region of SEQ ID NO. 40;

d) a variable heavy chain (VH) region of SEQ ID NO.43: and a variable light chain region of SEQ ID NO. 47;

e) a variable heavy chain (VH) region of SEQ ID NO. 50: and a variable light chain region of SEQ ID NO.54;

f) a variable heavy chain (VH) region of SEQ ID NO. 31: and a variable light chain region of SEQ ID NO. 33; or g) a variable heavy chain (VH) region of SEQ ID NO. 65: and a variable light chain region of SEQ ID NO. 69.

The antibody according to the invention may have an antigen-binding region capable of binding to B7H4 having a binding affinity to human B7H4 that corresponds to a $K_D$ value of 5E-7 M or less, such as 1E-7 M or less, such as with a binding affinity corresponding to a $K_D$ value which is within the range of 5E-7 to 2E-10 M, such as within the range of 2E-7 to 1E-10 M or 1E-7 to 5E-9 M.

Said binding affinity can be determined by biolayer interferometry, optionally as set forth in Example 3 herein. Hence, the antibody according to the invention having a binding affinity to human B7H4 as defined herein, may have the binding affinity determined using biolayer interferometry comprising the steps of:

I) immobilizing the antibody at an amount of 1 μg/mL for 600 seconds on an anti-human IgG Fc Capture biosensor;

II) determining association over a time period of 300 seconds and dissociation over a time period of 1000 seconds of human recombinant His tagged B7H4 protein (Sino Biological cat no 10738-H08H; a protein expressed from a construct of DNA sequence encoding the human VTCN1 (Uniprot accession no. Q7Z7D3) (Phe29-Ala258) with a C-terminal polyhistidine tag) using a 2-fold dilution series ranging from 1.56 nM to 100 nM; and III) referencing the data to a buffer control (0 nM).

Furthermore, said binding affinity may be determined using an antibody such as a monospecific, bivalent antibody, such as an antibody which is a full length IgG1.

In a further embodiment, an antibody in accordance with the invention is provided, comprising an antigen region capable of binding to human B7H4, wherein said antigen-binding region is capable of crossblocking:
  an antibody comprising a variable heavy chain (VH) region of SEQ ID NO. 29 and a variable light chain region of SEQ ID NO. 33; and
  an antibody comprising a variable heavy chain (VH) region of SEQ ID NO. 36: and a variable light chain region of SEQ ID NO. 40; and
  wherein said antigen-binding region is not capable of crossblocking
  an antibody comprising a variable heavy chain (VH) region of SEQ ID NO. 43: and a variable light chain region of SEQ ID NO. 47;
  an antibody comprising a variable heavy chain (VH) region of SEQ ID NO. 50: and a variable light chain region of SEQ ID NO.54; and
  an antibody comprising a variable heavy chain (VH) region of SEQ ID NO. 65 and a variable light chain region of SEQ ID NO. 69.

In still another further embodiment, said antibody in accordance with the invention, comprises an antigen region capable of binding to human B7H4, said antigen-binding region capable of crossblocking
  an antibody comprising a variable heavy chain (VH) region of SEQ ID NO. 43: and a variable light chain region of SEQ ID NO. 47;
  an antibody comprising a variable heavy chain (VH) region of SEQ ID NO. 50: and a variable light chain region of SEQ ID NO.54, and
  an antibody comprising a variable heavy chain (VH) region of SEQ ID NO. 65 and a variable light chain region of SEQ ID NO. 69;
  and wherein said antigen-binding region is not capable of crossblocking an antibody comprising
  an antibody comprising a variable heavy chain (VH) region of SEQ ID NO. 29 and a variable light chain region of SEQ ID NO. 33; and
  an antibody comprising a variable heavy chain (VH) region of SEQ ID NO. 36: and a variable light chain region of SEQ ID NO. 40.

In particular, "cross-blocking", or the ability of an antibody according to the invention to block binding of another antibody to B7H4, is defined as the ability of a first antibody bound to B7H4 to block binding of a second antibody to the B7H4 bound to the first antibody. Crossblocking can be determined using an assay as described in example 5. Such crossblocking can also be determined e.g. in a procedure comprising the steps of:
  i) providing a set of samples, each sample comprising an antibody which binds to B7H4;
  ii) immobilizing a first antibody from the set of samples at an amount of 20 µg/mL for 600 seconds on Amine Reactive $2^{nd}$ Generation biosensor (AR2G);
  iii) loading the ARG2 biosensor with immobilized antibody with human B7H4 (100 nM of human recombinant His tagged B7H4 protein (Sino Biological cat no 10738-H08H; a protein expressed from a construct of DNA sequence encoding the human VTCN1 (Uniprot accession no. Q7Z7D3) (Phe29-Ala258) with a C-terminal polyhistidine tag);
  iv) determining the association of a second antibody from the set of samples at an amount of 10 µg/mL for 300 seconds.

When the second antibody is not capable of association, the first antibody is considered to cross-block the second antibody. The skilled person will be familiar with suitable technologies for determining the ability of an antibody to crossblock the binding of another antibody to its target, the present application discloses procedures suitable for determining blocking of binding and displacement. In a further embodiment, crossblocking as described herein is determined as described in Example 5.

In a further embodiment, the antibody in accordance with the invention, having an antigen-binding region capable of binding to human B7H4 complying with a crossblocking feature as described above, wherein said an antigen-binding region capable of binding to human B7H4 is capable of binding to B7H3-IgV/B7H4-IgC (SEQ ID NO. 11), and optionally is not capable of binding to B7H4-IgV/B7H3-IgC (SEQ ID NO. 10).

CD3 and B7H4 Antigen-Binding Region Combinations

The present disclosure further provides an antibody according to the invention comprising an antigen-binding region capable of binding to human B7H4 and an antigen-binding region capable of binding to human CD3, wherein the antigen-binding region that binds to CD3 comprises
  a heavy chain variable region (VH) comprising the CDR1, CDR2, and CDR3 regions of SEQ ID NO: 16, and, a light chain variable region (VL) comprising the CDR1, CDR2, and CDR3 regions of SEQ ID NO: 22, and
wherein the antigen-binding region capable of binding to B7H4 comprises:
  a) a variable heavy chain (VH) region comprising the CDR1, CDR2 and CDR3 regions of SEQ ID NO. 25: and a variable light chain region comprising the CDR1, CDR2 and CDR3 regions respectively of SEQ ID NO. 33;
  b) a variable heavy chain (VH) region comprising the CDR1, CDR2 and CDR3 regions of SEQ ID NO. 29: and a variable light chain region comprising the CDR1, CDR2 and CDR3 regions respectively of SEQ ID NO. 33;
  c) a variable heavy chain (VH) region comprising the CDR1, CDR2 and CDR3 regions of SEQ ID NO. 36: and a variable light chain region comprising the CDR1, CDR2 and CDR3 regions respectively of SEQ ID NO. 40;
  d) a variable heavy chain (VH) region comprising the CDR1, CDR2 and CDR3 regions of SEQ ID NO. 43: and a variable light chain region comprising the CDR1, CDR2 and CDR3 regions respectively of SEQ ID NO. 47;
  e) a variable heavy chain (VH) region comprising the CDR1, CDR2 and CDR3 regions of SEQ ID NO. 50: and a variable light chain region comprising the CDR1, CDR2 and CDR3 regions respectively of SEQ ID NO.54;
  f) a variable heavy chain (VH) region comprising the CDR1, CDR2 and CDR3 regions of SEQ ID NO. 31: and a variable light chain region comprising the CDR1, CDR2 and CDR3 regions respectively of SEQ ID NO. 33; or
  g) a variable heavy chain (VH) region comprising the CDR1, CDR2 and CDR3 regions of SEQ ID NO. 65: and a variable light chain region comprising the CDR1, CDR2 and CDR3 regions respectively of SEQ ID NO. 69.

The present disclosure further provides an antibody according to the invention may be an antibody comprising an antigen-binding region capable of binding to human B7H4 and an antigen-binding region capable of binding to human CD3, wherein the antigen-binding region that binds to CD3 comprises a heavy chain variable region (VH) comprising The CDR1, CDR2, and CDR3 regions of SEQ ID NO.
  17, and, a light chain variable region (VL) comprising the CDR1, CDR2, and CDR3 regions of SEQ ID NO: 22, and
wherein the antigen-binding region capable of binding to B7H4 comprises:
  a) a variable heavy chain (VH) region comprising the CDR1, CDR2 and CDR3 regions of SEQ ID NO. 25: and a variable light chain region comprising the CDR1, CDR2 and CDR3 regions respectively of SEQ ID NO. 33;
  b) a variable heavy chain (VH) region comprising the CDR1, CDR2 and CDR3 regions of SEQ ID NO. 29: and a variable light chain region comprising the CDR1, CDR2 and CDR3 regions respectively of SEQ ID NO. 33;
  c) a variable heavy chain (VH) region comprising the CDR1, CDR2 and CDR3 regions of SEQ ID NO. 36: and a variable light chain region comprising the CDR1, CDR2 and CDR3 regions respectively of SEQ ID NO. 40;
  d) a variable heavy chain (VH) region comprising the CDR1, CDR2 and CDR3 regions of SEQ ID NO. 43: and a variable light chain region comprising the CDR1, CDR2 and CDR3 regions respectively of SEQ ID NO. 47;
  e) a variable heavy chain (VH) region comprising the CDR1, CDR2 and CDR3 regions of SEQ ID NO. 50: and a variable light chain region comprising the CDR1, CDR2 and CDR3 regions respectively of SEQ ID NO.54;
  f) a variable heavy chain (VH) region comprising the CDR1, CDR2 and CDR3 regions of SEQ ID NO. 31: and a variable light chain region comprising the CDR1, CDR2 and CDR3 regions respectively of SEQ ID NO. 33; or
  g) a variable heavy chain (VH) region comprising the CDR1, CDR2 and CDR3 regions of SEQ ID NO. 65: and a variable light chain region comprising the CDR1, CDR2 and CDR3 regions respectively of SEQ ID NO. 69.

Also, the present disclosure further provides an antibody comprising an antigen-binding region capable of binding to human B7H4 and an antigen-binding region capable of binding to human CD3, wherein the antigen-binding region capable of binding to CD3 comprises:
  a heavy chain variable region (VH) comprising the CDR1, CDR2, and CDR3 sequences of SEQ ID NOs.: 18, 19 and 20 respectively; and, a light chain variable region (VL) comprising the CDR1, CDR2, and CDR3 sequences of SEQ ID NO: 23, GTN and 24, respectively; and
wherein the antigen-binding region capable of binding to B7H4 comprises:
  a) a variable heavy chain (VH) region comprising the CDR1, CDR2 and CDR3 regions respectively of SEQ ID NOs.: 26, 27 and 28, and a variable light chain region comprising the CDR1, CDR2 and CDR3 respectively of SEQ ID NO. 34, GAS and SEQ ID NO. 35;
  b) a variable heavy chain (VH) region comprising the CDR1, CDR2 and CDR3 regions respectively of SEQ ID NOs.: 26, 30 and 28, and a variable light chain region comprising the CDR1, CDR2 and CDR3 respectively of SEQ ID NO. 34, GAS and SEQ ID NO. 35;
  c) a variable heavy chain (VH) region comprising the CDR1, CDR2 and CDR3 regions respectively of SEQ ID NOs.: 37, 38 and 39, and a variable light chain region comprising the CDR1, CDR2 and CDR3 respectively of SEQ ID NO. 41, DTS and SEQ ID NO. 42;
  d) a variable heavy chain (VH) region comprising the CDR1, CDR2 and CDR3 regions respectively of SEQ ID NOs.: 44, 45 and 46, and a variable light chain region comprising the CDR1, CDR2 and CDR3 respectively of SEQ ID NO. 48, YTS and SEQ ID NO. 49;
  e) a variable heavy chain (VH) region comprising the CDR1, CDR2 and CDR3 regions respectively of SEQ ID NOs.: 51, 52 and 53, and a variable light chain region comprising the CDR1, CDR2 and CDR3 respectively of SEQ ID NO. 55, GAS and SEQ ID NO. 56;
  f) a variable heavy chain (VH) region comprising the CDR1, CDR2 and CDR3 regions respectively of SEQ ID NOs.: 26, 32 and 28, and a variable light chain region comprising the CDR1, CDR2 and CDR3 respectively of SEQ ID NO. 34, GAS and SEQ ID NO. 35; or
  g) a variable heavy chain (VH) region comprising the CDR1, CDR2 and CDR3 regions respectively of SEQ ID NOs.: 66, 67 and 68, and a variable light chain region comprising the CDR1, CDR2 and CDR3 respectively of SEQ ID NO. 70, GAS and SEQ ID NO. 71.

The present disclosure further provides an antibody comprising an antigen-binding region capable of binding to human B7H4 and an antigen-binding region capable of binding to human CD3, wherein the antigen-binding region capable of binding to CD3 comprises:
  a heavy chain variable region (VH) comprising the CDR1, CDR2, and CDR3 sequences of SEQ ID NOs.: 18, 19 and 21 respectively; and, a light chain variable region (VL) comprising the CDR1, CDR2, and CDR3 sequences of SEQ ID NO: 23, GTN and 24, respectively; and
wherein the antigen-binding region capable of binding to B7H4 comprises:
  a) a variable heavy chain (VH) region comprising the CDR1, CDR2 and CDR3 regions respectively of SEQ ID NOs.: 26, 27 and 28, and a variable light chain region comprising the CDR1, CDR2 and CDR3 respectively of SEQ ID NO. 34, GAS and SEQ ID NO. 35;
  b) a variable heavy chain (VH) region comprising the CDR1, CDR2 and CDR3 regions respectively of SEQ ID NOs.: 26, 30 and 28, and a variable light chain region comprising the CDR1, CDR2 and CDR3 respectively of SEQ ID NO. 34, GAS and SEQ ID NO. 35;
  c) a variable heavy chain (VH) region comprising the CDR1, CDR2 and CDR3 regions respectively of SEQ ID NOs.: 37, 38 and 39, and a variable light chain region comprising the CDR1, CDR2 and CDR3 respectively of SEQ ID NO. 41, DTS and SEQ ID NO. 42;
  d) a variable heavy chain (VH) region comprising the CDR1, CDR2 and CDR3 regions respectively of SEQ ID NOs.: 44, 45 and 46, and a variable light chain region comprising the CDR1, CDR2 and CDR3 respectively of SEQ ID NO. 48, YTS and SEQ ID NO. 49;
  e) a variable heavy chain (VH) region comprising the CDR1, CDR2 and CDR3 regions respectively of SEQ ID NOs.: 51, 52 and 53, and a variable light chain region comprising the CDR1, CDR2 and CDR3 respectively of SEQ ID NO. 55, GAS and SEQ ID NO. 56;
  f) a variable heavy chain (VH) region comprising the CDR1, CDR2 and CDR3 regions respectively of SEQ ID NOs.: 26, 32 and 28, and a variable light chain region comprising the CDR1, CDR2 and CDR3 respectively of SEQ ID NO. 34, GAS and SEQ ID NO. 35; or g) a variable heavy chain (VH) region comprising the CDR1, CDR2 and CDR3 regions respectively of SEQ ID NOs.: 66, 67 and 68, and a variable light chain region comprising the CDR1, CDR2 and CDR3 respectively of SEQ ID NO. 70, GAS and SEQ ID NO. 71.

Further disclosed are antibodies comprising an antigen-binding region capable of binding to human B7H4 and an antigen-binding region capable of binding to human CD3, wherein the antigen-binding region that binds to CD3 comprises:

a heavy chain variable region (VH) comprising the sequence of SEQ ID NO: 16 and, a light chain variable region (VL) comprising the sequence of SEQ ID NO: 22; and wherein the antigen-binding region capable of binding to B7H4 comprises an antigen-binding regions that bind to B7H4 comprise heavy and light chain variable regions (VH) having:

a) a variable heavy chain (VH) region of SEQ ID NO. 25: and a variable light chain region of SEQ ID NO. 33;
b) a variable heavy chain (VH) region of SEQ ID NO. 29: and a variable light chain region of SEQ ID NO. 33;
c) a variable heavy chain (VH) region of SEQ ID NO. 36: and a variable light chain region of SEQ ID NO. 40;
d) a variable heavy chain (VH) region of SEQ ID NO. 43: and a variable light chain region of SEQ ID NO. 47;
e) a variable heavy chain (VH) region of SEQ ID NO. 50: and a variable light chain region of SEQ ID NO.54;
f) a variable heavy chain (VH) region of SEQ ID NO. 31: and a variable light chain region of SEQ ID NO. 33; or
g) a variable heavy chain (VH) region of SEQ ID NO. 65: and a variable light chain region of SEQ ID NO. 69.

Still further disclosed are antibodies comprising an antigen-binding region capable of binding to human B7H4 and an antigen-binding region capable of binding to human CD3, wherein the antigen-binding region that binds to CD3 comprises:

a heavy chain variable region (VH) comprising the sequence of SEQ ID NO: 17 and, a light chain variable region (VL) comprising the sequence of SEQ ID NO: 22; and wherein the antigen-binding region capable of binding to B7H4 comprises antigen-binding heavy and light chain variable regions (VH) having:

a) a variable heavy chain (VH) region of SEQ ID NO. 25: and a variable light chain region of SEQ ID NO. 33;
b) a variable heavy chain (VH) region of SEQ ID NO. 29: and a variable light chain region of SEQ ID NO. 33;
c) a variable heavy chain (VH) region of SEQ ID NO. 36: and a variable light chain region of SEQ ID NO. 40;
d) a variable heavy chain (VH) region of SEQ ID NO. 43: and a variable light chain region of SEQ ID NO. 47;
e) a variable heavy chain (VH) region of SEQ ID NO. 50: and a variable light chain region of SEQ ID NO.54;
f) a variable heavy chain (VH) region of SEQ ID NO. 31: and a variable light chain region of SEQ ID NO. 33; or
g) a variable heavy chain (VH) region of SEQ ID NO. 65: and a variable light chain region of SEQ ID NO. 69.

In a further embodiment, in such a bispecific antibody, said antigen binding region capable of binding to human B7H4 is comprised in an heavy chain and a light chain, said heavy chain comprising said VH region and an IgG1 heavy chain constant region and said light chain comprising said VL region and a kappa light chain constant region; and wherein said antigen binding region capable of binding to human CD3 is comprised in a heavy chain and a light chain, said heavy chain comprising said VH region and an IgG1 heavy chain constant region and said light chain comprising said VL region and a lambda light chain constant region. More preferably, in such a bispecific antibody, one IgG1 heavy chain constant region is as defined in SEQ ID NO. 60 and the other is as defined in SEQ ID NO. 61, and wherein said kappa light chain constant region is as defined in SEQ ID NO. 63 and said lambda light chain constant region is as defined in SEQ ID NO. 64. It is understood that optionally, of said IgG1 heavy chain constant regions as defined in SEQ ID NO. 60 and 61, the terminal lysines can be deleted.

As will be well-known to the skilled person, each antigen-binding region of an antibody generally comprise a heavy chain variable region (VH) and a light chain variable region (VL), and each of the variable regions comprises three CDR sequences, CDR1, CDR2 and CDR3, respectively, and may comprise four framework sequences, FR1, FR2, FR3 and FR4, respectively. Each antigen-binding region of an antibody may generally comprise a heavy chain variable region (VH) and a light chain variable region (VL), and each of the variable regions comprises three CDR sequences, CDR1, CDR2 and CDR3, respectively, and may comprise four human framework sequences, FR1, FR2, FR3 and FR4, respectively.

This structure is preferably also found in the antibodies according to the present invention. Furthermore, the antibodies according to the invention may comprise two heavy chain constant regions (CH), and two light chain constant regions (CL). Examples of constant regions are provided i.a. in SEQ ID NOs. 57-64.

In particular embodiments, the antibody according to the invention comprises a first and a second heavy chain, such as a first and second heavy chain each comprising at least a hinge region, a CH2 and CH3 region. Stable, heterodimeric antibodies can be obtained at high yield for instance by so-called Fab-arm exchange as provided in WO 2008/119353 and WO 2011/131746, on the basis of two homodimeric starting proteins containing only a few, asymmetrical mutations in the CH3 regions. Hence, in some embodiments of the invention, the antibody comprises a first heavy chain wherein at least one of the amino acids at the positions corresponding to positions selected from the group consisting of T366, L368, K370, D399, F405, Y407 and K409 in a human IgG1 heavy chain has been substituted, and a second heavy chain wherein at least one of the amino acids in the positions corresponding to a position selected from the group consisting of T366, L368, K370, D399, F405, Y407, and K409 in a human IgG1 heavy chain has been substituted, wherein said substitutions of said first and said second heavy chains are not in the same positions, and wherein the amino acid positions are numbered according to Eu numbering. For example, constant domains having such a substitution are provided i.a. in SEQ ID NO. 58 and 62, which can be compared with SEQ ID NO. 57, which does not have such a substitution.

The term "amino acid corresponding to positions" as used herein refers to an amino acid position number in a human IgG1 heavy chain. Corresponding amino acid positions in other immunoglobulins may be found by alignment with human IgG1. Unless otherwise stated or contradicted by context, the amino acids of the constant region sequences are herein numbered according to the EU-index of numbering (described in Kabat, E. A. et al., 1991, Sequences of proteins of immunological interest. 5th Edition—US Department of Health and Human Services, NIH publication No. 91-3242, pp 662, 680, 689). Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

In particular embodiments, the invention provides an antibody, wherein the amino acid in the position corresponding to K409 in a human IgG1 heavy chain is R in said first heavy chain, and the amino acid in the position corresponding to F405 in a human IgG1 heavy chain is L in said second heavy chain, or vice versa.

In some embodiments, the antibody according to the present invention comprises, in addition to the antigen-binding regions, comprises an Fc region with Fc sequences of the two heavy chains. The first and second Fc sequence may each be of any isotype, including any human isotype, such as an IgG1, IgG2, IgG3, IgG4, IgE, IgD, IgM, or IgA isotype or a mixed isotype. Preferably, the Fc region is a human IgG1, IgG2, IgG3, IgG4 isotype or a mixed isotype, such as a human IgG1 isotype. In some embodiments, it is preferred that the antibody according to the invention is a full-length antibody, most preferably it is of the IgG1 type.

Antibodies according to the present invention may comprise modifications in the Fc region to render the antibody an inert, or non-activating, antibody. Hence, in the antibodies disclosed herein, one or both heavy chains may be modified so that the antibody induces Fc-mediated effector function to a lesser extent relative to an antibody which is identical, except for comprising non-modified first and second heavy chains. The Fc-mediated effector function may be measured by determining Fc-mediated CD69 expression on T cells (i.e. CD69 expression as a result of CD3 antibody-mediated, Fcγ receptor-dependent CD3 crosslinking), by binding to Fcγ receptors, by binding to C1q, or by induction of Fc-mediated cross-linking of FcγRs. In particular, the heavy chain constant sequences may be modified so that the Fc-mediated CD69 expression is reduced by at least 50%, at least 60%, at least 70%, at least 80%, at least 90%, at least 99% or 100% when compared to a wild-type (unmodified) antibody, wherein said Fc-mediated CD69 expression is determined in a PBMC-based functional assay, e.g. as described in Example 3 of WO2015001085. Modifications of the heavy and light chain constant sequences may also result in reduced binding of C1q to said antibody. As compared to an unmodified antibody the reduction may be by at least 70%, at least 80%, at least 90%, at least 95%, at least 97%, or 100% and the C1q binding may be determined by ELISA. Further, the Fc region which may be modified so that said antibody mediates reduced Fc-mediated T-cell proliferation compared to an unmodified antibody by at least 50%, at least 60%, at least 70%, at least 80%, at least 90%, at least 99% or 100%, wherein said T-cell proliferation is measured in a PBMC-based functional assay.

A wide range of different non-activating antibody formats have been developed in which amino acid substitutions, and combinations thereof, have been introduced in the constant heavy chain region of an IgG1 isotype antibody to eliminate Fc-mediated effector functions (e.g. Chiu et al., Antibodies 2019 December; 8(4): 55; Liu et al., Antibodies, 2020 Nov. 17; 9(4):64; 29(10):457-66; Shields et al., J Biol Chem., 2001 Mar. 2; 276(9):6591-604).

Examples of amino acid positions that may be modified, e.g. in an IgG1 isotype antibody, include positions L234 and L235. Hence, the antibody according to the invention may comprises a first and a second heavy chain, and wherein in both the first and the second heavy chain, the amino acid residues at the positions corresponding to positions L234 and L235 in a human IgG1 heavy chain according to Eu numbering are F and E, respectively. It is understood that in addition to modifications of amino acid positions L234 and L235, further positions may be modified.

In addition, a D265A amino acid substitution can decrease binding to all Fcγ receptors and prevent ADCC (Shields et al., 2001, J. Biol. Chem. (276):6591-604). Therefore, the antibody according to the invention may comprise a first and a second heavy chain, wherein in both the first and the second heavy chain, the amino acid residue at the position corresponding to position D265 in a human IgG1 heavy chain according to Eu numbering is A. Further embodiments of the invention provide antibodies wherein, in at least one, such as in both, of said first and second heavy chains the amino acids in the positions corresponding to positions L234, L235, and D265 in a human IgG1 heavy chain, are F, E, and A, respectively. In the present application antibodies, which have the combination of three amino acid substitutions L234F, L235E and D265A and in addition the K409R or the F405L mutation disclosed herein above may be termed with the suffix "FEAR" or "FEAL", respectively.

An amino acid sequence of a wild type IgG1 heavy chain constant region is identified herein as SEQ ID NO: 57. Consistent with the embodiments disclosed above, the antibody of the invention may comprise an IgG1 heavy chain constant region carrying the F405L substitution and may have the amino acid sequence set forth in SEQ ID NO: 58 and/or an IgG1 heavy chain constant region carrying the K409R substitution and may have the amino acid sequence set forth in SEQ ID NO: 62.

An amino acid sequence of an IgG1 heavy chain constant region carrying the L234F, L235E and D265A substitutions is identified herein as SEQ ID NO: 59. An amino acid sequence of an IgG1 heavy chain constant region carrying the L234F, L235E, D265A and F405L substitutions is identified herein as SEQ ID NO: 60. An amino acid sequence of an IgG1 heavy chain constant region carrying the L234F, L235E, D265A and K409R substitutions is identified herein as SEQ ID NO: 61.

The constant region sequences listed in SEQ ID NOs. 57-62 list a terminal lysine (K), such sequences were used in the example section herein. The origin of this lysine is a naturally occurring sequence found in humans from which these Fc regions are derived. During cell culture production of recombinant antibodies, this terminal lysine can be cleaved off by proteolysis by endogenous carboxypeptidase(s), resulting in a constant region having the same sequence but lacking the C-terminal lysine. For manufacturing purposes of antibodies, the DNA encoding this terminal lysine can be omitted from the sequence such that antibodies are produced without the lysine. Antibodies produced from nucleic acid sequences that either do, or do not encode a terminal lysine are substantially identical in sequence and in function since the degree of processing of the terminal lysine is typically high when e.g. using antibodies produced in CHO-based production systems (Dick, L. W. et al. Biotechnol. Bioeng. 2008; 100: 1132-1143). Hence, it is understood that antibodies in accordance with the invention can be generated without encoding or having a terminal lysine such as listed herein. For manufacturing purposes, antibodies can thus be generated without having a terminal lysine.

The present invention further provides an antibody, wherein a) the antigen-binding region capable of binding to B7H4 is human, and
b) the antigen-binding region capable of binding to CD3, is humanized.

Also, the invention provides an antibody, wherein a) the antigen-binding region capable of binding to B7H4 is human, and/or the antigen-binding region capable of binding to CD3, is humanized.

In some embodiments of the invention, the antibody comprises a kappa (κ) light chain. The sequence of particular embodiments of the invention concerning bispecific antibodies, the kappa light chain comprises the CDR1, -2 and -3 sequences of a B7H4 antibody light chain as disclosed above.

In further embodiments of the invention, the antibody according to any one of the preceding claims, wherein said antibody comprises a lambda (λ) light chain. In particular embodiments of the invention concerning bispecific antibodies, the lambda light chain comprises the CDR1, -2 and -3 sequences of a CD3 antibody light chain as disclosed above, in particular a the CDR1, -2 and -3 sequences of a CD3 antibody having reduced affinity for CD3 as disclosed above. The amino acid sequence of a kappa light chain constant region is included herein as SEQ ID NO: 63 and the amino acid sequence of a lambda light chain constant region is included herein as SEQ ID NO: 64.

In particular embodiments, the antibody comprises a lambda (λ) light chain and a kappa (κ) light chain; e.g. an antibody with a heavy chain and a lambda light chain which comprise the binding region capable of binding to CD3, and a heavy chain and a kappa light chain which comprise the binding region capable of binding to B7H4.

Hence, in a further embodiment, in a bispecific antibody as defined herein, said antigen binding region capable of binding to human B7H4 is comprised in a heavy chain and a light chain, said heavy chain comprising said VH region and an IgG1 heavy chain constant region and said light chain comprising said VL region and a kappa light chain constant region; and said antigen binding region capable of binding to human CD3 is comprised in a heavy chain and a light chain, said heavy chain comprising said VH region and an IgG1 heavy chain constant region and said light chain comprising said VL region and a lambda light chain constant region. More preferably, in said bispecific antibody, one IgG1 heavy chain constant region is as defined in SEQ ID NO. 60 and the other is as defined in SEQ ID NO. 61, and said kappa light chain constant region is as defined in SEQ ID NO. 63 and said lambda light chain constant region is as defined in SEQ ID NO. 64. It is understood that said IgG1 heavy chain constant regions as defined in SEQ ID NO. 60 and 61 may have their terminal lysines deleted.

Binding, Cytoxicity and T-Cell Activation

Antibodies, such as bispecific antibodies, as described herein that can bind to human CD3 and human B7H4 can advantageously target T cells to human B7H4 expressing cancer cells, thereby inducing T-cell mediated killing of said cancer cells. By having reduced or inert Fc-functionality in such antibodies, as shown in the example section, safe, effective and sufficient antibody can be administered to human patients, while being efficacious against a wide range of cancers varying in B7H4 expression levels.

As said, preferably, the antibody in accordance with the invention is devoid of, or has reduced Fc-mediated effector function, and furthermore, the antibody:

a) is capable of binding to B7H4-expressing human tumor cells as described in Example 9 and 10 herein,
b) is capable of mediating concentration-dependent cytotoxicity of B7H4-expressing human tumor cells when using e.g. purified PBMCs or T cells as effector cells when assayed as described in Example 11 and 12 herein,
c) is capable of mediating concentration-dependent cytotoxicity of one or more human B7H4-expressing tumor cell lines selected from the group consisting of MCF-7, MDA-MB-468, SK-BR3, NIH-OVCAR-3, HCC1954, and NCI-H1650, when using e.g. purified PBMCs or T cells as effector cells when assayed as described in Example 11 and 12 herein,
d) is capable of activating T cells in vitro in the presence of B7H4-expressing human tumor cells; e.g. when assayed as described in Example 13 herein,
e) is capable of activating T-cells in vitro in the presence of one or more B7H4-expressing human tumor cell lines selected from the group consisting of MCF-7, MDA-MB-468, SK-BR3, NIH-OVCAR-3, HCC1954, and NCI-H1650; e.g. when assayed as described in Example 13 herein,
f) is capable of inducing cytotoxicity of B7H4-expressing human tumor cells; e.g. when assayed as described in Example 11 and 12 herein, and/or
g) is capable of inducing T cell mediated cytotoxicity in one or more B7H4-expressing human tumor cell lines selected from the group consisting of MCF-7, MDA-MB-468, SK-BR3, NIH-OVCAR-3, HCC1954, and NCI-H1650; e.g. when assayed as described in Example 11 and 12 herein.

Furthermore, the antibody in accordance with the invention may be devoid of, or has reduced Fc-mediated effector function, and, furthermore capable of inducing T-cell mediated cytotoxicity antibody, wherein cytotoxicity is assessed in an in vitro IC50 assay comprising:

i) providing isolated peripheral blood mononuclear cells (PBMCs), or purified T-cells, from healthy human donor buffy coats;
ii) providing B7H4-expressing tumor cells, such as a human B7H4-expressing tumor cell line selected from the group consisting of MCF-7, MDA-MB-468, SK-BR3, NIH-OVCAR-3, HCC1954, and NCI-H1650;
iii) combining said PBMCs or said purified T-cells with a plurality of samples of said B7H4-expressing tumor cells, wherein the ratio of the number of T-cells from said PBMCs, or said purified T-cells, to the selected tumor cell is 8:1;
iv) providing said antibody in a dilution series to said samples, ranging e.g. from 0.0128 ng/mL to 10,000 ng/mL for a selected human B7H4 expressing tumor cell; and
v) incubating the samples obtained in step iv), e.g. for 72 hours at 37° C.; and subsequently;
vi) assessing the viability of the B7H4-expressing tumor cells;
vii) determining the percentage of viable cells for each dilution sample; and
viii) determining the IC50.

Instead of isolated peripheral blood mononuclear cells (PBMCs), purified T-cells may also be provided in step i).

Accordingly, the antibody may have an IC50 in the range of 0.001-2 microgram/ml, wherein the IC50 is determined in an in vitro cytotoxicity assay comprising the steps of:
  i) providing isolated peripheral blood mononuclear cells (PBMCs) from healthy human donor buffy coats;
  ii) providing B7H4-expressing tumor cells, such as a human B7H4-expressing tumor cell line selected from the group consisting of MCF-7, MDA-MB-468, SK-BR3, NIH-OVCAR-3, and HCC1954;
  iii) combining said PBMCs with a plurality of samples of said B7H4-expressing tumor cells, wherein the ratio of the number of T-cells from said PBMCs to the selected tumor cell is 8:1;
  iv) providing said antibody in a dilution series to said samples, ranging e.g. from 0.0128 ng/mL to 10,000 ng/mL for a selected human B7H4 expressing tumor cell; and
  v) incubating the samples obtained in step iv), e.g. for 72 hours at 37° C.; and subsequently,
  vi) assessing the viability of the B7H4-expressing tumor cells;
  vii) determining the percentage of viable cells for each dilution sample; and
  viii) determining the IC50.

Accordingly, the antibody may have an IC50 in the range of 0.001-5 microgram/ml, wherein the IC50 is determined in an in vitro cytotoxicity assay comprising the steps of:
  i) providing isolated peripheral blood mononuclear cells (PBMCs), or purified T-cells, from healthy human donor buffy coats;
  ii) providing B7H4-expressing tumor cells, such as a human B7H4-expressing tumor cell line selected from the group consisting of MCF-7, MDA-MB-468, SK-BR3, NIH-OVCAR-3, HCC1954, and NCI-H1650;
  iii) combining said PBMCs or said purified T-cells with a plurality of samples of said B7H4-expressing tumor cells, wherein the ratio of the number of T-cells from said PBMCs, or said purified T-cells, to the selected tumor cell is 8:1;
  iv) providing said antibody in a dilution series to said samples, ranging e.g. from 0.0128 ng/mL to 10,000 ng/mL for a selected human B7H4 expressing tumor cell; and
  v) incubating the samples obtained in step iv), e.g. for 72 hours at 37° C.; and subsequently,
  vi) assessing the viability of the B7H4-expressing tumor cells;
  vii) determining the percentage of viable cells for each dilution sample; and
  viii) determining the IC50.

In one embodiment, the antibody in accordance with the invention may have an IC50 in the range of 0.001-5 microgram/ml. In one embodiment, the antibody in accordance with the invention may have an IC50 in the range of 0.001-2 microgram/ml. In another embodiment, the antibody in accordance with the invention may have an IC50 is in the range of 0.001-0.03 microgram/ml. In still a further embodiment, the IC50 may be in the range of 0.05-2 microgram/ml. In yet another further embodiment, the IC50 may be in the range of 0.05-5 microgram/ml. Said IC50 may be determined using a method such as described in Example 12.

In a further embodiment, the ability of the antibody in accordance with the invention to mediate T cell activation is determined in an in vitro assay comprising the steps of:
  i) providing isolated peripheral blood mononuclear cells (PBMCs) from healthy human donor buffy coats;
  ii) providing B7H4-expressing tumor cells;
  iii) combining PBMCs and B7H4-expressing tumor cells in a plurality of samples, wherein the ratio of the number of PBMCs to tumor cells is 8:1;
  iv) providing said antibody in a dilution series to said samples, ranging e.g. from 0.0128 ng/mL to 10,000 ng/mL;
  v) incubating the samples, e.g. for 72 hours at 37° C.; and
  vi) subsequently detecting cytokines.

Exemplary cytokines that can be e.g. detected are e.g. IFN-γ, such as e.g. described in example 13. Preferably B7H4-expressing tumor cells are human B7H4-expressing tumors, such as primary tumors, or tumor cell lines selected from the group consisting of MCF-7, MDA-MB-468, SK-BR3, NIH-OVCAR-3, and HCC1954.

B7H4 Antibodies

In another embodiment, an antibody is provided comprising an antigen-binding region capable of binding to human B7H4, wherein said antigen-binding region capable of binding to human B7H4 comprises:
  a) a variable heavy chain (VH) region comprising the CDR1, CDR2 and CDR3 regions of SEQ ID NO. 25: and a variable light chain region comprising the CDR1, CDR2 and CDR3 regions respectively of SEQ ID NO. 33;
  b) a variable heavy chain (VH) region comprising the CDR1, CDR2 and CDR3 regions of SEQ ID NO. 29: and a variable light chain region comprising the CDR1, CDR2 and CDR3 regions respectively of SEQ ID NO. 33;
  c) a variable heavy chain (VH) region comprising the CDR1, CDR2 and CDR3 regions of SEQ ID NO. 31: and a variable light chain region comprising the CDR1, CDR2 and CDR3 regions respectively of SEQ ID NO. 33;
  d) a variable heavy chain (VH) region comprising the CDR1, CDR2 and CDR3 regions respectively of SEQ ID NOs.: 26, 27 and 28, and a variable light chain region comprising the CDR1, CDR2 and CDR3 respectively of SEQ ID NO. 34, GAS and SEQ ID NO. 35;
  e) a variable heavy chain (VH) region comprising the CDR1, CDR2 and CDR3 regions respectively of SEQ ID NOs.: 26, 30 and 28, and a variable light chain region comprising the CDR1, CDR2 and CDR3 respectively of SEQ ID NO. 34, GAS and SEQ ID NO. 35;
  f) a variable heavy chain (VH) region comprising the CDR1, CDR2 and CDR3 regions respectively of SEQ ID NOs.: 26, 32 and 28, and a variable light chain region comprising the CDR1, CDR2 and CDR3 respectively of SEQ ID NO. 34, GAS and SEQ ID NO. 35;
  g) a variable heavy chain (VH) region of SEQ ID NO. 25: and a variable light chain region of SEQ ID NO. 33;
  h) a variable heavy chain (VH) region of SEQ ID NO. 29: and a variable light chain region of SEQ ID NO. 33;
  i) a variable heavy chain (VH) region of SEQ ID NO. 31: and a variable light chain region of SEQ ID NO. 33; or
  j) having a heavy (VH) and light (VH) chain variable regions having at least 90%, at least 95%, at least 97%, or at least 99% amino acid sequence identity with the respective variable heavy chain (VH) region of SEQ ID NO. 25 and the variable light chain region of SEQ ID NO. 33.

Such antibodies do not necessarily comprise an antigen-binding region that binds to CD3. Such antibodies may be useful, e.g. in kits and assays for detecting B7H4. Such antibodies may also be useful in the treatment of cancer.

Hence, such an antibody may be monospecific antibody binding to B7H4. Such an antibody may be a bivalent antibody.

Preferably, such an antibody is an antibody comprising a heavy chain constant region which is a human IgG1 constant region. For example, a heavy chain constant region such as listed in SEQ ID NO. 57-62. A preferred light chain constant region is a kappa light chain, such as listed in SEQ ID NO. 63.

In one embodiment, the antibody provided herein may bind to an epitope or antibody binding region on human B7H4 comprising one or more of the amino acid residues S151, V157, D158, Y159, E164, L166, W173, P175, P177, V179, W181, F199, M208, V210, T222, Y223, V240, E242 and I245; the numbering of each amino acid residue referring to its position in SEQ ID NO: 1. In a further embodiment, the antibody provided herein may bind to an epitope or antibody binding region on human B7H4 comprising one or more of the amino acid residues V157, D158, Y159, E164, L166; the numbering of each amino acid residue referring to its position in SEQ ID NO: 1.

In another embodiment, the antibody provided herein may bind to an epitope or antibody binding region on human B7H4 comprising the amino acid residues S151, V157, D158, Y159, E164, L166, W173, P175, P177, V179, W181, F199, M208, V210, T222, Y223, V240, E242 and I245; the numbering of each amino acid residue referring to its position in SEQ ID NO: 1. In a further embodiment, the antibody provided herein may bind to an epitope or antibody binding region on human B7H4 comprising the amino acid residues V157, D158, Y159, E164, L166; the numbering of each amino acid residue referring to its position in SEQ ID NO: 1.

Based on the results provided in Example 7 herein it is hypothesized, without any wish to be bound by theory, that any one or more of these amino acid residues (i.e. S151, V157, D158, Y159, E164, L166, W173, P175, P177, V179, W181, F199, M208, V210, T222, Y223, V240, E242 and I245) is/are directly involved in binding of the antibody, such as by way of non-covalent interactions; e.g with amino acid residues within the CDR sequences of the antibody.

The amino acid residues comprised by said epitope or antibody binding region and optionally the one or more additional amino acid residues which are indirectly involved in binding may be identified by alanine scanning of human B7H4 having the amino acid sequence set forth in SEQ ID NO: 1 or the extracellular domain sequence of SEQ ID NO: 1. The alanine scanning may in particular be performed as set forth or essentially as set forth in Example 7 herein.

Further, the alanine scanning may be performed by a procedure comprising the steps of:
i) Expressing mutant human B7H4 polypeptides in which amino acid residues in the extracellular domain of human B7H4, except cysteines and alanines, are individually substituted with alanine, and corresponding wild type B7H4 polypeptides individually in human embryonic kidney cells, e.g. HEK 293 cells, such that for each mutant or wild type B7H4 a sample comprising 40-60.000 cells, such as 50.000 cells is provided,
ii) Incubating the cells in each sample with 20 µL of said antibody, wherein said antibody consists of a single heavy chain and a single light chain, which antibody is labelled, e.g. with a suitable label for flow cytometry analysis such as an mNeogreen label, and incubated for an hour at room temperature, and subsequently washing with FACS buffer (e.g. phosphate-buffered saline [PBS; Lonza, cat. no. BE17-517]+0.1% [w/v] BSA [Roche, cat. no. 10735086001]+0.02% [w/v] sodium azide [Na N3; EMELCA Bioscience, cat. no. 41920044-3]) and resuspending the cells in each sample in 30 µL FACS buffer,
iii) Determining, for each sample, the average amount of antibody bound per cell as the geometric mean of the fluorescence intensity (gMFI) for the viable, single cell population in said sample and normalizing the data for each test antibody against the binding intensity of a non-cross blocking B7H4-specific reference antibody using the equation:

$$\text{Normalized} gMFI_{aa\ position} = \text{Log}_{10}\left(\frac{gMFI_{Test\ Ab}}{gMFI_{Control\ Ab}}\right)$$

wherein 'aa position' refers to the position that was mutated into an alanine,
wherein the fold-change or Z-score is calculated to express loss or gain of binding of the antibody, according to the calculation:

$$\text{Fold Change} = \text{Log}_{10}\left(\frac{\text{Normalized} gMFI_{ala\ mutant}}{\text{Normalized} gMFI_{wt}}\right)$$

wherein amino acid positions for which, upon replacing the amino acid with alanine, there is no loss or gain of binding by a particular antibody will give as result '0', and gain of binding will result in '>0' and loss of binding will result in '<0', and wherein, only B7H4 amino acid residues where the Fold Change in binding was lower than the mean Fold Change—1.5×SD, where SD is the standard deviation of calculated fold changes from four independent experiments for a particular test antibody, were considered 'loss of binding mutants', and, wherein, in case the gMFI of the reference antibody for a particular B7H4 mutant was lower than the mean gMFI—2.5×SD of the mean gMFI Control Ab, data were excluded from analysis.

Furthermore, such an antibody may also be a bispecific antibody comprising in addition to an antigen-binding region capable of binding to B7H4 another antigen-binding region. Such another antigen-binding region may be an antigen-binding region capable of binding to human CD3. Such antigen-binding region capable of binding to human CD3 may be antigen-binding regions capable of binding to CD3 as described and disclosed herein.

In a further embodiment, in such a bispecific antibody, said antigen binding region capable of binding to human B7H4 is comprised in an heavy chain and a light chain, said heavy chain comprising said VH region and an IgG1 heavy chain constant region and said light chain comprising said VL region and a kappa light chain constant region; and wherein said antigen binding region capable of binding to human CD3 is comprised in a heavy chain and a light chain, said heavy chain comprising said VH region and an IgG1 heavy chain constant region and said light chain comprising said VL region and a lambda light chain constant region. More preferably, in such a bispecific antibody, one IgG1 heavy chain constant region is as defined in SEQ ID NO. 60 and the other is as defined in SEQ ID NO. 61, and wherein said kappa light chain constant region is as defined in SEQ ID NO. 63 and said lambda light chain constant region is as defined in SEQ ID NO. 64. It is understood that optionally, of said IgG1 heavy chain constant regions as defined in SEQ ID NO. 60 and 61, the terminal lysines can be deleted.

A highly preferred bispecific antibody in accordance with the invention is as described and used in the example section, and is referred to as BsIgG1-huCD3-H101G-FEALxB7H4-C1-N52S-FEAR.

Hence, In a preferred embodiment, a bispecific antibody capable of binding human CD3 and human B7H4 is provided comprising:
a first heavy chain and a first light chain which comprise the binding region capable of binding to human CD3, wherein said first heavy chain comprises a heavy chain variable region as defined by SEQ ID NO: 17 and a human IgG1 heavy chain constant region as defined herein, and wherein said first light chain comprises a light chain variable region as defined by SEQ ID NO: 22 and a human lamba light chain constant region; and
a second heavy chain and a second light chain which comprise the binding region capable of binding to human B7H4, wherein said second heavy chain comprises a heavy chain variable region as defined by SEQ ID NO: 29 and a human IgG1 heavy chain constant region as defined herein, and wherein said second light chain comprises a light chain variable region as defined by SEQ ID NO: 33 and a human kappa light chain constant region.

It is understood that the human IgG1 heavy chain constant regions as defined herein may encompass substitutions as defined herein (e.g. FEAR/FEAL), or the like. It is also understood that the human IgG1 heavy chain constant region may have its terminal lysine (K) deleted.

In a further preferred embodiment, a bispecific antibody capable of binding human CD3 and human B7H4 is provided comprising:
a first heavy chain and a first light chain which comprise the binding region capable of binding to human CD3, wherein said first heavy chain comprises a heavy chain variable region as defined by SEQ ID NO: 17 and a heavy chain constant region as defined by SEQ ID NO: 60, and wherein said first light chain comprises a light chain variable region as defined by SEQ ID NO: 22 and a light chain constant region as defined by SEQ ID NO: 64; and
a second heavy chain and a second light chain which comprise the binding region capable of binding to human B7H4, wherein said second heavy chain comprises a heavy chain variable region as defined by SEQ ID NO: 29 and a heavy chain constant region as defined by SEQ ID NO: 61, and wherein said second light chain comprises a light chain variable region as defined by SEQ ID NO: 33 and a light chain constant region as defined by SEQ ID NO: 63.

Likewise, it is understood that the human IgG1 heavy chain constant region may have its terminal lysine (K) deleted.

In yet another further preferred embodiment, a bispecific antibody capable of binding human CD3 and human B7H4 is provided comprising:
a first heavy chain and a first light chain which comprise the binding region capable of binding to human CD3, wherein said first heavy chain consists of a heavy chain variable region as defined by SEQ ID NO: 17 and a heavy chain constant region as defined by SEQ ID NO: 60, and wherein said first light chain consists of a light chain variable region as defined by SEQ ID NO: 22 and a light chain constant region as defined by SEQ ID NO: 64; and
a second heavy chain and a second light chain which comprise the binding region capable of binding to human B7H4, wherein said second heavy chain consists of a heavy chain variable region as defined by SEQ ID NO: 29 and a heavy chain constant region as defined by SEQ ID NO: 61, and wherein said second light chain consists of a light chain variable region as defined by SEQ ID NO: 33 and a light chain constant region as defined by SEQ ID NO: 63.

In another further preferred embodiment, a bispecific antibody capable of binding human CD3 and human B7H4 is provided comprising:
a first heavy chain and a first light chain which comprise the binding region capable of binding to human CD3, wherein said first heavy chain consists of a heavy chain variable region as defined by SEQ ID NO: 17 and a heavy chain constant region as defined by SEQ ID NO: 60 with the terminal lysine (K) deleted, and wherein said first light chain consists of a light chain variable region as defined by SEQ ID NO: 22 and a light chain constant region as defined by SEQ ID NO: 64; and
a second heavy chain and a second light chain which comprise the binding region capable of binding to human B7H4, wherein said second heavy chain consists of a heavy chain variable region as defined by SEQ ID NO: 29 and a heavy chain constant region as defined by SEQ ID NO: 61 with the terminal lysine (K) deleted, and wherein said second light chain consists of a light chain variable region as defined by SEQ ID NO: 33 and a light chain constant region as defined by SEQ ID NO: 63.

Methods of Preparing Bispecific Antibodies

Traditional methods such as the hybrid hybridoma and chemical conjugation methods (Marvin and Zhu (2005) Acta Pharmacol Sin 26:649) can be used in the preparation of the bispecific antibodies of the invention. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific, product, upon co-expression of different antibody constructs can also be used, e.g., the method described by Lindhofer et al. (1995 J Immunol 155:219). Fusion of rat and mouse hydridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing the bispecific CD3xB7H4 antibodies of the present invention includes methods described in WO2011131746 and WO13060867 (Genmab) comprising the following steps:

a) providing a first antibody comprising an Fc region, said Fc region comprising a first CH3 region;

b) providing a second antibody comprising a second Fc region, said Fc region comprising a second CH3 region, wherein the first antibody is a CD3 antibody and the second antibody is a B7H4 antibody, or vice versa;

wherein the sequences of said first and second CH3 regions are different and are such that the heterodimeric interaction between said first and second CH3 regions is stronger than each of the homodimeric interactions of said first and second CH3 regions;

c) incubating said first antibody together with said second antibody under reducing conditions; and d) obtaining said bispecific CD3xB7H4 antibody.

In one embodiment, the said first antibody together with said second antibody are incubated under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies are reduced and the resulting cysteines are then able to form inter heavy-chain disulfide bond with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a further embodiment, step c) comprises restoring the conditions to become non-reducing or less reducing, for example by removal of a reducing agent, e.g. by desalting.

For this method any of the CD3 and B7H4 antibodies described herein may be used. In a particular embodiment the CD3 and B7H4 antibodies, respectively, may be chosen so as to obtain a bispecific CD3xB7H4 antibody as described herein.

In one embodiment of this method, said first and/or second antibodies are full-length antibodies.

The Fc regions of the first and second antibodies may be of any isotype, including, but not limited to, IgG1, IgG2, IgG3 or IgG4. In one embodiment of this method, the Fc regions of both said first and said second antibodies are of the IgG1 isotype. In another embodiment, one of the Fc regions of said antibodies is of the IgG1 isotype and the other of the IgG4 isotype. In the latter embodiment, the resulting bispecific antibody comprises an Fc region of an IgG1 and an Fc region of IgG4 and may thus have interesting intermediate properties with respect to activation of effector functions.

In a further embodiment, one of the antibody starting proteins has been engineered to not bind Protein A, thus allowing to separate the heterodimeric protein from said homodimeric starting protein by passing the product over a protein A column.

As described above, the sequences of the first and second CH3 regions of the homodimeric starting antibodies are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference in their entirety.

In particular, a stable bispecific CD3xB7H4 antibody can be obtained at high yield using the above method of the invention on the basis of two homodimeric starting antibodies which bind CD3 and B7H4, respectively, and contain only a few, fairly conservative, asymmetrical mutations in the CH3 regions. Asymmetrical mutations mean that the sequences of said first and second CH3 regions contain amino acid substitutions at non-identical positions.

The bispecific antibodies of the invention may also be obtained by co-expression of constructs encoding the first and second polypeptides in a single cell.

Thus, in a further aspect, the invention relates to a method for producing a bispecific antibody, said method comprising the following steps:

a) providing a first nucleic-acid construct encoding a first polypeptide comprising a first Fc region and a first antigen-binding region of a first antibody heavy chain, said first Fc region comprising a first CH3 region, b) providing a second nucleic-acid construct encoding a second polypeptide comprising a second Fc region and a second antigen-binding region of a second antibody heavy chain, said second Fc region comprising a second CH3 region, wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407, optionally wherein said first and second nucleic acid constructs encode light chain sequences of said first and second antibodies c) co-expressing said first and second nucleic-acid constructs in a host cell, and d) obtaining said heterodimeric protein from the cell culture.

Thus, the present invention also relates to a recombinant eukaryotic or prokaryotic host cell which produces a bispecific antibody of the present invention.

Suitable expression vectors, including promoters, enhancers, etc., and suitable host cells for the production of antibodies are well-known in the art. Examples of host cells include yeast, bacterial and mammalian cells, such as CHO or HEK cells.

In embodiment, a method for producing an antibody capable of binding to both B7H4 and CD3 in accordance with the invention is provided, comprising the steps of:
a) providing an antibody capable of binding to B7H4, said antibody comprising an antigen-binding region capable of binding to B7H4 as defined herein;
b) providing an antibody capable of binding to CD3, said antibody comprising an antigen-binding region capable of binding to CD3 as defined herein;
c) incubating said antibody capable of binding to B7H4 together with said antibody capable of binding to CD3 under reducing conditions sufficient to allow cysteines in the hinge region to undergo disulfide-bond isomerization; and
d) obtaining said antibody capable of binding to B7H4 and CD3.

In such methods, the steps of providing an antibody capable of binding to B7H4 and/or CD3, may comprise the steps of
providing cells containing expression vectors for producing said antibody or said antibodies; and
allowing the cells to produce said antibody or said antibodies and subsequently,
obtaining said antibody or said antibodies, thereby providing said antibody or said antibodies The invention furthermore provides for
a) a nucleic acid sequence encoding a heavy chain sequence of an antigen-binding region capable of binding to B7H4 as defined herein, and/or
b) a nucleic acid sequence encoding the corresponding light chain sequence of the antigen-binding region capable of binding to B7H4.

Furthermore, the invention provides for one or more nucleic acids comprising:
a) a nucleic acid sequence encoding a heavy chain sequence of an antigen-binding region capable of binding to B7H4 as defined herein,
b) a nucleic acid sequence encoding the corresponding light chain sequence of said antigen-binding region capable of binding to B7H4,
c) a nucleic acid sequence encoding a heavy chain sequence of an antigen-binding region capable of binding to CD3 as defined herein, and
d) a nucleic acid sequence encoding the corresponding light chain sequence of said antigen-binding region capable of binding to CD3.

The nucleic acid, or one or more nucleic acids, as defined herein can be RNA or DNA. The nucleic acid, or one or more nucleic acids, as defined herein may be for use in expression in mammalian cells. Hence, furthermore the invention provides for a cell or cells, comprising a nucleic acid, or comprising one or more nucleic acids, as defined herein.

The nucleic acid in the context of the present invention may be an expression vector, which may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a B7H4 or a CD3 antibody-encoding nucleic acid is comprised in a naked DNA or RNA vector, including, for example, a linear expression element (as described in for instance Sykes and Johnston, Nat Biotech 17, 355 59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793 800 (2001)), or as a precipitated nucleic acid vector construct, such as a CaPO4-precipitated construct (as described in for instance WO200046147, Benvenisty and Reshef, PNAS USA 83, 9551 55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the B7H4 antibody and/or the CD3 antibody in a bacterial cell. Examples of such vectors include expression vectors such as BlueScript (Stratagene), pIN vectors (Van Heeke & Schuster, J Biol Chem 264, 5503 5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

A nucleic acid and/or expression vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides. The nucleic acid and/or expression vector may comprise any suitabale elements facilitating expression, i.e. transcription and/or translation of the nucleic acid such that the components of the (bispecific) antibodies are expressed. The nucleic acid and/or vector be associated with any suitable promoter, enhancer, and other expression-facilitating elements. Examples of such elements include strong expression promoters (e. g., human CMV IE promoter/enhancer as well as RSV, SV40, SL3 3, MMTV, and HIV LTR promoters), effective poly (A) termination sequences, an origin of replication for plasmid product in $E.\ coli$, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the B7H4 and/or CD3 antibody-encoding expression vector may be positioned in and/or delivered to a cell. Hence, in a further aspect, the invention relates to a host cell comprising the nucleic acid or vector as defined herein. The cell may be of human origin, such as a human embryonic kidney (HEK) cell, such as a HEK/Expi cell, or can be of rodent origin, such as a Chinese hamster ovary cell, such as a CHO/N50 cell.

Compositions and (Medical) Uses

Furthermore, the invention provides for a composition comprising an antibody as defined herein. Preferably, such a composition is a pharmaceutical composition, i.e. the antibody is comprised in a pharmaceutically acceptable carrier. The pharmaceutical composition of the present invention may contain a bispecific antibody of the present invention targeting both B7H4 and CD3. The pharmaceutical composition may also comprise an antibody targeting B7H4. The pharmaceutical composition may also comprise a combination of antibodies, including an antibody targeting B7H4 and/or a bispecific antibody in accordance with the present invention.

A pharmaceutical composition may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e. g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

The antibody, composition, or pharmaceutical composition in accordance with the invention is preferably for use as a medicament. The antibody, composition, or pharmaceutical composition in accordance with the invention is preferably for use in the treatment of disease. Bispecific antibodies of the invention may be used for a number of purposes. In particular, the bispecific antibodies of the invention may be used for the treatment of various forms of cancer, including metastatic cancer and refractory cancer. Preferably, the cancer may be of the solid tumor type.

In particular, the bispecific antibodies according to the invention may be useful in therapeutic settings in which specific targeting and T cell-mediated killing of cells that express B7H4 is desired.

In one embodiment, the present invention provides a method for treating a cancer in a subject, which method comprises administration of a therapeutically effective amount of a bispecific B7H4xCD3 antibody of the present invention. In a further embodiment, the present invention provides a method for treating a disorder involving cells expressing B7H4, in a subject, which method comprises administration of a therapeutically effective amount of a bispecific antibody of the present invention.

In another embodiment, the present invention provides a method for treating a cancer in a subject, which method comprises administration of a therapeutically effective amount of an antibody capable of binding to human B7H4 of the present invention. In a further embodiment, the present invention provides a method for treating a disorder involving cells expressing B7H4, in a subject, which method comprises administration of a therapeutically effective amount of a monospecific antibody of the present invention that is capable of binding to human B7H4.

As said, suitable diseases that can be contemplated in methods and uses in accordance with the invention are cancer. Said cancer most preferably is characterized by expression of B7H4. Expression of B7H4 in a cancer can easily be determined using methods known in the art, such as PCR, immunostaining, or FACS analysis, i.e. detecting expression of B7H4 transcript and/or protein. The antibodies as described herein that are capable of binding to human B7H4 may be used e.g. in immunostaining and/or FACS analysis or the like.

Cancers that can express B7H4 include Breast cancer, Uterine/endometrial cancer, Uterine carcinosarcoma cancer, Ovarian cancer, Cervical cancer, Non-small cell lung cancer (squamous cell carcinoma and adenocarcinoma), Head and neck squamous cell carcinoma, Bladder cancer, esophageal cancer, cholangiocarcinoma, Pancreatic cancer, Stomach cancer, Renal cancer and Prostate cancer.

Cancers that can express B7H4 include cancers such as cancers of the stomach, cholangiocarcinoma, bladder cancer, non small cell lung cancer (in particular squamous NSCLC), pancreatic cancer, cervical cancer, head and neck cancer, breast cancer (including triple negative breast cancer), ovarian cancer and uterine cancer. Types of cancers that may be preferred are cancers selected from uterine carcinosarcoma (UCS), bladder urothelial carcinoma (BLCA), pancreatic adenocarcinoma (PAAD), lung squamous cell carcinoma (LUSC), breast invasive carcinoma (BRCA), uterine corpus endometrial carcinoma (UCEC), ovarian serous cystadenocarcinoma (OV) and cholangiocarcinoma (CHOL).

In a further embodiment, a patient being diagnosed with cancer may be subjected to an assessment of B7H4 expression in the cancer cells, and when B7H4 is detected, which may be in the range from low to high, such a patient may be selected for treatment with an antibody in accordance with the invention. Patients diagnosed with having cancer of the stomach, cholangiocarcinoma, bladder cancer, non small cell lung cancer (in particular squamous NSCLC), pancreatic cancer, cervical cancer, head and neck cancer, breast cancer (including triple negative breast cancer), ovarian cancer or uterine cancer, may be subjected to such test. In a further embodiment, a patient being diagnosed with having uterine carcinosarcoma (UCS), bladder urothelial carcinoma (BLCA), pancreatic adenocarcinoma (PAAD), lung squamous cell carcinoma (LUSC), breast invasive carcinoma (BRCA), uterine corpus endometrial carcinoma (UCEC), ovarian serous cystadenocarcinoma (OV) or cholangiocarcinoma (CHOL), may be subjected to such test. However, it may not necessarily be a requirement to include such an assessment in selecting a patient for treatment.

Kits

The invention further provides a kit-of-parts comprising an antibody as disclosed above, such as a kit for use as a companion diagnostic/for identifying within a population of patients, those patients which have a propensity to respond to treatment with an antibody as defined herein above or an immunoconjugate or antibody-drug conjugate (ADC) as defined herein above, or for predicting efficacy or anti-tumor activity of said antibody or immunoconjugate or ADC when used in treatment of a patient, the kit comprising an antibody as defined above; and instructions for use of said kit.

A kit-of-parts, such as a kit for use as a companion diagnostic/for identifying within a population of patients those patients which have a propensity to respond to treatment with an antibody as defined in any one of claims 1 to 55, comprising an antibody as defined in any one of claims 1 to 55; and instructions for use of said kit.

Hence, in one aspect, the invention relates to a diagnostic composition comprising a bispecific CD3xB7H4 antibody as defined herein, or a B7H4 antibody as defined herein, and to its use.

In another aspect, the invention relates to a kit for detecting cross-linking between CD3- and B7H4 expressing cells, in a sample derived from a patient, comprising
i) a bispecific antibody according to any one of the embodiments as disclosed herein; and
ii) instructions for use of said kit.

In one embodiment, the present invention provides a kit for diagnosis of cancer comprising a container comprising a bispecific CD3xB7H4 antibody, and one or more reagents for detecting cross-linking of B7H4 expressing cells and CD3 expressing cells. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

In a further aspect, the invention relates to a method for detecting whether cross-linking between CD3- and B7H4-expressing cells occurs in a sample derived from a patient, upon administration of a bispecific antibody according to any one of the embodiments as disclosed herein, comprising the steps of:

(i) contacting the sample with a bispecific antibody according to any one of the embodiments as disclosed herein under conditions that allow for formation of a complex between said bispecific antibody and the CD3-expressing cells and the B7H4-expressing cells; and (ii) analyzing whether a complex has been formed.

The present invention is further illustrated by the following examples, which should not be construed as limiting the scope of the invention.

Example 1—Generation of B7H4 Antibodies and Screenings Materials

Expression of B7H4 Constructs

Constructs encoding various full length B7H4 variants were generated: human (*Homo sapiens*) B7H4 (Uniprot accession no. Q7Z7D3), cynomolgus monkey (*Macaca fascicularis*) B7H4 transcript 1 (Uniprot accession no. A0A2K5U6P5), dog (*Canis familiaris*) B7H4 (Uniprot accession no. F1P8R9), rabbit (*Oryctolagus cuniculus*) B7H4 (Uniprot accession no. G1TQE8), rat (*Rattus norvegicus*) B7H4 (Uniprot accession no. Q501W4), mouse (*Mus musculus*) B7H4 (Uniprot accession no. Q7TSP5), and pig (*Sus scrofa*) B7H4 (Uniprot accession no. F1SAY4) (see Table 1).

In addition, a construct for the extracellular domain (ECD) of human B7H4 (aa 25-259 from Uniprot accession no. Q7Z7D3) fused to human IgG1 Fc domain with a C-terminal His tag and C tag (B7H4ECD-FcHisC) (SEQ ID NO: 12) was generated. In SEQ ID NO: 1, amino acid residues 1-24 are a signal peptide; hence the mature B7H4ECD-FcHisC protein corresponds to amino acid residues 25-259 of SEQ ID NO: 1.

Constructs contained suitable restriction sites for cloning and an optimal Kozak (GCCGCCACC) sequence (Kozak, M., Gene 1999; 234(2):187-208). The full length and ECD of B7H4 constructs were cloned in pSB, a mammalian expression vector containing Sleeping Beauty inverted terminal repeats flanking an expression cassette consisting of a CMV promoter and HSV-TK polyA signal.

Generation of HEK-293F Cell Lines Transiently Expressing Full Length B7H4 Variants Freestyle™ 293-F (a HEK-293 subclone adapted to suspension growth and chemically defined Freestyle medium [HEK-293F]) cells were obtained from Invitrogen (cat. no. R790-07) and transfected with the constructs described supra, using 293fectin (Invitrogen, cat. no. 12347-019) according to the manufacturer's instructions.

Purification of His-Tagged B7H4

B7H4ECD-FcHisC was expressed using the Expi293F expression platform (Thermo Fisher Scientific, Waltham, Mass., USA, cat. no. A14527) essentially as described by the manufacturer.

The His-tag enables purification with immobilized metal affinity chromatography Ni-NTA. The His-tagged protein binds strongly to the column material, while other proteins present in the culture supernatant do not bind or bind weakly compared to the His-tagged proteins and elute in the flow-through. The column was washed in order to remove weakly bound proteins. The strongly bound His-tagged proteins were then eluted with a buffer containing imidazole, which competes with the binding of His to $Ni^{2+}$. The eluent was removed by buffer exchange on a desalting column.

Immunization

OmniRat® animals (transgenic rats expressing a diversified repertoire of antibodies with fully human idiotypes; Ligand Pharmaceuticals Inc., San Diego, USA) were immunized by subcutaneous injections in the hocks of both hind legs (twice weekly for 7 weeks) with 50 µg B7H4ECD-FcHisC in PBS mixed with an equal volume of adjuvant (Sigma adjuvant system (Sigma-Aldrich, St. Louis, Mo., USA, cat. no. S6322) or CFA, Complete Freund Adjuvant ($1^{st}$ injection) and IFA, Incomplete Freund Adjuvant (Sigma-Aldrich, St. Louis, Mo., USA, cat. no. F5881/F5506) (subsequent injections), followed by a final boost s.c. injection of antigen in PBS without adjuvant.

Antibody Generation

Lymph node cells from immunized animals were fused to mouse myeloma SP2.0 cells according to standard procedures 3 days after the final boost. RNA from hybridomas producing B7H4 specific antibody was extracted and 5'-RACE-complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the p33G1f, p33Kappa and p33Lambda expression vectors (pcDNA3.3 based vectors with codon optimized human IgG1m(f), Kappa and Lambda constant domains respectively), by ligation independent cloning (Aslanidis, C. and P. J. de Jong, Nucleic Acids Res 1990; 18(20): 6069-74). The variable domains from these expression vectors were sequenced and CDRs were annotated according to IMGT definitions (Lefranc M P. et al., Nucleic Acids Research, 27, 209-212, 1999 and Brochet X. Nucl. Acids Res. 36, W503-508 (2008)). Clones with a correct Open Reading Frame (ORF) were expressed and tested for binding to the antigen. After antigen specific screening assay was performed, the sequences of variable regions of heavy and light chain were gene synthesized and cloned into an expression vector including a human IgG1 heavy chain containing the following amino acid mutations: L234F, L235E, D265A and K409R (FEAR) wherein the amino acid position number is according to Eu numbering (correspond to SEQ ID NO 60), and into expression vectors including human kappa or lambda light chain. For some of the antibodies, a variant with point mutation in the variable domains was generated to remove a cysteine residue, which potentially could generate undesired disulphide bridge formation, or to replace an Asparagine to Serine or germline residue to remove a potential N-linked glycosylation site. For example, from the C1 heavy and light chain variable region sequences, a variant with an N52S substitution was made corresponding with a substitution in CDR2 (see TABLE 1, SEQ ID NOs. 25 and 29), and a further variant can have an N52Q substitution (SEQ ID NO. 31).

Antigen Specific Screening Assay

The presence of B7H4 antibodies in sera of immunized animals, or hybridoma and transfectoma culture supernatant was determined in a homogeneous binding assay. Samples were analyzed for binding of antibodies to HEK-293F cells transiently transfected with the constructs made to express full length B7H4 variants expressing human B7H4, cynomolgus monkey B7H4 or murine B7H4, or HEK-293F wild-type cells (negative control). Samples were added to the cells to allow antibody binding to B7H4. Subsequently, antibody binding was detected using an appropriate fluorescent conjugate (AffiniPure Goat Anti-Rat IgG (H+L) Alexa Fluor® 647; Jackson ImmunoResearch, cat no. 112-605-143; AffiniPure Goat Anti-Human IgG Fc gamma-Alexa Fluor® 647; Jackson ImmunoResearch, cat no. 109-605-098). Cells ($2.5 \times 10^5$ cells/ml) were mixed with goat anti-human AffiniPure Goat Anti-Human IgG Fc gamma-Alexa Fluor® 647 (0.2 µg/ml; Jackson ImmunoResearch Laboratories, 109-605-098) or AffiniPure Goat Anti-Rat IgG (H+L) Alexa Fluor® 647 (0.2 µg/ml; Jackson ImmunoResearch, 112-605-143) depending on the backbone of the antibody. Serial dilutions of test and control antibodies (range 0.003 to 3 µg/mL in 2-fold dilution steps) were prepared and 2 µl antibody dilution was added to 5 µl of the cell/conjugate mixture in 1536 well plates (Greiner, cat. no. 789866). Plates were incubated at room temperature for 9 hours, and after which fluorescence intensity was determined using an ImageXpress Velos Laser Scanning Cytometer (Molecular Devices, LLC, Sunnyvale, Calif., USA) and total fluorescence was used as read-out. Samples were stated positive when counts were higher than 50 and counts×fluorescence was at least three higher than the negative control.

Results from B7H4 Antibody Panel Generation

From 176 out of 193 hybridomas produced, heavy and light chain variable region sequences were successfully obtained. Of 351 heavy chain/light chain combinations tested, 98 showed binding in antigen screenings assays using human B7H4-transfected HEK-293F cells as described above. 35 antibodies were selected: 26 with original sequences and 9 variants with point mutations introduced in the variable domains. Antibodies were produced as monovalent binding antibodies (as CD3 bispecifics) and bivalent binding antibodies (as IgG1 molecules), and tested for binding to tumor cells as described below. Of the antibodies from the panel generated, only antibody B7H4-C1 and its variant B7H4-C1-N52S, of which the corresponding VH and VL antibody variable domain encoding sequences are listed in TABLE 1, provided for antibodies that bound to tumor cells as described below.

Further B7H4 Antibodies

In the examples, further antibodies specific for B7H4 were used containing the variable domains previously described in WO2014159835 (referenced therein as SEQ ID NOs 38 and 35), corresponding herein to B7H4-C2, relevant sequences of the variable domains are listed herein in TABLE 1 and include SEQ ID NO. 43 and 47; WO2014159835 (referenced therein as SEQ ID NO 56 and 55), corresponding herein to B7H4-C3, relevant sequences of the variable domains are listed herein in TABLE 1 and include SEQ ID NO. 36 and 40; WO2009073533 (referenced therein as SEQ ID No 2 and 7), corresponding herein to B7H4-C4 and relevant sequences of the variable domains are listed herein in TABLE 1 and include SEQ ID NO. 50 and 54; and US20190085080A1 corresponding herein to B7H4-C5 and relevant sequences of the variable domains are listed herein in TABLE 1 and include SEQ ID NO. 65 and 69. The corresponding VH and VL antibody variable domain encoding sequences were synthesized and cloned into pcDNA3.3 based vectors with codon optimized human IgG1m(f) and Kappa or Lambda constant domains, or variants thereof, to produce monospecific and bispecific antibodies. When reference is made to antibody IgG1-B7H4-CX-FEAL, this represents an antibody having the B7H4-CX variable regions, being of the IgG1 isotype, and having amino acid substitutions L234F, L235E, D265A and F409R in the constant region of the heavy chain.

IgG1-b12 Antibody

The antibody b12, an HIV-1 gp120 specific antibody (Barbas, CF. J Mol Biol. 1993 Apr. 5; 230(3):812-23) was used in some examples as a negative control IgG1, or as the non-binding control Fab-arm of a control bispecific. The codon optimized antibody encoding sequences for this control antibody were synthesized and cloned into pcDNA3.3 based vectors with codon optimized human IgG1m(f) and Kappa constant domains, or variants thereof. The sequence of the variable heavy chain (VH) region and the sequence of the variable light chain (VL) region are included herein as SEQ ID NOs.: 14 and 15, respectively.

Example 2—Humanized CD3 Antibodies for the Generation of CD3xB7H4 Bispecific Antibodies The generation of humanized antibody IgG1-huCD3-H1L1 (of which the variable heavy and light chain region sequences are listed herein in SEQ ID NO: 16 and 22) is described in Example 1 of WO2015/001085. IgG1-huCD3-H1L1 is referred to herein as 'IgG1-huCD3'. Antibody IgG1-huCD3-H1L1-FEAL is a variant hereof with three amino acid substitutions in the Fc domain (L234F, L235E, D265A), in addition to an amino acid substitution that allows the generation of bispecific antibodies through controlled Fab-arm exchange (F405L), as described herein below. It has been shown that such mutations did not have effect on target binding of the antibodies in which they are introduced (see e.g. US 2015/0337049 and Engelberts et al., 2020, EBioMedicine 52: 102625).

The generation of humanized antibody IgG1-huCD3-H1L1-H101G (of which the variable heavy chain and light chain region sequences are listed as SEQ ID NO: 17 and 22 herein) is described in Example 2 of WO2017/009442. IgG1-huCD3-H1L1-H101G will be referred to as 'IgG1-huCD3-H101G'. This variant comprises a substitution H101G in the variable heavy chain region sequence (compare SEQ ID NO.16 and 17), and has the same light chain as IgG1-huCD3-H1L1. Antibody IgG1-huCD3-H101G-FEAL is a variant hereof with amino acid substitutions L234F, L235E, D265A and F405L.

Example 3—B7H4 Binding Affinity Determination Using Biolayer Interferometry

Target binding affinity of B7H4 antibodies was determined by label-free biolayer interferometry (BLI) on an Octet HTX instrument (FortéBio). Experiments were carried out while shaking at 1,000 RPM at 30° C. Initially, the affinity of IgG1-B7H4-C1-N52S-FEAR, IgG1-B7H4-C2-FEAR, IgG1-B7H4-C3-FEAR, and IgG1-B7H4-C4-FEAR for human and mouse B7H4 was determined using BLI. Anti-Human IgG Fc Capture (AHC) biosensors (FortéBio, cat. no. 18-5060) were pre-conditioned by exposure to 10 mM glycine (Sigma-Aldrich, cat. no. 15527) buffer pH 1.7 for 5 s, followed by neutralization in Sample Diluent (FortéBio, cat. no. 18-1048) for 5 s; both steps were repeated 2 times. Next, AHC sensors were loaded with antibody (1 µg/mL in Sample diluent) for 600 s. After a baseline measurement in Sample Diluent (100 s), the association (300 s) and dissociation (1,000 s) of human B7H4 (Sino Biological, cat. no. 10738-H08H-100) or mouse B7H4 (R&D Systems, cat. no. 2154-B7-050) was determined using a concentration range of 1.56–100 nM (0.04-2.68 µg/mL) and 5.9-375 nM (0.16-10 µg/mL) for human and mouse B7H4 respectively, with two-fold dilution steps in Sample Diluent. The theoretical molecular mass of human B7H4 and mouse B7H4 (as ECD-His tagged molecules) based on their amino acid sequences (26.8 kDa and 26.6 kDa respectively) were used for calculations. For each antibody a reference sensor was used, which was incubated with Sample Diluent instead of antigen. AHC sensors were regenerated by exposure to 10 mM glycine buffer pH 1.7 for 5 s, followed by neutralization in Sample Diluent for 5 s; both steps were repeated twice. Subsequently sensors were loaded again with antibody for the next cycle of kinetics measurements.

Data were acquired using Data Acquisition Software v9.0.0.49d (FortéBio) and analyzed with Data Analysis Software v9.0.0.12 (FortéBio). Data traces were corrected per antibody by subtraction of the reference sensor. The Y-axis was aligned to the last 10 s of the baseline, Interstep Correction alignment to dissociation and Savitzky-Golay filtering were applied. Data traces with a response <0.05 nm were excluded from analysis. The data was fitted with the 1:1 Global Full fit model using a window of interest for the association and dissociation times set at 300 s and 200 s respectively.

In a second experiment, the affinity of IgG1-B7H4-C1-N52S-FEAR, IgG1-B7H4-C2-FEAR, IgG1-B7H4-C3-FEAR, IgG1-B7H4-C4-FEAR, and IgG1-B7H4-C5-FEAR for human and mouse B7H4 was determined using BLI. The experiment was performed as described above, with some small exceptions. The preconditioning steps were repeated 5 times. The association (200 s) and dissociation (1,000 s) of human or mouse B7H4 were determined using a concentration range of 0.78-800 nM with two-fold dilution steps in Sample Diluent. Data were acquired using Data Acquisition Software v12.0.1.8 (FortéBio) and analyzed with Data Analysis Software v12.0.1.2 (FortéBio). The data was fitted with the 1:1 Global Full Fit model using a window of interest for the association time of 200 s and a window of interest for the dissociation time of 200 s, except for IgG1-B7H4-C2-FEAR for which a 1,000 s dissociation time was used. The dissociation time was chosen based upon $R^2$ value, visual inspection of the curve and at least 5% signal decay during the dissociation step. Data traces generated with antigen concentrations higher than 100 nM were excluded from analysis for antibodies with an affinity below 50 nM.

In addition, the affinity of for cynomolgus monkey B7H4 was determined by BLI. In a first experiment, the affinity of bsIgG1-huCD3-FEALxB7H4-C1-FEAR, bsIgG1-huCD3-FEALxB7H4-C1-N52S-FEAR, bsIgG1-huCD3-FEALxB7H4-C2-FEAR, bsIgG1-huCD3-FEALxB7H4-C3-FEAR, and bsIgG1-huCD3-H101G-FEALxB7H4-C4-FEAR for cynomolgus monkey B7H4 was determined. Amine Reactive $2^{nd}$ Generation (AR2G) biosensors (FortéBio, cat. no. 18-5092) were activated by reaction with 20 mM EDC (N-(3-Dimethylaminopropyl)-N'-ethylcarbodiimide hydrochloride) (FortéBio, cat. no. 18-1033) and 10 mM s-NHS (N-hydroxysulfosuccinimide sodium salt) (FortéBio, cat. no. 18-1067) for 300 s. The activated sensors were loaded with 10 µg/mL recombinant hIgG1 Fc-tagged cynomolgus monkey B7H4 (Creative BioMart, cat. no. VTCN1-1517R) in 10 mM Sodium Acetate pH 4.0 (FortéBio, cat. no. 18-1068) for 600 s and quenched with 1 M ethanolamine pH 8.5 (FortéBio, cat. no. 18-1071) for 300 s. After a baseline measurement in Sample Diluent (300 s; FortéBio, cat. no. 18-1048), the association (100 s) and dissociation (1,000 s) of functionally monovalent B7H4 binding by CD3xB7H4 bispecific antibodies (as indicated in Table 8) was determined using a concentration range of 0.23-15 µg/mL (1.56-100 nM) with two-fold dilution steps in Sample Diluent. A molecular mass of 150 kDa of the antibodies was used for calculations. For each antibody a reference sensor was used, which was incubated with Sample Diluent instead of antibody.

Data were acquired using Data Acquisition Software v9.0.0.49d (FortéBio) and analyzed with Data Analysis Software v9.0.0.12 (FortéBio). Data traces were corrected per antibody by subtraction of the reference sensor. The Y-axis was aligned to the last 10 s of the baseline, Interstep Correction alignment to dissociation and Savitzky-Golay filtering were applied. Data traces with a response <0.05 nm were excluded from analysis. The data was fitted with the 1:1 Global Full fit model using a window of interest for the association and dissociation times set at 100 s and 200 s respectively.

In a second experiment to determine the affinity of the B7H4 antibodies for cynomolgus monkey B7H4, the affinity of bsIgG1-huCD3-H101G-FEALxB7H4-C1-N52S-FEAR and bsIgG1-huCD3-H101G-FEALxB7H4-C5-FEAR was determined. The experiment was performed as described above, with some small exceptions. After a baseline measurement in Sample Diluent of 600 s, the association (200 s) and dissociation (1,000 s) of functionally monovalent B7H4 binding by CD3xB7H4 bispecific antibodies (as indicated in Table 9) was determined using a concentration range of approximately 0.1-116 µg/mL (0.78-800 nM) with two-fold dilution steps in Sample Diluent. The specific molecular mass of each antibody (approximately 145 kDa) was used for calculations. Data were acquired using Data Acquisition Software v12 (FortéBio) and analyzed with Data Analysis Software v12 (FortéBio). Data traces with a response <0.03 nm were excluded from analysis. The data was fitted with the 1:1 Global Full fit model using a window of interest for the association time and dissociation time of 200 s. The dissociation time was chosen based upon $R^2$ value, visual inspection of the curve and at least 5% signal decay during the dissociation step. Data traces generated with antibody concentrations higher than 200 nM were excluded from analysis for antibodies with an affinity below 50 nM. All results were determined with an $R^2$ of at least 0.98.

"$K_D$" (M) refers to the equilibrium dissociation constant of the antibody-antigen interaction, and is obtained by dividing $k_d$ by $k_a$. "$k_d$" (sec$^{-1}$) refers to the dissociation rate constant of the antibody-antigen interaction. This is sometimes also referred to as the $k_{off}$ value or off-rate. "$k_a$" (M$^{-1}$×sec$^{-1}$) refers to the association rate constant of the antibody-antigen interaction. This is sometimes also referred to as the $k_{on}$ value or on-rate.

Tables 4 and 5 show the results of the first and the second experiment in which the association rate constant $k_a$ (1/Ms), dissociation rate constant $k_d$ (1/s) and equilibrium dissociation constant $K_D$ (M) of the indicated antibodies for human B7H4 were determined by biolayer interferometry.

TABLE 4

Binding affinities of antibodies to human B7H4 extracellular domain as determined by label-free biolayer interferometry. ND = not determined.

| Antibody | On-rate $k_a$ (1/Ms) | Off-rate $k_d$ (1/s) | $K_D$ (M) |
|---|---|---|---|
| IgG1-B7H4-C1-FEAR | ND | ND | ND |
| IgG1-B7H4-C1-N52S-FEAR | 9.4E+04 | 5.4E−03 | 5.7E−08 |
| IgG1-B7H4-C2-FEAR | 5.2E+04 | 8.8E−04 | 1.7E−08 |
| IgG1-137H4-C3-FEAR | 9.9E+04 | 4.1E−03 | 4.2E−08 |
| IgG1-137H4-C4-FEAR | 1.5E+05 | 1.6E−03 | 1.1E−08 |

TABLE 5

Binding affinities of antibodies to human B7H4 extracellular domain as determined by label-free biolayer interferometry.

| Antibody | On-rate $k_a$ (1/Ms) | Off-rate $k_d$ (1/s) | $K_D$ (M) |
|---|---|---|---|
| IgG1-B7H4-C1-N52S-FEAR[1] | 8.4E+04 | 4.7E-03 | 5.7E-08 |
| IgG1-B7H4-C2-FEAR | 5.9E+04 | 1.7E-04 | 3.0E-09 |
| IgG1-B7H4-C3-FEAR | 8.1E+04 | 4.4E-03 | 5.4E-08 |
| IgG1-B7H4-C4-FEAR | 2.2E+05 | 1.7E-03 | 7.9E-09 |
| IgG1-B7H4-C5-FEAR | 2.5E+05 | 2.5E-03 | 9.9E-09 |

[1]Shown are the averaged results of n = 3 experiments.

Tables 6 and 7 show the results of two experiments in which the $k_a$ (1/Ms), $k_d$ (1/s), and $K_D$ (M) of the indicated antibodies for mouse B7H4 were determined by biolayer interferometry.

TABLE 6

Binding affinities of antibodies to mouse B7H4 extracellular domain as determined by label-free biolayer interferometry. ND = not determined; - = no binding (response <0.05 nm at the highest concentration used).

| Antibody | On-rate $k_a$ (1/Ms) | Off-rate $k_d$ (1/s) | $K_D$ (M) |
|---|---|---|---|
| IgG1-B7H4-C1-FEAR | ND | ND | ND |
| IgG1-B7H4-C1-N52S-FEAR | — | — | — |
| IgG1-B7H4-C2-FEAR | 3.3E+04 | 7.7E-04 | 2.4E-08 |
| IgG1-B7H4-C3-FEAR | 5.1E+04 | 2.0E-02 | 3.9E-07 |
| IgG1-B7H4-C4-FEAR | 8.4E+04 | 1.4E-03 | 1.6E-08 |

TABLE 7

Binding affinities of antibodies to mouse B7H4 extracellular domain as determined by label-free biolayer interferometry. - = no binding (response <0.05 nm at the highest concentration used).

| Antibody | On-rate $k_a$ (1/Ms) | Off-rate $k_d$ (1/s) | $K_D$ (M) |
|---|---|---|---|
| IgG1-B7H4-C1-N52S-FEAR | — | — | — |
| IgG1-B7H4-C2-FEAR | 6.3E+04 | 1.3E-04 | 2.1E-09 |
| IgG1-B7H4-C3-FEAR | 5.9E+04 | 1.8E-02 | 3.0E-07 |
| IgG1-B7H4-C4-FEAR | 1.4E+05 | 1.4E-03 | 9.7E-09 |
| IgG1-B7H4-05-FEAR | 1.7E+05 | 2.4E-03 | 1.4E-08 |

Tables 8 and 9 show the results of two experiments in which the $k_a$ (1/Ms), $k_d$ (1/s), and $K_D$ (M) of the indicated antibodies for cynomolgus monkey B7H4 were determined by biolayer interferometry.

TABLE 8

Binding affinities of functionally monovalent antibodies to cynomolgus monkey B7H4 extracellular domain as determined by label-free biolayer interferometry.

| Antibody | On-rate $k_a$ (1/Ms) | Off-rate $k_d$ (1/s) | $K_D$ (M) |
|---|---|---|---|
| bsIgG1-huCD3-FEALxB7H4-C1-FEAR | 2.7E+05 | 1.4E-03 | 5.1E-09 |
| bsIgG1-huCD3-FEALxB7H4-C1-N52S-FEAR | 1.4E+05 | 3.0E-03 | 2.1E-08 |
| bsIgG1-huCD3-FEALxB7H4-C2-FEAR | 1.3E+05 | 4.1E-04 | 3.1E-09 |
| bsIgG1-huCD3-FEALxB7H4-C3-FEAR | 2.8E+05 | 4.1E-03 | 1.5E-08 |
| bsIgG1-huCD3-H101G-FEALxB7H4-C4-FEAR | 3.5E+05 | 1.5E-03 | 4.2E-09 |

TABLE 9

Binding affinities of functionally monovalent antibodies to cynomolgus monkey B7H4 extracellular domain as determined by label-free biolayer interferometry.

| Antibody | $R^2$ | On-rate $k_a$ (1/Ms) | Off-rate $k_d$ (1/s) | $K_D$ (M) |
|---|---|---|---|---|
| bsIgG1-huCD3-H101G-FEALxB7H4-C1-N52S-FEAR[a] | 0.99 | 1.2E+05 | 2.7E-03 | 2.5E-08 |
| bsIgG1-huCD3-H101G-FEALxB7H4-05-FEAR[b] | 0.97 | 4.2E+05 | 2.5E-03 | 6.0E-09 |

[a]Shown are the averaged results of n = 3 experiments.
[b]Did not meet a stringent quality control $R^2$ threshold of 0.98.

Example 4—CD3 Binding Affinity Determination Using Biolayer Interferometry

Binding affinities of IgG1-huCD3-FEAL and IgG1-huCD3-H101G-FEAL were determined as described in Example 7 of WO2017/009442.

In short, binding affinities of selected CD3 antibodies in an IgG1-huCD3-FEAL format for recombinant soluble CD3ε (CD3E27-GSKa) (mature protein of SEQ ID NO: 13) were determined using biolayer interferometry on a ForteBio Octet HTX (ForteBio). Anti-human Fc capture biosensors (ForteBio, cat. no. 18-5060) were loaded for 600 s with hIgG (1 μg/mL). After a baseline measurement (200 s), the association (1000 s) and dissociation (2000 s) of CD3E27-GSKa was determined, using a CD3E27-GSKa concentration range of 27.11 μg/mL-0.04 μg/mL (1000 nM-1.4 nM) with three-fold dilution steps (sample diluent, ForteBio, cat. no. 18-5028). For calculations, the theoretical molecular mass of CD3E27-GSKa based on the amino acid sequence was used, i.e. 27.11 kDa. Experiments were carried out while shaking at 1000 rpm and at 30° C. Each antibody was tested in at least two independent experiments. Data was analyzed with ForteBio Data Analysis Software v8.1, using the 1:1 model and a global full fit with 1000 s association time and 100 s dissociation time. Data traces were corrected by subtraction of a reference curve (antibody on biosensor, measurement with sample diluent only), the Y-axis was aligned to the last 10 s of the baseline, and interstep correction as well as Savitzky-Golay filtering was applied. Data traces with a response <0.05 nm were excluded from analysis.

Table 10 shows the association rate constant $k_a$ (1/Ms), dissociation rate constant $k_d$ (1/s) and equilibrium dissociation constant $K_D$ (M) for recombinant CD3ε determined by biolayer interferometry. IgG1-huCD3-FEAL showed a relatively high ($K_D$: 15 nM) binding affinity to recombinant CD3ε compared to IgG1-huCD3-H101G-FEAL ($K_D$: 683 nM).

TABLE 10

Binding affinities of monospecific, bivalent CD3 antibodies to recombinant CD3ε as determined by label-free biolayer interferometry

| Antibody | On-rate $k_a$ (1/Ms) | Off-rate $k_d$ (1/s) | $K_D$ (nM) |
|---|---|---|---|
| IgG1-huCD3-FEAL | 2.7E+05 | 4.0E-03 | 15 |
| IgG1-huCD3-H101G-FEAL | 3.0E+04 | 2.0E-02 | 683 |

Example 5—Cross-Block of B7H4 Antibodies Determined by Biolayer Interferometry

Antibody cross-block analysis (epitope binning) in classical Sandwich format was performed by BLI on an Octet HTX instrument (FortéBio). A first cross-block experiment with IgG1-B7H4-C1-N52S-FEAR, IgG1-B7H4-C2-FEAR, IgG1-B7H4-C3-FEAR, and IgG1-B7H4-C4-FEAR was carried out while shaking at 1,000 RPM and at 30° C.

Amine Reactive $2^{nd}$ Generation (AR2G) biosensors (FortéBio, cat. no. 18-5092) were activated for 300 s with a solution of 20 mM EDC (N-(3-Dimethylaminopropyl)-N'-ethylcarbodiimide hydrochloride) (Sigma-Aldrich, cat. no. 03449) and 10 mM s-NHS (N-Hydroxysulfosuccinimide sodium salt) (Sigma-Aldrich, cat. no. 56485). The activated AR2G sensors were loaded with 20 μg/mL first antibody in 10 mM Sodium Acetate pH 6.0 (FortéBio, cat. no. 18-1070) for 600 s and quenched with 1 M ethanolamine pH 8.5 (FortéBio cat. no. 18-1071) for 300 s. After a baseline measurement in Sample Diluent (50 s; FortéBio, cat. no. 18-1048), the AR2G biosensors containing immobilized antibodies were loaded for 300 s with human B7H4 (100 nM or 2.68 μg/mL diluted in Sample Diluent; Sino Biological, cat. no 10738-H08H). The theoretical molecular mass of human B7H4 based on the amino acid sequence (26.8 kDa) was used for calculations. The association (300 s) of a second antibody (10 μg/mL in Sample Diluent) was determined. Sensors were regenerated by exposure to 10 mM glycine (Riedel-de Haën, cat. no. 15527) buffer pH 2.5 for 5 s, followed by neutralization in Sample Diluent for 5 s; both steps were repeated twice. Subsequently the sensors containing immobilized first antibody were used again, starting with the baseline step.

Data were acquired using Data Acquisition Software v9.0.0.49d (FortéBio) and analyzed with Data Analysis HT Software v10.0.17 (FortéBio). Data traces were corrected by subtraction of a reference curve (Sample Diluent instead of second antibody) in order to correct for the dissociation of B7H4 from the immobilized first antibody. The Y-axis was aligned to the start of the association step and Savitzky-Golay filtering was applied. The corrected association responses of the second antibodies were plotted in a matrix format. In general, responses >0.05 nm were considered non-cross-blocking antibodies, while responses <0.05 nm were considered to be blocking antibody pairs.

The cross-block experiment was repeated to also include IgG1-B7H4-C5-FEAR and was performed as described above, with minor adaptations. The experiment was carried out while shaking at 1,000 RPM and at 22° C. Data were acquired using Data Acquisition Software v12.0.1.8 (FortéBio) and analyzed with Data Analysis HT Software v12.0.1.55 (FortéBio). In general, responses >0.1 nm were considered non-cross-blocking antibodies, while responses <0.1 nm were considered to be blocking antibody pairs.

Initial cross-block experiments were performed for antibodies IgG1-B7H4-C1-N52S-FEAR, IgG1-B7H4-C3-FEAR, IgG1-B7H4-C4-FEAR and IgG1-B7H4-C2-FEAR. The results are summarized in Table 11. A second set of cross-block experiments was performed to also include IgG1-B7H4-C5-FEAR. These results are summarized in Table 12. The first column shows the immobilized antibodies; the first row shows the antibodies in solution (referred to as 'the second antibodies' above). Corrected association responses of the antibodies in solution are shown. Cross-block of antibodies is indicated by bold font, and non-blocking antibody combinations are unmarked (transparent background), showing that IgG1-B7H4-C1-N52S-FEAR, IgG1-B7H4-C3-FEAR, and IgG1-B7H4-C5-FEAR are cross-blocking with each other and not with IgG1-B7H4-C4-FEAR and IgG1-B7H4-C2-FEAR, and vice versa.

TABLE 11

First antibody cross-block experiment using biolayer interferometry. The first column shows the immobilized antibodies and the first row shows the antibodies in solution. Corrected association responses of the antibodies in solution are shown. Cross-block of antibodies is indicated by bold font, non-blocking antibody combinations are unmarked (transparent background).

| Antibody cross-block | IgG1-B7H4-C1-N52S-FEAR | IgG1-B7H4-C3-FEAR | IgG1-B7H4-C4-FEAR | IgG1-B7H4-C2-FEAR |
|---|---|---|---|---|
| IgG1-137H4-C1-N52S-FEAR | −0.01 | 0.00 | 0.80 | 0.56 |
| IgG1-137H4-C3-FEAR | −0.02 | −0.01 | 0.97 | 0.53 |
| IgG1-137H4-C4-FEAR | 0.82 | 0.56 | −0.02 | −0.01 |
| IgG1-137H4-C2-FEAR | 0.74 | 0.54 | 0.00 | 0.00 |

TABLE 12

Second antibody cross-block experiment using biolayer interferometry. The first column shows the immobilized antibodies and the first row shows the antibodies in solution. Corrected association responses of the antibodies in solution are shown. Cross-block of antibodies is indicated by bold font, non-blocking antibody combinations are unmarked (transparent background).

| Antibody cross-block | IgG1-B7H4-C1-N52S-FEAR | IgG1-B7H4-C3-FEAR | IgG1-B7H4-C2-FEAR | IgG1-B7H4-C4-FEAR | IgG1-B7H4-C5-FEAR |
|---|---|---|---|---|---|
| IgG1-137H4-C1-N52S-FEAR | 0 | 0.01 | 0.38 | 0.42 | 0.43 |
| IgG1-137H4-C3-FEAR | 0.01 | 0 | 0.44 | 0.57 | 0.61 |
| IgG1-137H4-C2-FEAR | 0.28 | 0.25 | 0.01 | 0.01 | 0.02 |
| IgG1-137H4-C4-FEAR | 0.5 | 0.39 | 0 | −0.01 | 0 |
| IgG1-137H4-05-FEAR | 0.67 | 0.57 | −0.03 | −0.03 | −0.01 |

Example 6—Generation of Bispecific Antibodies by 2-MEA-Induced Fab-Arm Exchange

Bispecific antibodies were generated in vitro using the DuoBody® platform technology, i.e. 2-MEA-induced Fab-arm exchange as described in WO2011147986, WO2011131746 and WO2013060867 (Genmab) and Labrijn et al. (Labrijn et al., PNAS 2013, 110: 5145-50; Gramer et al., MAbs 2013, 5: 962-973). To enable the production of bispecific antibodies by this method, IgG1 molecules carrying specific point mutations in the CH3 domain were generated: in one parental IgG1 antibody the F405L mutation (i.e. the CD3 antibodies in this application), in the other parental IgG1 antibody the K409R mutation (i.e. the B7H4 or control, HIV-1 gp120-specific, antibodies in this application). In addition to these mutations, the parental IgG1 antibodies included substitutions L234F, L235E, D265A (FEA).

To generate bispecific antibodies, the two parental antibodies were mixed in equal mass amounts in PBS buffer (Phosphate Buffered Saline; 8.7 mM $HPO_4^{2-}$, 1.8 mM $H_2PO_4^-$, 163.9 mM $Na^+$, 140.3 mM $Cl^-$, pH 7.4). 2-mercaptoethylamine-HCl (2-MEA) was added to a final concentration of 75 mM and the reaction mixture was incubated at 31° C. for 5 h. The 2-MEA was removed by dialysis into PBS buffer using 10 kDa molecular-weight cutoff Slide-A-Lyzer carriages (Thermo Fisher Scientific) according to the manufacturer's protocol in order to allow re-oxidation of the inter-chain disulfide bonds and formation of intact bispecific antibodies.

The following antibodies were used in the examples:
B7H4 Antibodies
IgG1-B7H4-C1-FEAR (having the VH and VL sequences set forth in SEQ ID NO: 25 and SEQ ID NO: 33).
IgG1-B7H4-C1-N52S-FEAR (having the VH and VL sequences set forth in SEQ ID NO: 29 and SEQ ID NO: 33).
IgG1-B7H4-C2-FEAR having the VH and VL sequences set forth in SEQ ID NO: 43 and SEQ ID NO: 47).
IgG1-B7H4-C3-FEAR having the VH and VL sequences set forth in SEQ ID NO: 36 and SEQ ID NO: 40).
IgG1-B7H4-C4-FEAR having the VH and VL sequences set forth in SEQ ID NO: 50 and SEQ ID NO: 54).
IgG1-B7H4-C5-FEAR having the VH and VL sequences set forth in SEQ ID NO: 65 and SEQ ID NO: 69).

The annotation IgG1 indicates that full length antibodies of the IgG1 isotype were made, and the FEAR annotation indicates that the heavy chain constant regions contains amino acid substitutions L234F, L235E, D265A and K409R and the light chain constant regions were of the kappa type (SEQ ID NO. 61 and 63, respectively).

CD3 Antibodies
IgG1-huCD3-FEAL (having the VH and VL sequences set forth in SEQ ID NO: 16 and SEQ ID NO: 22).
IgG1-huCD3-H101G-FEAL (having the VH and VL sequences set forth in SEQ ID NO: 17 and SEQ ID NO: 22).

The annotation IgG1 indicates that full length antibodies of the IgG1 isotype were made, and the FEAL annotation indicates that the heavy chain constant regions contains amino acid substitutions L234F, L235E, D265A and F405L and the light chain constant regions were of the lambda type (SEQ ID NO. 60 and 64, respectively).

Control Antibodies
IgG1-b12-K409R (having the VH and VL sequences set forth in SEQ ID NO: 14 and SEQ ID NO: 15).

The annotation IgG1 indicates that full length antibodies of the IgG1 isotype were made, and the K409R annotation indicates that the heavy chain constant regions contains amino acid substitution K409R and the light chain constant regions were of the kappa type (SEQ ID NO. 62 and 63, respectively). Bispecific antibodies The CD3 and B7H4 antibodies described above were combined to generate a bispecific antibody, having one antigen-binding region capable of binding human CD3 and the other antigen-binding region capable of binding B7H4, providing a bispecific antibody of the isotype IgG1, which is annotated as bsIgG1.

bsIgG1-huCD3-FEALxB7H4-C1-FEAR
bsIgG1-huCD3-FEALxB7H4-C1-N52S-FEAR
bsIgG1-huCD3-H101G-FEALxB7H4-C1-N52S-FEAR
bsIgG1-huCD3-FEALxB7H4-C2-FEAR
bsIgG1-huCD3-FEALxB7H4-C3-FEAR
bsIgG1-huCD3-FEALxB7H4-C4-FEAR
bsIgG1-huCD3-H101G-FEALxB7H4-C2-FEAR
bsIgG1-huCD3-H101G-FEALxB7H4-C3-FEAR
bsIgG1-huCD3-H101G-FEALxB7H4-C4-FEAR
bsIgG1-huCD3-H101G-FEALxB7H4-C5-FEAR
bsIgG1-huCD3-FEALxb12-FEAR (for the b12 arm having the VH and VL sequences set forth in SEQ ID NO: 14 and SEQ ID NO: 15)
bsIgG1-huCD3-H101G-FEALxb12-FEAR Example 7—Determining the B7H4 Domain and Functional Epitope Involved in Binding Using B7H4-B7H3 Chimeric Molecules and a B7H4 Alanine Scanning Library Domain Mapping Using B7H4-B7H3 Chimeric Molecules Using End-Point Analysis The B7H4 domain specificity of the B7H4 antibodies was determined using a panel of cells transfected to express human B7H4, human B7H3 (a structurally comparable protein with sufficient amino acid sequence difference in the extracellular domain) or two different human B7H4-B7H3 chimeric molecules. Expression constructs were prepared encoding human B7H4, human B7H3 (Uniprot accession no. Q5ZPR3-1; SEQ ID NO: 9), or a chimeric molecule containing the IgV domain of B7H3 and the IgC domain of B7H4 (B7H3-IgV/B7H4-IgC; SEQ ID NO: 11), or a chimeric molecule containing the IgV domain of B7H4 and the IgC domain of B7H3 (B7H4-IgV/B7H3-IgC; SEQ ID NO: 10). HEK cells were transiently transfected to express these constructs.

Cells ($3 \times 10^4$ cell/well) were incubated in polystyrene 96-well round-bottom plates (Greiner bio-one, cat. no. 650101) with serial dilutions of antibodies (range 0.0046 to 10 µg/mL in 3-fold dilution steps) in 50 µL PBS/0.1% BSA/0.02% azide (FACS buffer) at 4° C. for 30 min. After washing twice in FACS buffer, cells were incubated with secondary antibody at 4° C. for 30 min. As a secondary antibody, R-Phycoerythrin (PE)-conjugated goat-anti-human IgG F(ab')$_2$ (1:500 in staining buffer; Jackson ImmunoResearch Laboratories, Inc., West Grove, Pa., cat. no. 109-116-098) was used. Next, cells were washed twice in FACS buffer, re-suspended in 20 µL FACS buffer and analyzed on an iQue Screener (Intellicyt Corporation, USA). The binding of bsIgG1-huCD3-FEALxB7H4-C1-N52S-FEAR, bsIgG1-huCD3-FEALxB7H4-C4-FEAR, bsIgG1-huCD3-FEALxB7H4-C3-FEAR and bsIgG1-huCD3-FEALxB7H4-C2-FEAR at 10 µg/mL was determined as % mean fluorescence intensity (MFI) of the binding 10 µg/mL of:

IgG1-B7H3-BRCA84D (a B7H3-specific IgG1 antibody, generated as described above with CDR sequences as described for antibody BRCA84D in WO2011109400) to B7H3 expressing cells,
bsIgG1-huCD3-FEALxB7H4-C4-FEAR to B7H3-IgV/B7H4-IgC expressing cells,
bsIgG1-huCD3-FEALxB7H4-C2-FEAR to B7H4-IgV/B7H3-IgC expressing cells,
and bsIgG1-huCD3-FEALxB7H4-C3-FEAR to B7H4 expressing cells.

FIG. 1 shows that the IgC domain of B7H4 is involved in binding of bsIgG1-huCD3-FEALxB7H4-C1-N52S-FEAR and bsIgG1-huCD3-FEALxB7H4-C4-FEAR, both the IgC and IgV domain of B7H4 are involved in binding of bsIgG1-huCD3-FEALxB7H4-C3-FEAR, and at least the IgV domain of B7H4 is involved in binding of bsIgG1-huCD3-FEALxB7H4-C2-FEAR. For the C2 antibody from which the variable domains were used to created bsIgG1-huCD3-FEALxB7H4-C2-FEAR, it has been described that it binds to the IgV domain; the data in FIG. 1 indicates that the IgC domain is also involved in binding (WO2014159835 and Leong et al 2015, Mol. Pharmaceutics 12, 1717-1729).

Domain Mapping Using B7H4-B7H3 Chimeric Molecules Using Analysis of Full Dose-Response Curves Further experiments were conducted to study the B7H4 domain specificity of the B7H4 antibodies in more detail, by analysis of full dose-response curves. In these experiments, the domain specificity of bsIgG1-huCD3-H101G-FEALxB7H4-C5-FEAR was also determined. Binding of serial dilutions (0.014 to 30 µg/mL in 3-fold dilution steps) of bsIgG1-huCD3-H101G-FEALxB7H4-C1-N52S-FEAR, bsIgG1-huCD3-H101G-FEALxB7H4-C2-FEAR, bsIgG1-huCD-H101G-FEALxB7H4-C3-FEAR, bsIgG1-huCD3-H101G-FEALxB7H4-C4-FEAR and bsIgG1-huCD3-H101G-FEALxB7H4-C5-FEAR to HEK cells transiently transfected to express human B7H4 or the B7H4-B7H3 chimeric molecules B7H3-IgV/B7H4-IgC or B7H4-IgV/B7H3-IgC was determined as described above. FIG. 2 shows the dose-response curves, showing that the IgC domain of B7H4 is involved in binding of bsIgG1-huCD3-H101G-FEALxB7H4-C1-N52S-FEAR, in line with the findings of the alanine scanning library experiments. Furthermore, the IgV domain is involved in the binding of bsIgG1-huCD3-H101G-FEALxB7H4-C2-FEAR, bsIgG1-huCD3-H101G-FEALxB7H4-C4-FEAR and bsIgG1-huCD3-H101G-FEALxB7H4-C5-FEAR, whereas both the IgC and IgV domain appear involved in the binding of bsIgG1-huCD3-H101GFEALxB7H4-C3-FEAR.

Determination of the Contribution of B7H4 Amino Acid Residues to Binding of B7H4 Antibodies Using a B7H4 Alanine Scanning Library Library Design A human B7H4 (Uniprot Q7Z7D3-1) single residue alanine library was synthesized (GeneArt) in which all amino acid residues in the extracellular domain of human B7H4 were individually mutated to alanines except for positions containing alanines or cysteines. Cysteines were not mutated to minimize the chance of structural disruption of the antigen. The library was cloned in the pMAC expression vector containing a CMV/TK-polyA expression cassette, an Amp resistance gene and a pBR322 replication origin.

Library Production and Screening

The antibodies C1-N52S, C2 and C3 were generated as recombinant monovalent antibodies as described in WO2007059782 with a mNeonGreen tag. The wild type B7H4 and alanine mutants were expressed individually in FreeStyle HEK293 cells according to the manufacturer's instructions (Thermo Scientific). One day post transfection the cells were harvested. Approximately 50,000 cells were incubated with 20 µL mNeoGreen labeled antibody of interest. Cells were incubated for 1 hour at room temperature. Subsequently, 150 µL FACS buffer was added and cells were washed twice with FACS buffer. Cells were resuspended in 30 µL fresh FACS buffer and analyzed by flow cytometry using an iQue Screener (Intellicyt Corporation, USA).

The entire experiment was performed 2 times in duplicate.

Data Analysis

For every sample, the average antibody binding per cell was determined as the geometric mean of the fluorescence intensity (gMFI) for the ungated cell population. The gMFI is influenced by the affinity of the antibody for the B7H4 mutant and the expression level of the B7H4 mutant per cell. Since specific alanine mutations can impact the surface expression level of the mutant B7H4, and to correct for expression differences for each B7H4 mutant in general, data were normalized against the binding intensity of a non-cross blocking B7H4 specific reference antibody, using the following equation:

$$\text{Normalized } gMFI_{aa\ position} = \left(\frac{gMFI_{Test\ Ab}}{gMFI_{Reference\ Ab}}\right)$$

in which C2 was used as reference antibody for C1-N52S and C3, and C1-N52S was used as reference antibody for C2, and in which 'aa position' refers to either a particular ala mutant of B7H4 or wild type (wt) B7H4.

To express loss or gain of binding of the antibodies on a linear Fold Change scale, the following calculation was used:

$$\text{Fold Change} = \text{Log}_{10}\left(\frac{\text{Normalized } gMFI_{ala\ mutant}}{\text{Normalized } gMFI_{wt}}\right)$$

Gain of binding in most cases will be caused by loss of binding of the reference antibody to specific ala mutants.

Upon these calculations, amino acid positions for which, upon replacing the amino acid with alanine, there is no loss or gain of binding by a particular antibody will give as result '0', gain of binding will result in '>0' and loss of binding will result in '<0'. To correct for sample variation, only B7H4 amino acid residues where the Fold Change in binding was lower than the mean Fold Change—1.5×SD, where SD is the standard deviation of calculated fold changes from four independent experiments for a particular test antibody, were considered 'loss of binding mutants'.

In case the gMFI of the reference antibody for a particular B7H4 mutant was lower than the mean gMFI-2.5×SD of the mean $gMFI_{Control\ Ab}$, data were excluded from analysis (as for those B7H4 mutants it was assumed expression levels were not sufficient).

FIG. 3 shows the Fold Change in binding of the B7H4 antibodies to B7H4 variants with ala mutations in the ECD, with the amino acid residues where the Fold Change in binding was lower than the mean Fold Change—1.5×SD annotated. The Fold Change is indicated in FIG. 3 as Z-score. The results indicate that:

binding of antibody C1-N52S is at least dependent on aa S151, V157, D158, Y159, E164, L166, W173, P175, P177, V179, W181, F199, M208, V210, T222, Y223, V240, E242 and I245, which are in the IgC domain of human B7H4, binding of antibody C2 is at least dependent on aa R98, G99, R116, K118, N119 and D124, which are in the IgV of human B7H4, and binding of antibody C3 is at least dependent on aa N156, E164, V217 and R248, which are in the IgC domain of human B7H4, and antibodies C1-N52S, C2 and C3 recognize distinct functional epitopes on B7H4.

Example 8—Binding of B7H4 Monospecific and CD3xB7H4 Bispecific Antibodies to B7H4 from Various Species First, binding of bispecific CD3xB7H4 antibodies and monospecific B7H4 antibodies to HEK-293F cells transiently transfected with human B7H4 or with cynomolgus monkey (*Macaca fascicularis*) B7H4 was analyzed by flow cytometry. Non-transfected HEK-293F cells were used as negative control; these cells were (also) confirmed not to express CD3.

Cells ($3\times10^4$ cells/well) were incubated in polystyrene 96-well round-bottom plates (Greiner bio-one, cat. no. 650180) with serial dilutions of antibodies (ranging from 0.000458 to 30 µg/mL in 4-fold dilution steps) in 100 µL PBS/0.1% BSA/0.02% azide (staining buffer) at 4° C. for 30 min. Experiments were performed in technical duplicate. After washing twice in staining buffer, cells were incubated in 50 µL secondary antibody at 4° C. for 30 min. As a secondary antibody, R-Phycoerythrin (PE)-conjugated goat-anti-human IgG F(ab')$_2$ (1:500 in FACS buffer; Jackson ImmunoResearch Laboratories, Inc., West Grove, Pa., cat. no. 109-116-098), was used. Cells were washed twice in staining buffer, re-suspended in 30 µL FACS buffer containing Topro-3 (1:10,000 dilution) and analyzed on an iQue Screener (Intellicyt Corporation, USA). Binding curves were analyzed using non-linear regression (sigmoidal dose-response with variable slope) using Graph Pad Prism V7.02 software (GraphPad Software, San Diego, Calif., USA).

FIG. 4 shows that both IgG1-B7H4-C1-N52S-FEAR and bsIgG1-huCD3-H101G-FEALxB7H4-C1-N52S-FEAR bound to cells expressing human B7H4 or cynomolgus monkey B7H4.

Next, binding to HEK-293F cells transiently transfected with B7H4 from dog, rabbit, rat, mouse or pig was determined as described above. FIG. 5 shows that IgG1-B7H4-C1-N52S-FEAR and bsIgG1-huCD3-H101G-FEALxB7H4-C1-N52S-FEAR bound to B7H4 from dog, rabbit, rat and mouse to varying degrees; for each the apparent affinity (EC50) of the bsIgG1-huCD3-H101G-FEALxB7H4-C1-N52S-FEAR was lower than that of IgG1-B7H4-C1-N52S-FEAR. bsIgG1-huCD3-H101G-FEALxB7H4-C1-N52S-FEAR was not able to bind to pig B7H4, while IgG1-B7H4-C1-N52S-FEAR bound weakly and only at the highest antibody concentrations tested.

The EC50s for binding to human and cynomolgus monkey B7H4 of bsIgG1-huCD3-H101G-FEALxB7H4-C1-N52S-FEAR and IgG1-B7H4-C1-N52S-FEAR were in a similar range.

Similar studies were performed to compare binding of IgG1-B7H4-C1-052S-FEAR, IgG1-B7H4-C3-FEAR, IgG1-B7H4-C4-FEAR, IgG1-B7H4-C2-FEAR and IgG1-B7H4-C5-FEAR to B7H4 from different species (human, cynomolgus, mouse, rat, rabbit, dog, and pig). FIG. 6 shows that binding to HEK cells transfected with human and cynomolgus B7H4 was similar for the tested antibodies. Similar results were obtained with cells expressing rabbit and dog B7H4. However, binding to mouse B7H4 of IgG1-B7H4-C1-N52S-FEAR appeared lower relative to the binding of IgG1-B7H4-C3-FEAR, IgG1-B7H4-C4-FEAR, IgG1-B7H4-C2-FEAR, and IgG1-B7H4-C5-FEAR, which is in conformity with the results in example 3. Also, binding of gG1-B7H4-C1-N52S-FEAR and IgG1-B7H4-C3-FEAR to rat B7H4 appeared lower relative to IgG1-B7H4-C4-FEAR, IgG1-B7H4-C2-FEAR, and IgG1-B7H4-C5-FEAR. Furthermore, while IgG1-B7H4-C4-FEAR, IgG1-B7H4-C2-FEAR and IgG1-B7H4-C5-FEAR bound to pig B7H4, binding of IgG1-B7H4-C1-052S-FEAR was very weak and only apparent at the highest antibody concentration tested. Binding of IgG1-B7H4-C3-FEAR to pig B7H4 was undetectable.

Example 9—Binding of B7H4 Monospecific and CD3xB7H4 Bispecific Antibodies to B7H4-Expressing Human Tumor Cell Lines Binding of IgG1-B7H4-C1-N52S-FEAR and/or bsIgG1-huCD3-H101G-FEALxB7H4-C1-N52S-FEAR and/or bsIgG1-huCD3-FEALxB7H4-C1-N52S-FEAR to the B7H4-expressing human tumor cell lines MCF-7 (breast adenocarcinoma; ATCC, cat. No. HTB-22), MDA-MB-468 (breast adenocarcinoma; ATCC, cat. no. HTB-132) and SK-BR3 (breast adenocarcinoma; ATCC, cat. No. HTB-30), and of bsIgG1-huCD3-H101G-FEALxB7H4-C1-N52S-FEAR to B7H4-expressing human tumor cell lines NIH-OVCAR-3 (ovarian adenocarcinoma; ATCC, cat. no. HTB-161) or HCC1954 (breast ductal carcinoma; ATCC, cat. no. CRL-2338) was determined. Furthermore, binding of IgG1-B7H4-C1-N52S-FEAR, bsIgG1-huCD3-H101G-FEALxB7H4-C1-N52S-FEAR, IgG1-B7H4-C2-FEAR, bsIgG1-huCD3-FEALxB7H4-C2-FEAR or bsIgG1-huCD3-H101G-FEALxB7H4-C2-FEAR, IgG1-B7H4-C3-FEAR, bsIgG1-huCD3-H101G-FEALxB7H4-C3-FEAR, IgG1-B7H4-C4-FEAR, bsIgG1-huCD3-H101G-FEALxB7H4-C4-FEAR, IgG1-B7H4-C5-FEAR, and/or bsIgG1-huCD3-H101G-FEALxB7H4-05-FEAR to MDA-MB-468 and HCC1954 cells was determined. Solid tumor cell lines typically do not express CD3. As negative control, tumor cell line HeLa that showed no detectable B7H4 expression (cervix adenocarcinoma; ATCC, cat. no. CCL-2) was used. Binding was analyzed by flow cytometry as described above.

FIG. 7 shows that IgG1-B7H4-C1-N52S-FEAR and bsIgG1-huCD3-H101G-FEALxB7H4-C1-N52S-FEAR showed comparable dose-dependent binding to MCF-7 and MDA-MB-468 cells, with comparable maximum binding levels.

FIG. 8 shows dose-dependent binding of bsIgG1-huCD3-H101G-FEALxB7H4-C1-N52S-FEAR to NIH-OVCAR-3 and HCC1954 cells, and lack of detectable binding to a non-B7H4 expressing cell line, HeLa.

Binding of bsIgG1-huCD3-H101G-FEALxB7H4-C1-N52S-FEAR and bsIgG1-huCD3-FEALxB7H4-C1-N52S-FEAR to B7H4-expressing tumor cells was compared using MDA-MB-486 and SK-BR3 cells. FIG. 9 shows that bsIgG1-huCD3-H101G-FEALxB7H4-C1-N52S-FEAR and bsIgG1-huCD3-FEALxB7H4-C1-N52S-FEAR showed comparable dose-dependent binding to these cells, with comparable maximum binding levels.

FIG. 10 shows dose-dependent binding of the C1-N52S, C2, C3, C4, and C5 B7H4 antibodies in homodimer or bispecific antibody format to MDA-MB-468 and HCC1954 cells. The antibodies based on C4 and C5 showed most efficient binding, the antibodies based on C1-N52S and C2 showed intermediate binding efficiency, and the antibodies based on C3 showed the lowest binding efficiency. Maximum binding was comparable between the antibodies based on C1-N52S, C2, C4 and C5, but lower for the antibodies based on C3.

Example 10—Binding of B7H4 Antibody to Primary Tumor Cells

Primary tumor cells from an ovarian cancer patient were obtained from Discovery Life Sciences (Huntsville, Ala., USA; patient ID 110045042). Binding of IgG1-B7H4-C1-N52S-FEAR to tumor cells was assessed by flow cytometry: cells were seeded at 2×10$^4$ cells/well in polystyrene 96-well round-bottom plates (Greiner bio-one, cat. no. 650180), centrifuged and incubated with 50 µl Fixable Viability Stain FVS-BV510 (BD Biosciences, cat. no. 564406), 1:1000 diluted in PBS, at 4° C. for 30 min. After washing in staining buffer, cells were incubated with FITC-labeled IgG1-B7H4-C1-N52S-FEAR and a panel of CD3 (EF450 labeled; eBioscience, cat. no. 48-0037-42), CD45 (BV786 labeled; Biolegend, cat. no. 304048), CD14 (PE-Cy7 labeled; BD Biosciences, cat. no. 557742), CD86 (PerCP-Cy5.5 labeled; Biolegend, cat. no. 305420), CD163 (APC-Cy7 labeled; Biolegend, cat. no. 333622) and EpCAM (AF700 labeled; R&D systems, cat. no. FAB9601N) specific antibodies, at 4° C. for 30 min. After washing cells were resuspended in staining buffer and analyzed using a FACS Fortessa (BD Biosciences). Single cells were gated based on scatter FSC/SSC and live cells were identified by exclusion of FVS-BV510 positive cells. Tumor cells were identified as EpCAM positive cells.

Flow cytometric analysis showed that IgG1-B7H4-N52S-FEAR bound EpCAM-positive live tumor cells but not to monocytes or T cells within a dissociated tumor cell suspension of an ovarian cancer sample.

Example 11—Induction of T Cell Mediated Cytotoxicity In Vitro by CD3xB7H4 Bispecific Antibodies, Using Purified T Cells as Effector Cells at Varying Effector to Target Ratios To determine the efficiency of the T cell-mediated tumor cell kill in presence of bispecific antibodies bsIgG1-huCD3-FEALxB7H4-C1-N52S-FEAR and bsIgG1-huCD3-H101G-FEALx137H4-C1-N52S-FEAR, an in vitro cytotoxicity assay was performed using B7H4-positive tumor cell lines as target cells and purified T cells as effector cells, with varying effector to target cell (E:T) ratios.

T cells were obtained from healthy human donor buffy coats (Sanquin, Amsterdam, The Netherlands) and isolated using the RosetteSep™ human T cell enrichment cocktail (Stemcell Technologies, France, cat. no. 15061) according to the manufacturer's instructions. SK-BR3 cells (16,000 cells/well) were seeded into flat bottom 96-well plates (Greiner-bio-one, The Netherlands, cat. no. 655180) and left to adhere for 4 hours at 37° C. T cells were added to tumor cells at an effector to target (E:T) ratio of 2:1, 4:1 or 8:1. Serial dilutions of bsIgG1-huCD3-FEALxB7H4-C1-N52S-FEAR or bsIgG1-huCD3-H101G-FEALxB7H4-C1-N52S-FEAR were added (final concentration ranging from 10,000 to 0.0128 ng/mL; 5-fold dilutions) and plates were incubated for 72 hours at 37° C. Plates were washed 3 times with PBS, and cells were incubated with 150 µl/well of 10% alamarBlue® solution (Invitrogen, cat. no. DAL1100) for 4 hours at 37° C. As a positive control for cytotoxicity, cells were incubated with 16 µg/mL phenylarsine oxide (PAO; Sigma-Aldrich, cat. no. P3075; dissolved in dimethylsulfoxide [DMSO; Sigma-Adrich, cat. no. D2438]). AlamarBlue fluorescence, as a measure of metabolic activity of the tumor cell cultures and thus of viable tumor cells, was measured at 615 nm (OD615) on an EnVision plate reader (PerkinElmer). The absorbance of PAO-treated tumor cell samples was set as 0% viability and the absorbance of untreated tumor cell samples was set as 100% viability. The 'percentage viable cells' was calculated as follows:

% viable cells=([absorbance sample−absorbance PAO-treated target cells]/[absorbance untreated target cells−absorbance PAO-treated target cells])×100.

Dose-response curves and IC50 values were generated using non-linear regression analysis (sigmoidal dose-response with variable slope) using Graph Pad Prism V7.02 software (GraphPad Software, San Diego, Calif., USA).

FIG. 11 shows that T cell mediated cytotoxicity was observed at all E:T ratio's, with maximal tumor cell killing (less than 10% viable tumor cells) observed at an E:T ratio of 8:1.

Example 12—Induction of Cytotoxicity In Vitro in Various Tumor Cell Lines by CD3xB7H4 Bispecific Antibodies and Correlation with B7H4 Expression Level The T cell-mediated kill of bispecific antibodies bsIgG1-huCD3-FEALxB7H4-C1-N52S-FEAR and bsIgG1-huCD3-H101G-FEALxB7H4-C1-N52S-FEAR of various B7H4 expressing tumor cell lines was determined in an in vitro cytotoxicity assay as described above, using an E:T ratio of 8:1. The following cell lines were used: MCF-7, MDA-MB-486, SK-BR3, NIH-OVCAR-3, HCC1954, and NCI-H1650. From each incubation, 150 µL supernatants containing T cells was transferred to U-bottom 96 Well culture plates (CellStar, cat. no. 650180) prior to washing and alamarBlue incubation (to determine T cell activation and cytokine release, as described below)

For these tumor cell lines, the expression of B7H4 was quantified by quantitative flow cytometry (Human IgG calibrator, BioCytex) according to the manufacturer's instructions, using bsIgG1-huCD3-H101G-FEALxB7H4-C1-N52S-FEAR to detect B7H4.

FIG. 12 shows both bsIgG1-huCD3-FEALxB7H4-C1-N52S-FEAR and bsIgG1-huCD3-H101G-FEALxB7H4-C1-N52S-FEAR induced dose-dependent T cell mediated cytotoxicity in MCF-7, MDA-MB-486, SK-BR3, NIH-OVCAR-3 and HCC1954 cells in vitro. While maximum cytotoxic activity (<10% viable tumor cells) was achieved for both bsAb variants, this occurred at lower concentrations for bsIgG1-huCD3-FEALxB7H4-C1-N52S-FEAR in comparison with bsIgG1-huCD3-H101G-FEALxB7H4-C1-N52S-FEAR (Table 13).

No significant relation between tumor cell lysis and the level of B7H4 expression (FIG. 13A) was observed for either bsIgG1-huCD3-FEALxB7H4-C1-N52S-FEAR or bsIgG1-huCD3-H101G-FEALxB7H4-C1-N52S-FEAR (FIG. 13B). FIG. 13B shows the IC50 of T cell-mediated kill, using T cells derived from 4-6 donors, in the presence of bsIgG1-huCD3-FEALxB7H4-C1-N52S-FEAR or bsIgG1-huCD3-H101G-FEALxB7H4-C1-N52S-FEAR for each cell line, with the cell lines arranged from lowest to highest level of B7H4 expression. This means that T cell mediated killing can occur over a wide range of B7H4 expression levels.

Table 13 summarizes results across a panel of 5 cell lines and 4 donors.

TABLE 13

Induction of cytotoxicity in vitro in various tumor
cell lines by CD3xB7H4 bispecific antibodies.
IC50 range (4 donors each cell line) (μg/ml)

| cell line | CD3-H101GxB7H4 | | CD3x67H4 | |
|---|---|---|---|---|
| | lowest | highest | lowest | highest |
| MCF7 | 0.55 | 1.29 | 0.012 | 0.025 |
| OVCAR3 | 0.09 | 1.629 | 0.003 | 0.012 |
| NCI-H16650 | 1.67 | 5.07 | N.D. | N.D. |
| MDA-MB-468 | 0.08 | 0.16 | 0.001 | 0.004 |
| HCC1954 | 0.06 | 0.22 | 0.001 | 0.008 |
| SK-BR3 | 0.09 | 0.22 | 0.002 | 0.016 | bsIgG1-huCD3-H101G-FEALxB7H4-C1-N52S-FEAR also induced dose-dependent T-cell mediated cytotoxicity of the tested NCI-H1650 NSCLC cell line.

Example 13—Induction of T Cell Activation and Cytokine Production In Vitro by CD3xB7H4 Bispecific Antibodies in the Presence of B7H4-Positive Tumor Cells The U-bottom 96 well culture plates containing the supernatants collected during the in vitro T cell-mediated cytotoxicity experiments described in example 12 were centrifuged (300×g) for 3 min at 4° C., after which 75 μL of supernatant was transferred to a new plate for cytokine production measurement, and T cells were kept to assess T cell activation (described below). Cytokine production was analyzed by a multiplex U-plex assay (MeSo Scale Discovery, USA, cat. no. K15049K) according to manufacturer's instructions.

T cells were stained for T cell markers CD3 (1:200; eBioscience, clone OKT3, conjugated to eFluor450), CD4 (1:50; eBioscience, clone OKT4, conjugated to APC-eFluor780), CD8 (1:100; Biolegend, clone RPA-T8, conjugated to AF700) and T cell activation markers CD69 (1:50; BD Biosciences, clone AB2439, conjugated to APC), CD25 (1:50; eBioscience, clone BC96, conjugated to PE-Cy7) and CD279/PD1 (1:50; Biolegend, clone EH12.2H7, conjugated to BV605). Single stained samples with Ultracomp beads (5 μL; Invitrogen, cat. no. 01-2222-42) were included and used for compensation adjustments of the flow cytometer. After 30 min of incubation at 4° C., plates were washed three times with PBS/0.1% BSA/0.02% azide (staining buffer). Cells were resuspended in 120 μL staining buffer and analyzed using a FACS Fortessa (BD Biosciences). Data were processed using FlowJo (BD Biosciences).

Dose-response curves, EC50, EC90 and EC99 values were calculated using non-linear regression analysis (sigmoidal dose-response with variable slope) using GraphPad Prism V7.02 software (GraphPad Software, San Diego, Calif., USA).

FIG. 14A shows T cell activation in the presence of bsIgG1-huCD3-FEALxB7H4-C1-N52S-FEAR or bsIgG1-huCD3-H101G-FEALxB7H4-C1-N52S-FEAR for the B7H4-positive tumor cell lines, as defined by the expression of activation markers CD69 on CD8+ T cells (determined by flow cytometry). FIG. 14B shows the EC50 of T cell activation, using T cells derived from 3-4 donors, for each of the tumor cell lines.

Overall, a subset (approximately 20-50% at the highest antibody concentration) of CD8+ T cells became activated in the presence of either bsIgG1-huCD3-FEALxB7H4-C1-N52S-FEAR or bsIgG1-huCD3-H101G-FEALxB7H4-C1-N52S-FEAR. T cell activation induced by bsIgG1-huCD3-H101G-FEALxB7H4-C1-N52S-FEAR generally occurred at higher concentrations than that induced by bsIgG1-huCD3-FEALxB7H4-C1-N52S-FEAR (FIG. 14A). The EC50 of T cell activation for both bispecific antibodies was variable between target cell line used and between donors (FIG. 14B).

Production of cytokines was assessed in supernatants of the tumor cell-T cell cultures by Mesoscale Discovery U-plex multiplex ELISA. Of the 10 cytokines analyzed across the cell line panel, using T cells from 4 donors, significant increases in cytokine levels were primarily observed for IFN-gamma and IL-8 (>2000 pg/ml). IL-4, IL-6 and IL-13 were modulated at much lower levels (<500 pg/ml), while IL-1beta, IL-2, IL-10, IL-12p70, and TNFalpha levels were generally below 50 pg/ml. Because IFN-gamma changes were robustly and consistently detected and IFN-gamma is one of the core cytokines elevated in serum of patients with cytokine release syndrome, the data for this cytokine is represented.

FIG. 15 shows the levels of IFN-gamma in the supernatant of T cell-tumor cell co-cultures at antibody concentrations that induced T cell mediated cytotoxicity in 50%, 90% and 99% of tumor cells (EC50, EC90, EC99, resp) in the presence of bsIgG1-huCD3-FEALxB7H4-C1-N52S-FEAR and bsIgG1-huCD3-H101G-FEALxB7H4-C1-N52S-FEAR, using T cells from at least 3 donors analyzed per cell line. Cytokine production levels varied per donor and per target tumor cell line. Nevertheless, at antibody concentrations that induced the same level (%) of tumor cell killing, in general lower cytokine production levels were seen after exposure of T cell-tumor cell co-cultures to bsIgG1-huCD3-H101G-FEALxB7H4-C1-N52S-FEAR compared to that after exposure to bsIgG1-huCD3-FEALxB7H4-C1-N52S-FEAR. Thus, at the same level of tumor cell killing, incubation with bsIgG1-huCD3-H101G-FEALxB7H4-C1-N52S-FEAR resulted in lower cytokine production than bsIgG1-huCD3-FEALxB7H4-C1-N52S-FEAR.

Example 14—Non-Clinical Safety Studies of CD3xB7H4 Bispecific Antibodies in Cynomolgus Monkeys The non-clinical safety profile of bsIgG1-huCD3-FEALxB7H4-C1-N52S-FEAR and bsIgG1-huCD3-H101G-FEALxB7H4-C1-N52S-FEAR was evaluated in non-human primates (cynomolgus monkeys, Macaca fascicularis, originating from Mauritius) at Citoxlab, France. Cynomolgus monkeys were considered the only relevant species for non-clinical safety studies based on the species-specificity of the CD3 arms of bsIgG1-huCD3-FEALxB7H4-C1-N52S-FEAR and bsIgG1-huCD3-H101G-FEALxB7H4-C1-N52S-FEAR, and furthermore due to similar binding of the B7H4 arm to human and cynomolgus B7H4 and further pharmacological findings. These studies were conducted in compliance with animal health regulations (Council Directive No. 2010/63/EU of 22

Sep. 2010 and French decret No. 2013-118 of 1 Feb. 2013 on the protection of animals used for scientific purposes).

The aim of the studies were to determine the potential toxicity and toxicokinetics of the CD3xB7H4 bispecific antibodies. Here only the results of the toxicokinetics and the determination of cytokine levels in plasma are described.

In two separate studies, the animals were treated with a single dose of 0.1, 1, 3 or 10 mg/kg bsIgG1-huCD3-H101G-FEALxB7H4-C1-N52S-FEAR or bsIgG1-huCD3-FEALxB7H4-C1-N52S-FEAR (one female animal per dose) by intravenous (IV) infusion. The day of infusion was indicated as Day 1 in the study. Blood samples were obtained twice before dosing and 0.5h, 2h 4h, 12h, 24h and 48h after dosing for evaluation of the toxicokinetic profile and plasma cytokine levels, and additionally 168, 336 and 504 hours after dosing for toxicokinetics.

Cytokine Levels

Plasma samples were analyzed for cytokine levels (IL-1β, IL-2, IL-4, IL-5, IL-6, IL-8, IL-10, TNF, IL-12p70, IL-15 and CCL2/MCP1) using Luminex xMAP technology.

BsIgG1-huCD3-H101G-FEALxB7H4-C1-N52S-FEAR administration to cynomolgus monkey produced only minor changes in plasma cytokine levels, which were considered unrelated to test compound, whereas administration of bsIgG1-huCD3-FEALxB7H4-C1-N52S-FEAR resulted in dose-dependent increase of IL-6 and MCP-1 levels, as shown in FIG. 16.

The lower cytokine levels produced after treatment with bispecific BsIgG1-huCD3-H101G-FEALxB7H4-C1-N52S-FEAR, as compared with BsIgG1-huCD3-FEALxB7H4-C1-N52S-FEAR antibody, may offer an advantage in a clinical setting.

Toxicokinetics

Plasma concentrations of CD3xB7H4 bispecifics were determined using a generic IgG PK ECLIA method. Toxicokinetic parameters were estimated using Certara Phoenix WinNonlin pharmacokinetic software version 8.1 using a non-compartmental approach consistent with the intravenous infusion injection route of administration. FIG. 17 shows that the toxicokinetic profiles of both CD3xB7H4 bispecific antibodies were highly comparable up to 7 days post-dose, with both showing dose-related plasma exposure.

A pharmacokinetic modeling exercise was undertaken to assess whether the projected clinical dose range required by the BsIgG1-huCD3-H101G-FEALxB7H4-C1-N52S-FEAR variant with lower CD3 affinity would be unsustainably high. A PK model was used that was informed by observations in cynomolgus monkey. The clinical dose range was derived that is expected to give rise to one-week average plasma exposure equal to the EC50 to EC90 for T cell mediated cell kill as observed in vitro. The resulting dose range was considered feasible and this aspect gave no reason a priori to favor one type of bispecific antibody over the other (BsIgG1-huCD3-H101G-FEALxB7H4-C1-N52S-FEAR vs. the BsIgG1-huCD3-FEALxB7H4-C1-N52S-FEAR).

Example 15—B7H4 Expression in Various Human Cancer Indications

B7H4 mRNA levels were extracted from the Omicsoft TCGA database and visualized using Oncoland software (Qiagen, USA).

FIG. 18 shows the B7H4 mRNA expression levels in a range of primary solid tumors, ranked according to median of the expression. mRNA expression was found in a wide range of cancer indication and varied within each indication, with highest median expression found in uterine carcinosarcoma (UCS), bladder urothelial carcinoma (BLCA), pancreatic adenocarcinoma (PAAD), lung squamous cell carcinoma (LUSC), breast invasive carcinoma (BRCA), uterine corpus endometrial carcinoma (UCEC), ovarian serous cystadenocarcinoma (OV) and cholangiocarcinoma (CHOL).

Protein expression of B7H4 in colon, lung (small cell lung cancer, SCLC and non-small cell lung cancer, NSCLC), stomach, pancreatic, bladder, cervical, head and neck, breast (including triple-negative breast cancer, TNBC), ovarian, esophageal, kidney, prostate and uterine cancer and cholangiocarcinoma, was analyzed by immunohistochemistry (IHC) on tissue microarrays (TMA; all purchased from BioMax). Prior to staining, freshly cut TMA sections (5 µm) were deparaffinized and incubated with Target Retrieval Solution pH9 (DAKO, S2367; 30 min at 97° C., 60 min cool down). B7H4 IHC was performed using a commercial rabbit anti-human B7-H4 monoclonal antibody (clone D1M8I, #14572, Cell Signaling Technologies) at optimal dilution (1:25; final concentration 2.6 µg/mL) for 30 min (RT) on a LabVision autostainer platform. Subsequently, sections were incubated with anti-rabbit IgG polymer (Envision™ FLEX+ rabbit (DAKO, S2022), washed and incubated with DAKO Liquid DAB+ Substrate chromogen system (DAKO, K3468). Hematoxylin (DAKO, S3301) was used to detect nucleated cells. Cytokeratin (to determine the tumor region of interest, ROI) IHC was performed with mouse anti-cytokeratin antibody mix (clones AE1/AE3) on Ventana Benchmark using OptiView detection. Cytokeratin was visualized with DAB and nuclei counterstained with hematoxylin using default Ventana reagents. Stained TMA sections were digitized at 20× magnification on a AxioScan (Zeiss). Initially, manual scoring was performed to determine the average B7H4 staining intensity (negative-low-medium-high) and the percentage of tumor cores with >10% B7H4-positive tumor cells.

Subsequently, automated scoring was performed. The tumor ROI was defined using cytokeratin mask on TMA sections adjacent to those stained for B7H4. B7H4 staining intensity in the tumor ROI was quantified (negative, weak (1), moderate (2) or string (3) and the percentage of B7H4 percentage positive tumor cells (range 0-100%) was determined using HALO image analysis software. For each indication, the percentage of tumor cores with >10% B7H4-positive tumor cells was determined.

Table 14 shows B7H4 protein expression determined by IHC analysis of BioMax TMAs. No to very low B7H4 expression was seen in colon, prostate, kidney, and small cell lung cancer samples. In samples from the other indications the B7H4 expression varied, with increasing B7H4 expression found in stomach cancer, pancreatic cancer, cholangiocarcinoma, oesophageal cancer, bladder cancer, non-small cell lung cancer (in particular squamous NSCLC), cervical cancer, head and neck cancer, breast cancer (triple negative breast cancer [TNBC] and non-TNBC), ovarian cancer, and uterine cancer.

TABLE 14

B7H4 protein expression determined by IHC analysis of BioMax TMAs. ND = not determined.

| Indication (BioMax TMA) | | Manual scoring | | Automated scoring |
| --- | --- | --- | --- | --- |
| | | >10% B7H4 positive (any intensity, by visual assessment) | Staining intensity | >10% B7H4 positive (1+ and above, by digital image analysis) |
| Colon cancer (n = 64) | | 0% | Negative | |
| Lung cancer | SCLC (n = 60) | 1% | Negative-Low | |
| NSCLC | AC (n = 82) | 17% | Low | ND |
| | SQCC (n = 95) | 48% | Medium | ND |
| Stomach cancer (n = 90) | | 17% | Low | |
| Pancreatic cancer (n = 60) | | 25% | Low | ND |
| Cholangiocarcinoma (n = 98) | | 31% | Low | 16% |
| Bladder cancer (n = 60) | | 43% | Low-Medium | 25% |
| Cervical cancer (n = 60) | | 52% | Low-Medium | 27% |
| Head and Neck cancer (n = 92) | | 47% | Low-Medium | 23% |
| Breast cancer | all (n = 232) | 78% | Medium-High | 72% |
| | TNBC (n = 35) | 89% | Medium-High | ND |
| Ovarian cancer (n =74) | | 82% | Medium-High | 68% |
| Uterine cancer (n =73) | | 82% | Medium-High | 75% |
| Esophageal cancer (n = 53) | | 36% | Low | ND |
| Kidney cancer (n = 83) | | 9% | Negative | ND |
| Prostate cancer (n = 57) | | 1% | Negative | ND |

The invention claimed is:

1. An antibody comprising a first antigen-binding region which binds to human B7H4, wherein the first antigen-binding region comprises a variable heavy chain (VH) region comprising:
   a CDR1 comprising the sequence of SEQ ID NO: 26,
   a CDR2 comprising the sequence of SEQ ID NO: 30, and
   a CDR3 comprising the sequence of SEQ ID NO: 28
and a variable light chain (VL) region comprising:
   a CDR1 comprising the sequence of SEQ ID NO: 34,
   a CDR2 comprising the sequence GAS, and
   a CDR3 comprising the sequence of SEQ ID NO: 35, and
said antibody further comprising a second antigen-binding region which binds to human CD3.

2. An antibody comprising a first antigen-binding region which binds to human B7H4, wherein the first antigen-binding region comprises a variable heavy chain (VH) region comprising the sequence of SEQ ID NO. 29 and a variable light chain (VL) region comprising the sequence of SEQ ID NO. 33, said antibody further comprising a second antigen-binding region which binds to human CD3.

3. The antibody according to claim 1, wherein the second antigen-binding region binds to human CD3ε.

4. The antibody according to claim 1, wherein the second antigen-binding region comprises a variable heavy chain (VH) region comprising:
   a CDR1 comprising the sequence of SEQ ID NO: 18,
   a CDR2 comprising the sequence of SEQ ID NO: 19, and
   a CDR3 comprising the sequence of SEQ ID NO: 20 or SEQ ID NO: 21,
and a variable light chain (VL) region comprising:
   a CDR1 comprising the sequence of SEQ ID NO: 23,
   a CDR2 comprising the sequence GTN, and
   a CDR3 comprising the sequence of SEQ ID NO: 24.

5. The antibody according to claim 4, wherein the CDR3 of the VH region of the second antigen-binding region comprises the sequence of SEQ ID NO: 21.

6. The antibody according to claim 2, wherein the second antigen-binding region comprises a heavy chain variable (VH) region comprising the sequence of SEQ ID NO: 16 or 17 and a light chain variable (VL) region comprising the sequence of SEQ ID NO: 22.

7. The antibody according to claim 6, wherein the second antigen-binding region comprises a VH region comprising the sequence of SEQ ID NO: 17.

8. The antibody according to claim 5, wherein the antibody is a full-length antibody.

9. The antibody according to claim 7, wherein the antibody is a full-length antibody.

10. The antibody according to claim 5, wherein the antibody comprises a human IgG1 heavy chain constant region.

11. The antibody according to claim 7, wherein the antibody comprises a human IgG1 heavy chain constant region.

12. The antibody according to claim 5, wherein said antibody comprises a first heavy chain and a second heavy chain, wherein the amino acid in the position corresponding to K409 in a human IgG1 heavy chain is R in said first heavy chain, and the amino acid in the position corresponding to F405 in a human IgG1 heavy chain is L in said second heavy chain, or vice versa, and wherein the amino acid positions are numbered according to Eu numbering.

13. The antibody according to claim 7, wherein said antibody comprises a first heavy chain and a second heavy chain, wherein the amino acid in the position corresponding to K409 in a human IgG1 heavy chain is R in said first heavy chain, and the amino acid in the position corresponding to F405 in a human IgG1 heavy chain is L in said second heavy chain, or vice versa, and wherein the amino acid positions are numbered according to Eu numbering.

14. The antibody according to claim 5, wherein the antibody comprises a first heavy chain and a second heavy chain, and wherein in both the first heavy chain and the second heavy chain, the amino acid residues at the positions corresponding to positions L234, L235 and D265 in a human IgG1 heavy chain according to Eu numbering are F, E and A, respectively.

15. The antibody according to claim 7, wherein the antibody comprises a first heavy chain and a second heavy chain, and wherein in both the first heavy chain and the second heavy chain, the amino acid residues at the positions corresponding to positions L234, L235 and D265 in a human IgG1 heavy chain according to Eu numbering are F, E and A, respectively.

16. The antibody according to claim 5, wherein said antibody comprises a human kappa (κ) light chain and/or a human lambda (λ) light chain.

17. The antibody according to claim 7, wherein said antibody comprises a human kappa (κ) light chain and/or a human lambda (λ) light chain.

18. The antibody according to claim 5, wherein said first antigen binding region which binds to human B7H4 is comprised in a first heavy chain and a first light chain, said first heavy chain comprising said VH region and a human IgG1 heavy chain constant region and said first light chain comprising said VL region and a human kappa light chain constant region; and wherein said second antigen binding region which binds to human CD3 is comprised in a second heavy chain and a second light chain, said second heavy chain comprising said VH region and a human IgG1 heavy chain constant region and said second light chain comprising said VL region and a human lambda light chain constant region.

19. The antibody according to claim 7, wherein said first antigen binding region which binds to human B7H4 is comprised in a first heavy chain and a first light chain, said first heavy chain comprising said VH region and a human IgG1 heavy chain constant region and said first light chain comprising said VL region and a human kappa light chain constant region; and wherein said second antigen binding region which binds to human CD3 is comprised in a second heavy chain and a second light chain, said second heavy chain comprising said VH region and a human IgG1 heavy chain constant region and said second light chain comprising said VL region and a human lambda light chain constant region.

20. The antibody according to claim 18, wherein said first IgG1 heavy chain constant region comprises the sequence of SEQ ID NO. 61 and said second IgG1 heavy chain constant region comprises the sequence of SEQ ID NO. 60, and wherein said kappa light chain constant region comprises the sequence of SEQ ID NO. 63 and said lambda light chain constant region comprises the sequence of SEQ ID NO. 64.

21. The antibody according to claim 19, wherein said first IgG1 heavy chain constant region comprises the sequence of SEQ ID NO. 61 and said second IgG1 heavy chain constant region comprises the sequence of SEQ ID NO. 60, and wherein said kappa light chain constant region comprises the sequence of SEQ ID NO. 63 and said lambda light chain constant region comprises the sequence of SEQ ID NO. 64.

22. The antibody according to claim 20, wherein at least one of said IgG1 heavy chain constant regions lacks the C-terminal lysine.

23. The antibody according to claim 21, wherein at least one of said IgG1 heavy chain constant regions lacks the C-terminal lysine.

24. A bispecific antibody comprising a first antigen-binding region which binds to human B7H4, wherein the first antigen-binding region comprises a variable heavy chain (VH) region comprising:
   a CDR1 comprising the sequence of SEQ ID NO: 26,
   a CDR2 comprising the sequence of SEQ ID NO: 30, and
   a CDR3 comprising the sequence of SEQ ID NO: 28
and a variable light chain (VL) region comprising:
   a CDR1 comprising the sequence of SEQ ID NO: 34,
   a CDR2 comprising the sequence GAS, and
   a CDR3 comprising the sequence of SEQ ID NO: 35, and
said bispecific antibody further comprising a second antigen-binding region which binds to human CD3, wherein the second antigen-binding region comprises a VH region comprising:
   a CDR1 comprising the sequence of SEQ ID NO: 18,
   a CDR2 comprising the sequence of SEQ ID NO: 19, and
   a CDR3 comprising the sequence of SEQ ID NO: 21
and a VL region comprising:
   a CDR1 comprising the sequence of SEQ ID NO: 23,
   a CDR2 comprising the sequence GTN, and
   a CDR3 comprising the sequence of SEQ ID NO: 24.

25. A bispecific antibody comprising a first antigen-binding region which binds to human B7H4, wherein the first antigen-binding region comprises a variable heavy chain region comprising the sequence of SEQ ID NO. 29 and a variable light chain region comprising the sequence of SEQ ID NO. 33, said bispecific antibody further comprising a second antigen-binding region which binds to human CD3, wherein the second antigen-binding region comprises a variable heavy chain region comprising the sequence of SEQ ID NO. 17 and a variable light chain region comprising the sequence of SEQ ID NO. 22.

26. The bispecific antibody of claim 24, wherein the antibody further comprises a first heavy chain constant region and a second heavy chain constant region and a first light chain constant region and a second light chain constant region, wherein said first heavy chain constant region comprises the sequence of SEQ ID NO. 61 and said second heavy chain constant region comprises the sequence of SEQ ID NO. 60, and wherein said first light chain constant region comprises the sequence of SEQ ID NO. 63 and said second light chain constant region comprises the sequence of SEQ ID NO. 64.

27. The bispecific antibody of claim 25, wherein the antibody further comprises a first heavy chain constant region and a second heavy chain constant region and a first light chain constant region and a second light chain constant region, wherein said first heavy chain constant region comprises the sequence of SEQ ID NO. 61 and said second heavy chain constant region comprises the sequence of SEQ ID NO. 60, and wherein said first light chain constant region comprises the sequence of SEQ ID NO. 63 and said second light chain constant region comprises the sequence of SEQ ID NO. 64.

28. The bispecific antibody of claim 26, wherein at least one of the heavy chain constant regions lacks the C-terminal lysine.

29. The bispecific antibody of claim 27, wherein at least one of the heavy chain constant regions lacks the C-terminal lysine.

30. The bispecific antibody of claim 29, wherein both heavy chain constant regions lack the C-terminal lysine.

* * * * *

UNITED STATES PATENT AND TRADEMARK OFFICE
CERTIFICATE OF CORRECTION

| | |
|---|---|
| PATENT NO. | : 11,261,254 B1 |
| APPLICATION NO. | : 17/494545 |
| DATED | : March 1, 2022 |
| INVENTOR(S) | : Louise Koopman et al. |

It is certified that error appears in the above-identified patent and that said Letters Patent is hereby corrected as shown below:

On the Title Page

At Column 1, in item (30), Line 1 of the "Foreign Application Priority Data" section, delete "20164059" and insert -- 20164059.6 --.

Signed and Sealed this
Seventeenth Day of May, 2022

Katherine Kelly Vidal
*Director of the United States Patent and Trademark Office*

SEQUENCE LISTING

<160> NUMBER OF SEQ ID NOS: 71

<210> SEQ ID NO 1
<211> LENGTH: 282
<212> TYPE: PRT
<213> ORGANISM: Homo Sapiens

<400> SEQUENCE: 1

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
```

```
                145                 150                 155                 160
Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
                210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
                260                 265                 270

Leu Pro Leu Ser Pro Tyr Leu Met Leu Lys
                275                 280

<210> SEQ ID NO 2
<211> LENGTH: 282
<212> TYPE: PRT
<213> ORGANISM: Macaca fascicularis

<400> SEQUENCE: 2

Met Ala Ser Leu Gly Gln Ile Leu Phe Trp Ser Ile Ser Ile Ile
1               5                   10                  15

Phe Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
                35                  40                  45

Gly Glu Asp Gly Ile Leu Ser Cys Thr Phe Glu Pro Asp Ile Lys Leu
                50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
                130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
                210                 215                 220

Cys Met Ile Glu Asn Asp Ile Ala Lys Ala Thr Gly Asp Ile Lys Val
225                 230                 235                 240
```

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
            260                 265                 270

Leu Pro Leu Ala Pro Tyr Leu Met Leu Lys
        275                 280

<210> SEQ ID NO 3
<211> LENGTH: 282
<212> TYPE: PRT
<213> ORGANISM: Canis familiaris

<400> SEQUENCE: 3

Met Ala Ser Pro Gly Gln Asn Ile Phe Trp Ser Ile Ile Ser Val Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Leu Thr Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Met Gly Leu Val
65                  70                  75                  80

His Glu Phe Lys Glu Gly Lys Asp Asp Leu Ser Asp Gln Asp Glu Met
                85                  90                  95

Phe Arg Gly Arg Thr Ala Val Phe Ala Asp Gln Val Ile Gly Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Ile Pro Glu Val Asn Val Asp Tyr Asn
145                 150                 155                 160

Ala Ser Ser Glu Asn Leu Arg Cys Glu Ala Pro Arg Trp Phe Pro Gln
                165                 170                 175

Pro Thr Val Val Trp Ala Ser Gln Ala Asp Gln Gly Ala Asn Phe Ser
            180                 185                 190

Glu Val Phe Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Ile Lys Arg Arg Ser His Leu Gln Leu Leu Asn Ser
                245                 250                 255

Lys Ala Ser Leu Gly Val Ser Ser Phe Phe Ala Ile Ser Trp Val Leu
            260                 265                 270

Leu Pro Leu Ser Ser Tyr Leu Met Leu Lys
        275                 280

<210> SEQ ID NO 4
<211> LENGTH: 282
<212> TYPE: PRT
<213> ORGANISM: Oryctolagus cuniculus

<400> SEQUENCE: 4

```
Met Ala Ser Leu Gly Gln Ile Ile Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Leu Thr Ser Ala Gly Asn Ile
        35                  40                  45

Gly Glu Asp Gly Ile Leu Ser Cys Thr Phe Glu Pro Asp Ile Arg Leu
    50                  55                  60

Ser Asp Ile Val Ile Gln Trp Leu Lys Glu Gly Val Val Gly Leu Val
65                  70                  75                  80

His Glu Phe Lys Glu Gly Lys Asp Asp Leu Ser Asp Gln Asp Glu Met
                85                  90                  95

Phe Arg Gly Arg Thr Ala Val Phe Thr Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Leu Asp Tyr Asn
145                 150                 155                 160

Ala Ser Ser Glu Ser Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Val Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Ile Lys Arg Arg Ser Ser Leu Gln Leu Leu Asn Ser
                245                 250                 255

Arg Ala Ala Pro Ser Val Ser Pro Arg Ser Ala Val Gly Trp Leu Leu
            260                 265                 270

Leu Pro Leu Ser Ser Tyr Val Met Leu Lys
        275                 280

<210> SEQ ID NO 5
<211> LENGTH: 282
<212> TYPE: PRT
<213> ORGANISM: Rattus norvegicus

<400> SEQUENCE: 5

Met Ala Ser Leu Gly Gln Ile Ile Phe Trp Ser Ile Ile Asn Val Ile
1               5                   10                  15

Ile Ile Leu Ala Gly Ala Ile Val Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95
```

```
Phe Arg Gly Arg Thr Ala Val Phe Ala Asp Gln Val Val Gly Asn
                100                 105                 110

Ala Ser Leu Arg Leu Lys Asn Val Gln Leu Thr Asp Ala Gly Thr Tyr
        115                 120                 125

Thr Cys Tyr Ile His Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Glu Leu Leu Asn Ser
                245                 250                 255

Gly Pro Ser Pro Cys Val Ser Val Ser Ala Ala Gly Trp Ala Leu
            260                 265                 270

Leu Ser Leu Ser Cys Cys Leu Met Leu Arg
        275                 280

<210> SEQ ID NO 6
<211> LENGTH: 283
<212> TYPE: PRT
<213> ORGANISM: Mus musculus

<400> SEQUENCE: 6

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Gly Asn
                100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
```

```
            180                 185                 190
Glu Val Ser Asn Thr Ser Phe Glu Leu Asn Ser Glu Asn Val Thr Met
            195                 200                 205

Lys Val Ser Val Leu Tyr Asn Val Thr Ile Asn Thr Tyr Ser
        210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
                260                 265                 270

Leu Leu Ser Leu Ser Cys Cys Leu Met Leu Arg
                275                 280
```

<210> SEQ ID NO 7
<211> LENGTH: 282
<212> TYPE: PRT
<213> ORGANISM: Sus scrofa

<400> SEQUENCE: 7

```
Met Ala Ser Leu Gly Gln Val Val Phe Trp Ser Ile Ile Ser Ile Ile
1               5                   10                  15

Ile Ile Leu Ala Gly Ala Ile Ala Phe Ile Ile Gly Phe Gly Ile Ser
                20                  25                  30

Gly Arg His Ser Ile Thr Val Thr Thr Leu Thr Ser Ala Gly Asn Ile
            35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Thr Gly Leu Val
65                  70                  75                  80

His Glu Phe Lys Lys Gly Lys Asp Asp Leu Ser Asp Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Lys Leu Glu
130                 135                 140

Tyr Lys Thr Gly Ala Phe Ser Ile Pro Glu Val Asn Val Asp Ser Asn
145                 150                 155                 160

Ala Ser Ser Glu Ser Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Pro Glu Asn Val Thr Met
        195                 200                 205

Lys Val Val Ser Val Leu Tyr Asn Val Thr Ile Asn Thr Thr Tyr Ser
    210                 215                 220

Cys Met Ile Glu Asn Asp Ile Ala Lys Ala Thr Gly Asp Ile Arg Val
225                 230                 235                 240

Thr Asp Ser Glu Ile Lys Arg Gln Ser His Leu Gln Leu Leu Asn Ser
                245                 250                 255

Lys Ala Ser Leu Cys Leu Ser Ser Phe Val Ala Ile Ser Trp Val Leu
            260                 265                 270
```

```
Leu Pro Leu Cys Pro Tyr Leu Met Leu Lys
            275                 280

<210> SEQ ID NO 8
<211> LENGTH: 9
<212> TYPE: PRT
<213> ORGANISM: Artificial sequence
<220> FEATURE:
<223> OTHER INFORMATION: Nucleic acid motif for translation

<400> SEQUENCE: 8

Gly Cys Cys Gly Cys Cys Ala Cys Cys
1               5

<210> SEQ ID NO 9
<211> LENGTH: 534
<212> TYPE: PRT
<213> ORGANISM: Homo Sapiens

<400> SEQUENCE: 9

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
```

```
            290                 295                 300
Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
                355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
                420                 425                 430

Asn Gly Thr Tyr Ser Cys Leu Val Arg Asn Pro Val Leu Gln Gln Asp
                435                 440                 445

Ala His Gly Ser Val Thr Ile Thr Gly Gln Pro Met Thr Phe Pro Pro
                450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
                515                 520                 525

Asp Gly Gln Glu Ile Ala
                530

<210> SEQ ID NO 10
<211> LENGTH: 325
<212> TYPE: PRT
<213> ORGANISM: Artificial sequence
<220> FEATURE:
<223> OTHER INFORMATION: Domain swap

<400> SEQUENCE: 10

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
                35                  40                  45

Gly Glu Asp Gly Ile Leu Ser Cys Thr Phe Glu Pro Asp Ile Lys Leu
                50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
```

```
                115                 120                 125
Lys Cys Tyr Ile Ile Thr Ser Lys Gly Lys Gly Asn Ala Asn Leu Glu
130                 135                 140

Tyr Lys Thr Gly Ala Pro Tyr Ser Lys Pro Ser Met Thr Leu Glu Pro
145                 150                 155                 160

Asn Lys Asp Leu Arg Pro Gly Asp Thr Val Thr Ile Thr Cys Ser Ser
                165                 170                 175

Tyr Arg Gly Tyr Pro Glu Ala Glu Val Phe Trp Gln Asp Gly Gln Gly
                180                 185                 190

Val Pro Leu Thr Gly Asn Val Thr Thr Ser Gln Met Ala Asn Glu Gln
                195                 200                 205

Gly Leu Phe Asp Val His Ser Val Leu Arg Val Val Leu Gly Ala Asn
                210                 215                 220

Gly Thr Tyr Ser Cys Leu Val Arg Asn Pro Val Leu Gln Gln Asp Ala
225                 230                 235                 240

His Gly Ser Val Thr Ile Thr Gly Gln Pro Met Thr Phe Pro Pro Glu
                245                 250                 255

Ala Leu Trp Val Thr Val Gly Leu Ser Val Cys Leu Ile Ala Leu Leu
                260                 265                 270

Val Ala Leu Ala Phe Val Cys Trp Arg Lys Ile Lys Gln Ser Cys Glu
                275                 280                 285

Glu Glu Asn Ala Gly Ala Glu Asp Gln Asp Gly Glu Gly Glu Gly Ser
                290                 295                 300

Lys Thr Ala Leu Gln Pro Leu Lys His Ser Asp Ser Lys Glu Asp Asp
305                 310                 315                 320

Gly Gln Glu Ile Ala
                325

<210> SEQ ID NO 11
<211> LENGTH: 273
<212> TYPE: PRT
<213> ORGANISM: Artificial sequence
<220> FEATURE:
<223> OTHER INFORMATION: Domain swap

<400> SEQUENCE: 11

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
                35                  40                  45

Cys Cys Ser Phe Ser Pro Glu Pro Gly Phe Ser Leu Ala Gln Leu Asn
                50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
                115                 120                 125

Phe Gly Ser Ala Ala Val Ser Leu Gln Val Ala Ala Phe Ser Met Pro
                130                 135                 140

Glu Val Asn Val Asp Tyr Asn Ala Ser Ser Glu Thr Leu Arg Cys Glu
```

```
                  145                 150                 155                 160
Ala Pro Arg Trp Phe Pro Gln Pro Thr Val Val Trp Ala Ser Gln Val
                            165                 170                 175

Asp Gln Gly Ala Asn Phe Ser Glu Val Ser Asn Thr Ser Phe Glu Leu
            180                 185                 190

Asn Ser Glu Asn Val Thr Met Lys Val Val Ser Val Leu Tyr Asn Val
        195                 200                 205

Thr Ile Asn Asn Thr Tyr Ser Cys Met Ile Glu Asn Asp Ile Ala Lys
    210                 215                 220

Ala Thr Gly Asp Ile Lys Val Thr Glu Ser Glu Ile Lys Arg Arg Ser
225                 230                 235                 240

His Leu Gln Leu Leu Asn Ser Lys Ala Ser Leu Cys Val Ser Ser Phe
                245                 250                 255

Phe Ala Ile Ser Trp Ala Leu Leu Pro Leu Ser Pro Tyr Leu Met Leu
            260                 265                 270

Lys

<210> SEQ ID NO 12
<211> LENGTH: 484
<212> TYPE: PRT
<213> ORGANISM: Artificial sequence
<220> FEATURE:
<223> OTHER INFORMATION: Tagged protein

<400> SEQUENCE: 12

Leu Ile Ile Gly Phe Gly Ile Ser Gly Arg His Ser Ile Thr Val Thr
1               5                   10                  15

Thr Val Ala Ser Ala Gly Asn Ile Gly Glu Asp Gly Ile Leu Ser Cys
            20                  25                  30

Thr Phe Glu Pro Asp Ile Lys Leu Ser Asp Ile Val Ile Gln Trp Leu
        35                  40                  45

Lys Glu Gly Val Leu Gly Leu Val His Glu Phe Lys Glu Gly Lys Asp
    50                  55                  60

Glu Leu Ser Glu Gln Asp Glu Met Phe Arg Gly Arg Thr Ala Val Phe
65                  70                  75                  80

Ala Asp Gln Val Ile Val Gly Asn Ala Ser Leu Arg Leu Lys Asn Val
                85                  90                  95

Gln Leu Thr Asp Ala Gly Thr Tyr Lys Cys Tyr Ile Ile Thr Ser Lys
            100                 105                 110

Gly Lys Gly Asn Ala Asn Leu Glu Tyr Lys Thr Gly Ala Phe Ser Met
        115                 120                 125

Pro Glu Val Asn Val Asp Tyr Asn Ala Ser Ser Glu Thr Leu Arg Cys
    130                 135                 140

Glu Ala Pro Arg Trp Phe Pro Gln Pro Thr Val Val Trp Ala Ser Gln
145                 150                 155                 160

Val Asp Gln Gly Ala Asn Phe Ser Glu Val Ser Asn Thr Ser Phe Glu
                165                 170                 175

Leu Asn Ser Glu Asn Val Thr Met Lys Val Val Ser Val Leu Tyr Asn
            180                 185                 190

Val Thr Ile Asn Asn Thr Tyr Ser Cys Met Ile Glu Asn Asp Ile Ala
        195                 200                 205

Lys Ala Thr Gly Asp Ile Lys Val Thr Glu Ser Glu Ile Lys Arg Arg
    210                 215                 220

Ser His Leu Gln Leu Leu Asn Ser Lys Ala Ser Ile Glu Gly Arg Met
225                 230                 235                 240
```

```
Asp Pro Lys Ser Cys Asp Lys Thr His Thr Cys Pro Pro Cys Pro Ala
            245                 250                 255

Pro Glu Ala Glu Gly Ala Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Ala Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys His His His His His His His His
465                 470                 475                 480

Glu Pro Glu Ala

<210> SEQ ID NO 13
<211> LENGTH: 186
<212> TYPE: PRT
<213> ORGANISM: Homo Sapiens

<400> SEQUENCE: 13

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125
```

```
Tyr Trp Ser Lys Asn Arg Lys Ala Lys Ala Lys Pro Val Thr Arg Gly
        130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
        180                 185

<210> SEQ ID NO 14
<211> LENGTH: 127
<212> TYPE: PRT
<213> ORGANISM: Artificial sequence
<220> FEATURE:
<223> OTHER INFORMATION: binding domain sequence

<400> SEQUENCE: 14

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
                20                  25                  30

Val Ile His Trp Val Arg Gln Ala Pro Gly Gln Arg Phe Glu Trp Met
            35                  40                  45

Gly Trp Ile Asn Pro Tyr Asn Gly Asn Lys Glu Phe Ser Ala Lys Phe
        50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
                100                 105                 110

Tyr Met Asp Val Trp Gly Lys Gly Thr Thr Val Ile Val Ser Ser
            115                 120                 125

<210> SEQ ID NO 15
<211> LENGTH: 108
<212> TYPE: PRT
<213> ORGANISM: Artificial sequence
<220> FEATURE:
<223> OTHER INFORMATION: binding domain sequence

<400> SEQUENCE: 15

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
                20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
        50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105
```

```
<210> SEQ ID NO 16
<211> LENGTH: 125
<212> TYPE: PRT
<213> ORGANISM: Artificial sequence
<220> FEATURE:
<223> OTHER INFORMATION: binding domain sequence

<400> SEQUENCE: 16

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 17
<211> LENGTH: 125
<212> TYPE: PRT
<213> ORGANISM: Artificial sequence
<220> FEATURE:
<223> OTHER INFORMATION: binding domain sequence

<400> SEQUENCE: 17

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Gly Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 18
<211> LENGTH: 8
<212> TYPE: PRT
<213> ORGANISM: Artificial sequence
<220> FEATURE:
<223> OTHER INFORMATION: binding domain sequence

<400> SEQUENCE: 18

Gly Phe Thr Phe Asn Thr Tyr Ala
1               5
```

<210> SEQ ID NO 19
<211> LENGTH: 10
<212> TYPE: PRT
<213> ORGANISM: Artificial sequence
<220> FEATURE:
<223> OTHER INFORMATION: binding domain sequence

<400> SEQUENCE: 19

Ile Arg Ser Lys Tyr Asn Asn Tyr Ala Thr
1               5                   10

<210> SEQ ID NO 20
<211> LENGTH: 16
<212> TYPE: PRT
<213> ORGANISM: Artificial sequence
<220> FEATURE:
<223> OTHER INFORMATION: binding domain sequence

<400> SEQUENCE: 20

Val Arg His Gly Asn Phe Gly Asn Ser Tyr Val Ser Trp Phe Ala Tyr
1               5                   10                  15

<210> SEQ ID NO 21
<211> LENGTH: 16
<212> TYPE: PRT
<213> ORGANISM: Artificial sequence
<220> FEATURE:
<223> OTHER INFORMATION: binding domain sequence

<400> SEQUENCE: 21

Val Arg Gly Gly Asn Phe Gly Asn Ser Tyr Val Ser Trp Phe Ala Tyr
1               5                   10                  15

<210> SEQ ID NO 22
<211> LENGTH: 109
<212> TYPE: PRT
<213> ORGANISM: Artificial sequence
<220> FEATURE:
<223> OTHER INFORMATION: binding domain sequence

<400> SEQUENCE: 22

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 23
<211> LENGTH: 9
<212> TYPE: PRT
<213> ORGANISM: Artificial sequence
<220> FEATURE:
<223> OTHER INFORMATION: binding domain sequence

```
<400> SEQUENCE: 23

Thr Gly Ala Val Thr Thr Ser Asn Tyr
1               5

<210> SEQ ID NO 24
<211> LENGTH: 9
<212> TYPE: PRT
<213> ORGANISM: Artificial sequence
<220> FEATURE:
<223> OTHER INFORMATION: binding domain sequence

<400> SEQUENCE: 24

Ala Leu Trp Tyr Ser Asn Leu Trp Val
1               5

<210> SEQ ID NO 25
<211> LENGTH: 117
<212> TYPE: PRT
<213> ORGANISM: Artificial sequence
<220> FEATURE:
<223> OTHER INFORMATION: binding domain sequence

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Thr Ser Val Thr Ala Ala Asp Thr Ala Val Phe Tyr Cys Ala
                85                  90                  95

Arg Gly Leu Phe Asn Trp Asn Phe Asp Ser Trp Gly Gln Gly Thr Leu
            100                 105                 110

Val Thr Val Ser Ser
        115

<210> SEQ ID NO 26
<211> LENGTH: 8
<212> TYPE: PRT
<213> ORGANISM: Artificial sequence
<220> FEATURE:
<223> OTHER INFORMATION: binding domain sequence

<400> SEQUENCE: 26

Gly Gly Ser Phe Ser Gly Tyr Tyr
1               5

<210> SEQ ID NO 27
<211> LENGTH: 7
<212> TYPE: PRT
<213> ORGANISM: Artificial sequence
<220> FEATURE:
<223> OTHER INFORMATION: binding domain sequence

<400> SEQUENCE: 27

Ile Asn His Ser Gly Ser Thr
1               5
```

```
<210> SEQ ID NO 28
<211> LENGTH: 11
<212> TYPE: PRT
<213> ORGANISM: Artificial sequence
<220> FEATURE:
<223> OTHER INFORMATION: binding domain sequence

<400> SEQUENCE: 28

Ala Arg Gly Leu Phe Asn Trp Asn Phe Asp Ser
1               5                   10

<210> SEQ ID NO 29
<211> LENGTH: 117
<212> TYPE: PRT
<213> ORGANISM: Artificial sequence
<220> FEATURE:
<223> OTHER INFORMATION: binding domain sequence

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Ser His Ser Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Thr Ser Val Thr Ala Ala Asp Thr Ala Val Phe Tyr Cys Ala
                85                  90                  95

Arg Gly Leu Phe Asn Trp Asn Phe Asp Ser Trp Gly Gln Gly Thr Leu
            100                 105                 110

Val Thr Val Ser Ser
        115

<210> SEQ ID NO 30
<211> LENGTH: 7
<212> TYPE: PRT
<213> ORGANISM: Artificial sequence
<220> FEATURE:
<223> OTHER INFORMATION: binding domain sequence

<400> SEQUENCE: 30

Ile Ser His Ser Gly Ser Thr
1               5

<210> SEQ ID NO 31
<211> LENGTH: 117
<212> TYPE: PRT
<213> ORGANISM: Artificial sequence
<220> FEATURE:
<223> OTHER INFORMATION: binding domain sequence

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Gln His Ser Gly Ser Thr Asn Tyr Asn Pro Ser Leu Lys
```

```
            50                  55                  60
Ser Arg Val Thr Ile Ser Ile Asp Thr Ser Lys Asn Gln Phe Ser Leu
 65                  70                  75                  80

Lys Leu Thr Ser Val Thr Ala Ala Asp Thr Ala Val Phe Tyr Cys Ala
                 85                  90                  95

Arg Gly Leu Phe Asn Trp Asn Phe Asp Ser Trp Gly Gln Gly Thr Leu
            100                 105                 110

Val Thr Val Ser Ser
            115

<210> SEQ ID NO 32
<211> LENGTH: 7
<212> TYPE: PRT
<213> ORGANISM: Artificial sequence
<220> FEATURE:
<223> OTHER INFORMATION: binding domain sequence

<400> SEQUENCE: 32

Ile Gln His Ser Gly Ser Thr
 1               5

<210> SEQ ID NO 33
<211> LENGTH: 107
<212> TYPE: PRT
<213> ORGANISM: Artificial sequence
<220> FEATURE:
<223> OTHER INFORMATION: binding domain sequence

<400> SEQUENCE: 33

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Gly Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                 85                  90                  95

Thr Phe Gly Gln Gly Thr Thr Val Glu Ile Lys
            100                 105

<210> SEQ ID NO 34
<211> LENGTH: 6
<212> TYPE: PRT
<213> ORGANISM: Artificial sequence
<220> FEATURE:
<223> OTHER INFORMATION: binding domain sequence

<400> SEQUENCE: 34

Gln Gly Ile Arg Asn Asp
 1               5

<210> SEQ ID NO 35
<211> LENGTH: 9
<212> TYPE: PRT
<213> ORGANISM: Artificial sequence
<220> FEATURE:
<223> OTHER INFORMATION: binding domain sequence
```

```
<400> SEQUENCE: 35

Leu Gln His Asn Ser Tyr Pro Arg Thr
1               5

<210> SEQ ID NO 36
<211> LENGTH: 116
<212> TYPE: PRT
<213> ORGANISM: Artificial sequence
<220> FEATURE:
<223> OTHER INFORMATION: binding domain sequence

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser
        115

<210> SEQ ID NO 37
<211> LENGTH: 8
<212> TYPE: PRT
<213> ORGANISM: Artificial sequence
<220> FEATURE:
<223> OTHER INFORMATION: binding domain sequence

<400> SEQUENCE: 37

Gly Tyr Thr Phe Thr Asn Phe Trp
1               5

<210> SEQ ID NO 38
<211> LENGTH: 8
<212> TYPE: PRT
<213> ORGANISM: Artificial sequence
<220> FEATURE:
<223> OTHER INFORMATION: binding domain sequence

<400> SEQUENCE: 38

Ile Asp Pro Ser Asp Ser Tyr Thr
1               5

<210> SEQ ID NO 39
<211> LENGTH: 9
<212> TYPE: PRT
<213> ORGANISM: Artificial sequence
<220> FEATURE:
<223> OTHER INFORMATION: binding domain sequence

<400> SEQUENCE: 39

Ala Arg Glu Ile Thr Thr Val Asp Tyr
1               5
```

-continued

```
<210> SEQ ID NO 40
<211> LENGTH: 106
<212> TYPE: PRT
<213> ORGANISM: Artificial sequence
<220> FEATURE:
<223> OTHER INFORMATION: binding domain sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
                20                  25                  30

His Trp Tyr Gln Gln Lys Pro Gly Lys Ala Pro Lys Gly Trp Ile Tyr
            35                  40                  45

Asp Thr Ser Lys Leu Ala His Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys
            100                 105

<210> SEQ ID NO 41
<211> LENGTH: 5
<212> TYPE: PRT
<213> ORGANISM: Artificial sequence
<220> FEATURE:
<223> OTHER INFORMATION: binding domain sequence

<400> SEQUENCE: 41

Ser Ser Ile Ser Tyr
1               5

<210> SEQ ID NO 42
<211> LENGTH: 9
<212> TYPE: PRT
<213> ORGANISM: Artificial sequence
<220> FEATURE:
<223> OTHER INFORMATION: binding domain sequence

<400> SEQUENCE: 42

His Gln Arg Arg Ser Tyr Pro Phe Thr
1               5

<210> SEQ ID NO 43
<211> LENGTH: 121
<212> TYPE: PRT
<213> ORGANISM: Artificial sequence
<220> FEATURE:
<223> OTHER INFORMATION: binding domain sequence

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Gly Trp Val Arg Gln Ala Pro Gly Gln Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Arg Val Thr Ile Thr Arg Asp Thr Ser Thr Ser Thr Ala Tyr
```

```
                65                  70                  75                  80
Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120

<210> SEQ ID NO 44
<211> LENGTH: 8
<212> TYPE: PRT
<213> ORGANISM: Artificial sequence
<220> FEATURE:
<223> OTHER INFORMATION: binding domain sequence

<400> SEQUENCE: 44

Gly Tyr Thr Phe Thr Ser Tyr Trp
1               5

<210> SEQ ID NO 45
<211> LENGTH: 8
<212> TYPE: PRT
<213> ORGANISM: Artificial sequence
<220> FEATURE:
<223> OTHER INFORMATION: binding domain sequence

<400> SEQUENCE: 45

Ile Tyr Pro Gly Gly Gly Tyr Thr
1               5

<210> SEQ ID NO 46
<211> LENGTH: 14
<212> TYPE: PRT
<213> ORGANISM: Artificial sequence
<220> FEATURE:
<223> OTHER INFORMATION: binding domain sequence

<400> SEQUENCE: 46

Ala Arg Leu Asp Gly Ser Ser Tyr Arg Gly Ala Met Asp Ser
1               5                   10

<210> SEQ ID NO 47
<211> LENGTH: 107
<212> TYPE: PRT
<213> ORGANISM: Artificial sequence
<220> FEATURE:
<223> OTHER INFORMATION: binding domain sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys
```

```
<210> SEQ ID NO 48
<211> LENGTH: 6
<212> TYPE: PRT
<213> ORGANISM: Artificial sequence
<220> FEATURE:
<223> OTHER INFORMATION: binding domain sequence

<400> SEQUENCE: 48

Gln Gly Phe Asn Lys Tyr
1               5

<210> SEQ ID NO 49
<211> LENGTH: 9
<212> TYPE: PRT
<213> ORGANISM: Artificial sequence
<220> FEATURE:
<223> OTHER INFORMATION: binding domain sequence

<400> SEQUENCE: 49

Leu Gln Tyr Gly Asn Leu Leu Tyr Ala
1               5

<210> SEQ ID NO 50
<211> LENGTH: 115
<212> TYPE: PRT
<213> ORGANISM: Artificial sequence
<220> FEATURE:
<223> OTHER INFORMATION: binding domain sequence

<400> SEQUENCE: 50

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Val Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110

Val Ser Ser
        115

<210> SEQ ID NO 51
<211> LENGTH: 8
<212> TYPE: PRT
<213> ORGANISM: Artificial sequence
<220> FEATURE:
<223> OTHER INFORMATION: binding domain sequence

<400> SEQUENCE: 51

Gly Phe Thr Val Ser Ser Asn Tyr
1               5

<210> SEQ ID NO 52
<211> LENGTH: 7
<212> TYPE: PRT
```

```
<213> ORGANISM: Artificial sequence
<220> FEATURE:
<223> OTHER INFORMATION: binding domain sequence

<400> SEQUENCE: 52

Ile Tyr Gly Ser Gly Arg Thr
1               5

<210> SEQ ID NO 53
<211> LENGTH: 9
<212> TYPE: PRT
<213> ORGANISM: Artificial sequence
<220> FEATURE:
<223> OTHER INFORMATION: binding domain sequence

<400> SEQUENCE: 53

Ala Arg Asp Thr Tyr Ala Met Asp Val
1               5

<210> SEQ ID NO 54
<211> LENGTH: 109
<212> TYPE: PRT
<213> ORGANISM: Artificial sequence
<220> FEATURE:
<223> OTHER INFORMATION: binding domain sequence

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Met Tyr Thr Phe Gly Gln Gly Thr Lys Leu Glu Ile Lys
            100                 105

<210> SEQ ID NO 55
<211> LENGTH: 7
<212> TYPE: PRT
<213> ORGANISM: Artificial sequence
<220> FEATURE:
<223> OTHER INFORMATION: binding domain sequence

<400> SEQUENCE: 55

Gln Ser Val Ser Ser Ser Tyr
1               5

<210> SEQ ID NO 56
<211> LENGTH: 10
<212> TYPE: PRT
<213> ORGANISM: Artificial sequence
<220> FEATURE:
<223> OTHER INFORMATION: binding domain sequence

<400> SEQUENCE: 56

Gln Gln Tyr Gly Ser Ser Pro Met Tyr Thr
1               5                   10
```

<210> SEQ ID NO 57
<211> LENGTH: 330
<212> TYPE: PRT
<213> ORGANISM: Homo Sapiens

<400> SEQUENCE: 57

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 58
<211> LENGTH: 330
<212> TYPE: PRT
<213> ORGANISM: Artificial sequence
<220> FEATURE:
<223> OTHER INFORMATION: Constant region

```
<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 59
<211> LENGTH: 330
<212> TYPE: PRT
<213> ORGANISM: Artificial sequence
<220> FEATURE:
<223> OTHER INFORMATION: Constant region

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Phe Glu Gly Gly Pro Ser Val Phe Leu Phe Pro Pro
        115                 120                 125
Lys Pro Lys Asp Thr Leu Met Ile Ser Arg Thr Pro Glu Val Thr Cys
        130                 135                 140
Val Val Val Ala Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 60
<211> LENGTH: 330
<212> TYPE: PRT
<213> ORGANISM: Artificial sequence
<220> FEATURE:
<223> OTHER INFORMATION: Constant region

<400> SEQUENCE: 60

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 61
<211> LENGTH: 330
<212> TYPE: PRT
<213> ORGANISM: Artificial sequence
<220> FEATURE:
<223> OTHER INFORMATION: Constant region

<400> SEQUENCE: 61

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
                    85                  90                  95
Arg Val Glu Pro Lys Ser Cys Asp Lys Thr His Thr Cys Pro Pro Cys
                100                 105                 110
Pro Ala Pro Glu Phe Glu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Ala Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Arg Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 62
<211> LENGTH: 330
<212> TYPE: PRT
<213> ORGANISM: Artificial sequence
<220> FEATURE:
<223> OTHER INFORMATION: Constant region

<400> SEQUENCE: 62

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 63
<211> LENGTH: 107
<212> TYPE: PRT
<213> ORGANISM: Homo Sapiens

<400> SEQUENCE: 63

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 64
<211> LENGTH: 106
<212> TYPE: PRT
<213> ORGANISM: Homo Sapiens

<400> SEQUENCE: 64

Gly Gln Pro Lys Ala Ala Pro Ser Val Thr Leu Phe Pro Pro Ser Ser
```

```
                1               5                  10                 15
            Glu Glu Leu Gln Ala Asn Lys Ala Thr Leu Val Cys Leu Ile Ser Asp
                            20                 25                 30

Phe Tyr Pro Gly Ala Val Thr Val Ala Trp Lys Ala Asp Ser Ser Pro
                        35                 40                 45

Val Lys Ala Gly Val Glu Thr Thr Thr Pro Ser Lys Gln Ser Asn Asn
                    50                 55                 60

Lys Tyr Ala Ala Ser Ser Tyr Leu Ser Leu Thr Pro Glu Gln Trp Lys
            65                  70                 75                  80

Ser His Arg Ser Tyr Ser Cys Gln Val Thr His Glu Gly Ser Thr Val
                            85                 90                 95

Glu Lys Thr Val Ala Pro Thr Glu Cys Ser
                        100                105

<210> SEQ ID NO 65
<211> LENGTH: 120
<212> TYPE: PRT
<213> ORGANISM: Artificial sequence
<220> FEATURE:
<223> OTHER INFORMATION: binding domain sequence

<400> SEQUENCE: 65

Gln Leu Gln Leu Gln Glu Ser Gly Pro Gly Leu Val Lys Pro Ser Glu
            1               5                  10                 15

Thr Leu Ser Leu Thr Cys Thr Val Ser Gly Gly Ser Ile Lys Ser Gly
                            20                 25                 30

Ser Tyr Tyr Trp Gly Trp Ile Arg Gln Pro Pro Gly Lys Gly Leu Glu
                        35                 40                 45

Trp Ile Gly Asn Ile Tyr Tyr Ser Gly Ser Thr Tyr Tyr Asn Pro Ser
                    50                 55                 60

Leu Arg Ser Arg Val Thr Ile Ser Val Asp Thr Ser Lys Asn Gln Phe
            65                  70                 75                  80

Ser Leu Lys Leu Ser Ser Val Thr Ala Ala Asp Thr Ala Val Tyr Tyr
                            85                 90                 95

Cys Ala Arg Glu Gly Tyr Pro Asn Gln Phe Asp Pro Trp Gly Gln
                        100                105                110

Gly Thr Leu Val Thr Val Ser Ser
                        115                120

<210> SEQ ID NO 66
<211> LENGTH: 10
<212> TYPE: PRT
<213> ORGANISM: Artificial sequence
<220> FEATURE:
<223> OTHER INFORMATION: binding domain sequence

<400> SEQUENCE: 66

Gly Gly Ser Ile Lys Ser Gly Ser Tyr Tyr
            1               5                  10

<210> SEQ ID NO 67
<211> LENGTH: 7
<212> TYPE: PRT
<213> ORGANISM: Artificial sequence
<220> FEATURE:
<223> OTHER INFORMATION: binding domain sequence

<400> SEQUENCE: 67

Ile Tyr Tyr Ser Gly Ser Thr
            1               5
```

<210> SEQ ID NO 68
<211> LENGTH: 12
<212> TYPE: PRT
<213> ORGANISM: Artificial sequence
<220> FEATURE:
<223> OTHER INFORMATION: binding domain sequence

<400> SEQUENCE: 68

Ala Arg Glu Gly Ser Tyr Pro Asn Gln Phe Asp Pro
1               5                   10

<210> SEQ ID NO 69
<211> LENGTH: 107
<212> TYPE: PRT
<213> ORGANISM: Artificial sequence
<220> FEATURE:
<223> OTHER INFORMATION: binding domain sequence

<400> SEQUENCE: 69

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys
            100                 105

<210> SEQ ID NO 70
<211> LENGTH: 6
<212> TYPE: PRT
<213> ORGANISM: Artificial sequence
<220> FEATURE:
<223> OTHER INFORMATION: binding domain sequence

<400> SEQUENCE: 70

Gln Ser Val Ser Ser Asn
1               5

<210> SEQ ID NO 71
<211> LENGTH: 9
<212> TYPE: PRT
<213> ORGANISM: Artificial sequence
<220> FEATURE:
<223> OTHER INFORMATION: binding domain sequence

<400> SEQUENCE: 71

Gln Gln Tyr His Ser Phe Pro Phe Thr
1               5